United States Patent
Li

(10) Patent No.: US 11,837,354 B2
(45) Date of Patent: Dec. 5, 2023

(54) CONTRAST-AGENT-FREE MEDICAL DIAGNOSTIC IMAGING

(71) Applicant: London Health Sciences Centre Research Inc., London (CA)

(72) Inventor: Shuo Li, London (CA)

(73) Assignee: London Health Sciences Centre Research Inc., London (CA)

(*) Notice: Subject to any disclaimer, the term of this patent is extended or adjusted under 35 U.S.C. 154(b) by 70 days.

(21) Appl. No.: 17/138,353

(22) Filed: Dec. 30, 2020

(65) Prior Publication Data
US 2022/0208355 A1 Jun. 30, 2022

(51) Int. Cl.
*G06K 9/00* (2022.01)
*G16H 30/40* (2018.01)
(Continued)

(52) U.S. Cl.
CPC .............. *G16H 30/40* (2018.01); *G06N 3/084* (2013.01); *G06N 3/088* (2013.01); *G06T 7/0016* (2013.01); *G06T 2207/10088* (2013.01); *G06T 2207/20081* (2013.01); *G06T 2207/20084* (2013.01); *G06T 2207/30096* (2013.01)

(58) Field of Classification Search
CPC ................... G06T 2207/10088; G06T 2207/20081–20084; G06T 2210/41; G06T 2207/30096; G06T 7/11; G06T 7/10; G06T 7/194; G06T 7/0012–0016; G06T 2207/30004–30104; G01R 33/56308–5635; A61B 5/055; A61B 6/481; A61B 2576/00–02; G06V 10/70–87; G06V 10/764;
(Continued)

(56) References Cited

U.S. PATENT DOCUMENTS

| 2002/0107438 A1* | 8/2002 | Liu | ........................ A61B 5/055 600/410 |
| 2019/0122348 A1* | 4/2019 | Jensen | ................... G06T 11/00 |

(Continued)

OTHER PUBLICATIONS

Beckett et al. (2015) "Safe use of contrast media: what the radiologist needs to know", Radiographics 35: 1738-1750.
(Continued)

*Primary Examiner* — Atiba O Fitzpatrick
(74) *Attorney, Agent, or Firm* — Knobbe Martens Olson & Bear LLP

(57) ABSTRACT

Described herein is medical imaging technology for concurrent and simultaneous synthesis of a medical CA-free-AI-enhanced image and medical diagnostic image analysis comprising: receiving a medical image acquired by a medical scanner in absence of contrast agent enhancement; providing the medical image to a computer-implemented machine learning model; concurrently performing a medical CA-free-AI-enhanced image synthesis task and a medical diagnostic image analysis task with the machine learning model; reciprocally communicating between the image synthesis task and the image analysis task for mutually dependent training of both tasks. Methods and systems and non-transitory computer readable media are described for execution of concurrent and simultaneous synthesis of a medical CA-free-AI-enhanced image and medical diagnostic image analysis.

21 Claims, 29 Drawing Sheets

(51) Int. Cl.
G06T 7/00 (2017.01)
G06N 3/084 (2023.01)
G06N 3/088 (2023.01)

(58) Field of Classification Search
CPC ....... G06V 2201/03–033; G06V 10/26; G06V 10/40; G06N 20/20; G06N 3/088; G06N 3/0445

See application file for complete search history.

(56) References Cited

U.S. PATENT DOCUMENTS

2020/0134876 A1* 4/2020 Park .................. G06T 11/00
2020/0311932 A1* 10/2020 Hooper ................ G06N 3/088
2022/0198655 A1* 6/2022 Grimmer ............. G06V 10/761

OTHER PUBLICATIONS

Li, Chongxuan et al. (2017) "Triple generative adversarial nets", in *Advances in Neural Information Processing Systems*, pp. 4088-4098.

Costa et al. (2017) "End-to-end adversarial retinal image synthesis", IEEE Transactions on Medical Imaging 37: 781-791.

Goodfellow et al. (2014) "Generative adversarial nets", in *Advances in Neural Information Processing Systems*, pp. 2672-2680.

Gulrajani et al. (2017) "Improved Training of Wasserstein GANs", in *Advances in Neural Information Processing Systems*, pp. 5767-5777.

He et al. (2016) "Deep residual learning for image recognition", in *Proceedings of the IEEE conference on Computer Vision and Pattern Recognition*, pp. 770-778.

Huang et al. (2017) "Stacked generative adversarial networks", in *Proceedings of the IEEE Conference on Computer Vision and Pattern Recognition*, pp. 5077-5086.

Karras et al. (2017) "Progressive growing of GANs for improved quality, stability, and variation", arXiv preprint arXiv:1710.10196.

Korkinof et al. (2018) "High-resolution mammogram synthesis using progressive generative adversarial networks", arXiv preprint arXiv:1807.03401.

Leiner (2019) "Deep learning for detection of myocardial scar tissue: Goodbye to gadolinium?", Radiology 291: 618-619.

Mao et al. (2017) "Least squares generative adversarial networks", in *Computer Vision (ICCV)*, 2017 IEEE International Conference on, IEEE, pp. 2813-2821.

Mirza et al. (2014) "Conditional generative adversarial nets", arXiv preprint arXiv:1411.1784.

Nie et al. (2018) "Medical image synthesis with deep convolutional adversarial networks", IEEE Transactions on Biomedical Engineering 65: 2720-2730.

Ordovas et al. (2011) "Delayed contrast enhancement on MR images of myocardium: past, present, future", Radiology 261: 358-374.

Peng et al. (2017) "Large kernel matters—improve semantic segmentation by global convolutional network", in: Proceedings of the IEEE Conference on Computer Vision and Pattern Recognition, pp. 4353-4361.

Shen et al. (2018) "FaceID-GAN: Learning a symmetry three-player GAN for identity-preserving face synthesis", in: Proceedings of the IEEE Conference on Computer Vision and Pattern Recognition, pp. 821-830.

Vandenhende, et al. (2019) "A three-player GAN: generating hard samples to improve classification networks", arXiv preprint arXiv:1903.03496.

Vaswani et al. (2017) "Attention is all you need", in: Advances in Neural Information Processing Systems, pp. 5998-6008.

Wang et al. (2018) "Non-local neural networks", in *Proceedings of the IEEE Conference on Computer Vision and Pattern Recognition*, pp. 7794-7803.

Xu et al. (2018) "MuTGAN: Simultaneous segmentation and quantification of myocardial infarction without contrast agents via joint adversarial learning", in: MICCAI, Springer, pp. 525-534.

Xu et al. (2018) Direct delineation of myocardial infarction without contrast agents using a joint motion feature learning architecture. Medical Image Analysis 50: 82-94.

Xu et al. (2017) "Direct detection of pixel-level myocardial infarction areas via a deep-learning algorithm", in *International Conference on Medical Image Computing and Computer-Assisted Intervention*, Springer, pp. 240-249.

Xu, Chenchu, et al., "Contrast agent-free synthesis and segmentation of ischemic heart disease images using progressive sequential causal GANs", Medical Image Analysis 62 (2020) 101668.

Zhang et al. (2018) "Self-attention generative adversarial networks", arXiv preprint arXiv:1805.08318.

Zhang et al. (2018) "StackGAN++: Realistic image synthesis with stacked generative adversarial networks", IEEE Transactions on Pattern Analysis and Machine Intelligence 41: 1947-1962.

Zhao et al., (2020) "Tripartite-GAN: Synthesizing liver contrast-enhanced MRI to improve tumor detection", Medical Image Analysis 63, article 101667.

Zhao et al. (2017) "Pyramid scence parsing networks", in *Proceedings of the IEEE Conference on Computer Vision and Pattern Recognition*, pp. 2881-2890.

* cited by examiner

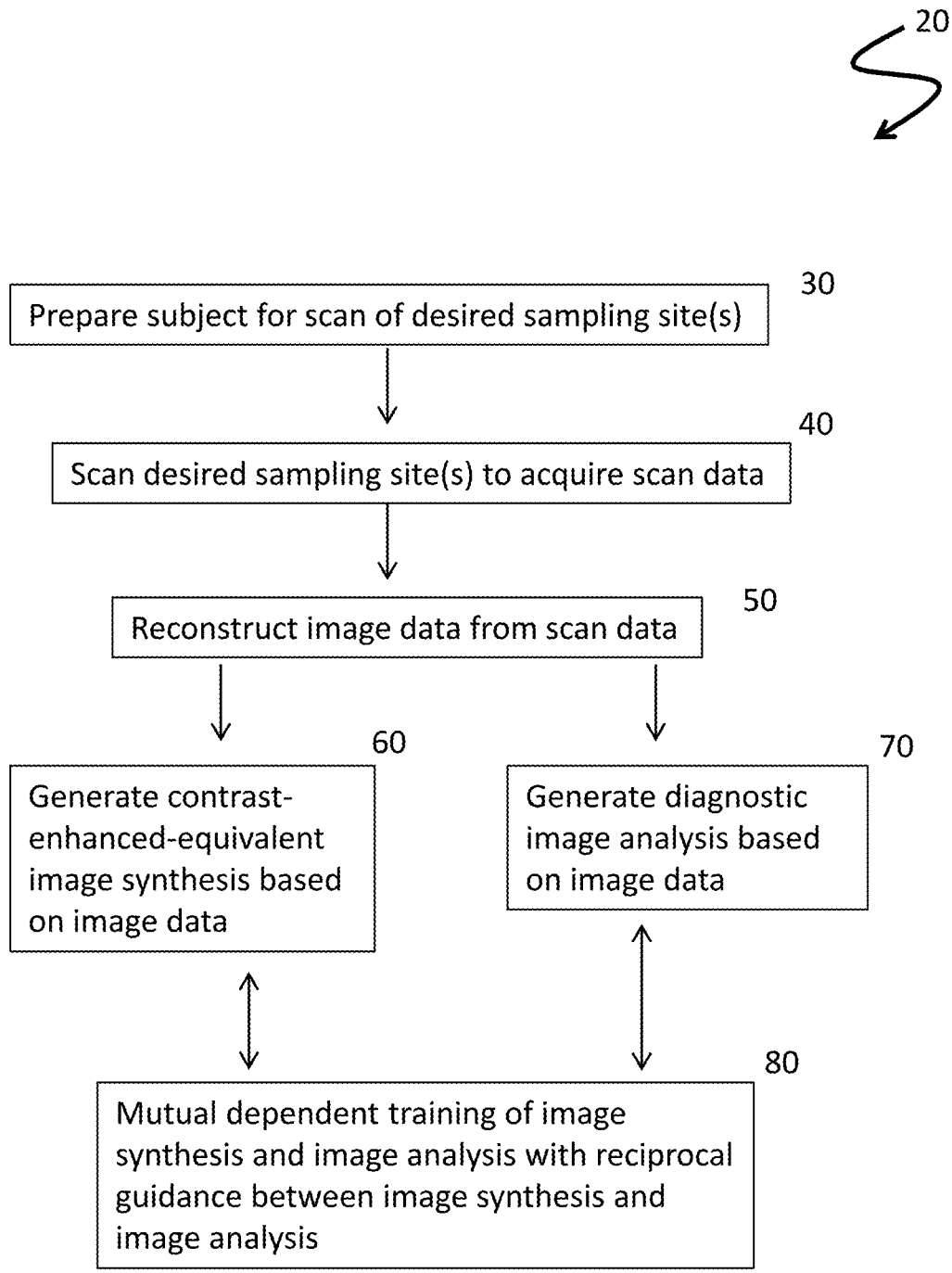

Our one-stop CA-free workflow

Existing CA-free segmentation method

Current clinical workflow

Scar size = Number of scar pixels
Scar ratio = (Number of scar pixels) / (Number of healthy myocardium pixels)
Transmurality = (Scar width / (Myocardial width)

CONTRAST-AGENT-FREE MEDICAL DIAGNOSTIC IMAGING

BACKGROUND OF THE INVENTION

Field of the Invention

The present invention relates to medical imaging, and more particularly medical imaging acquired without administration of a contrast agent.

Description of the Related Art

Contrast agent (CA) administration to a patient is a frequent prerequisite for medical imaging.

Taking heart imaging as an example, gadolinium-based CA is administered to a patient for cardiac magnetic resonance (MR) imaging, for example as part of current ischemic heart disease (IHD) treatment workflow in cardiac radiology (Beckett et al., 2015). IHD diagnosis/treatment is a relevant example of cardiac MR imaging as a majority of patients undergoing cardiac MR imaging are being evaluated for possible myocardial ischemia, and IHD in general and subtypes of IHD may be distinguished according to patterns of contrast enhancement. CA imaging uses chemical substances in MR scans. After the CA is injected into the body, CA imaging produces a late gadolinium enhancement (LGE) image to illustrate IHD scars that are invisible under regular MR imaging and improves the clarity of other internal and surrounding cardiac tissues (i.e., muscles, cavities, and even blood).

Terminology of early versus late gadolinium enhancement references a lapsed time after injection for acquiring imaging data. An advantage of LGE is due to a relative contrast enhancement change between healthy and diseased tissue at a later time after injection of CA favoring enhancement of diseased tissue. For example, at an early time (1-3 min post-injection) gadolinium resides primarily in the blood pool and healthy myocardium. At a later time (5-20 min post-injection) gadolinium is relatively cleared from healthy tissue and is relatively retained by diseased tissue.

After the CA imaging, manual segmentation helps radiologists to segment multiple cardiac tissues to delineate diagnosis-related tissues (scars, myocardium, etc.), and the subsequent quantitative evaluation of these segmented tissues results in various diagnosis metrics to accurately report the presence or the progression of IHD.

However, with this workflow (i.e., CA imaging first followed by manual segmentation second), there are still concerns regarding toxicity, high inter-observer variability, and ineffectiveness. 1) CAs have been highlighted in numerous clinical papers showing their potential toxicity, retention in the human body, and importantly, their potential to induce fatal nephrogenic systemic fibrosis (Ordovas and Higgins, 2011). 2) Manual segmentation has well-known issues regarding high inter-observer variability and non-reproducibility, which are caused by the difference in expertise among clinicians (Ordovas and Higgins, 2011). 3) CA imaging followed by segmentation leads to additional time and effort for patient and clinician, as well as high clinical resource costs (labor and equipment).

To date, a few initial CA-free and automatic segmentation methods have been reported. However, even the state-of-the-art methods only produce a binary scar image that fails to provide a credible diagnosis (Xu et al., 2018a; 2018b).

As another example of medical imaging acquired with CA administration, the MR examination of liver relies heavily on CA injection. For example, in liver cancer diagnosis, non-contrast enhanced MR imaging (NCEMRI) obtained without CA injection can barely distinguish areas of hemangioma (a benign tumor) and hepatocellular carcinoma (HCC, a malignant tumor). On the contrary, contrast-enhanced MRI (CEMRI) obtained with CA injection shows the area of hemangioma as a gradual central filling and bright at the edge and the area of HCC as entirely or mostly bright through the whole tumor, which provides an accurate and easy way to diagnose hemangioma and HCC.

However, gadolinium-based CA brings inevitable shortcomings, suffering from high-risk, time-consuming, and expensive disadvantages. The high-risk disadvantage is due to potential toxic effect of gadolinium-based CA injection. The time-consuming disadvantage comes from the MRI process itself and the waiting-time after CA injection. The expensive disadvantage mainly comes from the cost of CA; in the USA alone, conservatively, if each dose of CA is $60, the direct material expense alone equates to roughly $1.2 billion in 2016 (Statistics from IQ-AI Limited Company, USA).

Accordingly, there is a need for contrast-agent-free medical diagnostic imaging.

SUMMARY OF THE INVENTION

In an aspect there is provided, a medical imaging method for concurrent and simultaneous synthesis of a medical CA-free-AI-enhanced image and medical diagnostic image analysis comprising:
  receiving a medical image acquired by a medical scanner in absence of contrast agent enhancement;
  providing the medical image to a computer-implemented machine learning model;
  concurrently performing a medical CA-free-AI-enhanced image synthesis task and a medical diagnostic image analysis task with the machine learning model;
  reciprocally communicating between the image synthesis task and the image analysis task for mutually dependent training of both tasks.

In another aspect there is provided, a medical imaging method for concurrent and simultaneous synthesis and segmentation of a CA-free-AI-enhanced image comprising:
  receiving a magnetic resonance (MR) image acquired by a medical MR scanner in absence of contrast agent enhancement;
  providing the MR image to a progressive framework of a plurality of generative adversarial networks (GAN);
  inputting the MR image into a first GAN;
  obtaining a coarse tissues mask from the first GAN;
  inputting the coarse tissues mask and the MR image into a second GAN;
  obtaining a CA-free-AI-enhanced image from the second GAN;
  inputting the CA-free-AI-enhanced image and the MR image into a third GAN;
  obtaining a diagnosis-related tissue segmented image from the third GAN.

In yet another aspect there is provided, a medical imaging method for concurrent and simultaneous synthesis of a CA-free-AI-enhanced image and tumor detection comprising:
  receiving a magnetic resonance (MR) image acquired by a medical MR scanner in absence of contrast agent enhancement;

providing the MR image to a tripartite generative adversarial network (GAN) comprising a generator network, a discriminator network and a detector network;

inputting the MR image into the generator network;

obtaining a CA-free-AI-enhanced image and an attention map of tumor specific features from the generator network;

inputting the CA-free-AI-enhanced image and the attention map into the detector network;

obtaining a tumor location and a tumor classification extracted from the CA-free-AI-enhanced image by the detector network;

training the generator network by both adversarial learning with the discriminator network and back-propagation with the detector network.

In further aspects there are provided, systems and non-transitory computer readable media for execution of concurrent and simultaneous synthesis of a medical CA-free-AI-enhanced image and medical diagnostic image analysis described herein.

For example, there is provided, a medical imaging system for concurrent and simultaneous synthesis of a medical CA-free-AI-enhanced image and medical diagnostic image analysis comprising:

an interface device configured for receiving a medical image acquired by a medical scanner in absence of contrast agent enhancement;

a memory configured for storing the medical image and a computer-implemented machine learning model;

a processor configured for:

inputting the medical image to the computer-implemented machine learning model;

concurrently performing a medical CA-free-AI-enhanced image synthesis task and a medical diagnostic image analysis task with the machine learning model;

reciprocally communicating between the image synthesis task and the image analysis task for mutually dependent training of both tasks.

As another example there is provided, a non-transitory computer readable medium embodying a computer program for concurrent and simultaneous synthesis of a medical CA-free-AI-enhanced image and medical diagnostic image analysis comprising:

computer program code for receiving a medical image acquired by a medical scanner in absence of contrast agent enhancement;

computer program code for providing the medical image to a computer-implemented machine learning model;

computer program code for concurrently performing a medical CA-free-AI-enhanced image synthesis task and a medical diagnostic image analysis task with the machine learning model;

computer program code for reciprocally communicating between the image synthesis task and the image analysis task for mutually dependent training of both tasks.

BRIEF DESCRIPTION OF THE DRAWINGS

FIG. 2 shows a flow diagram of a CA-free medical imaging method.

Figure 17:
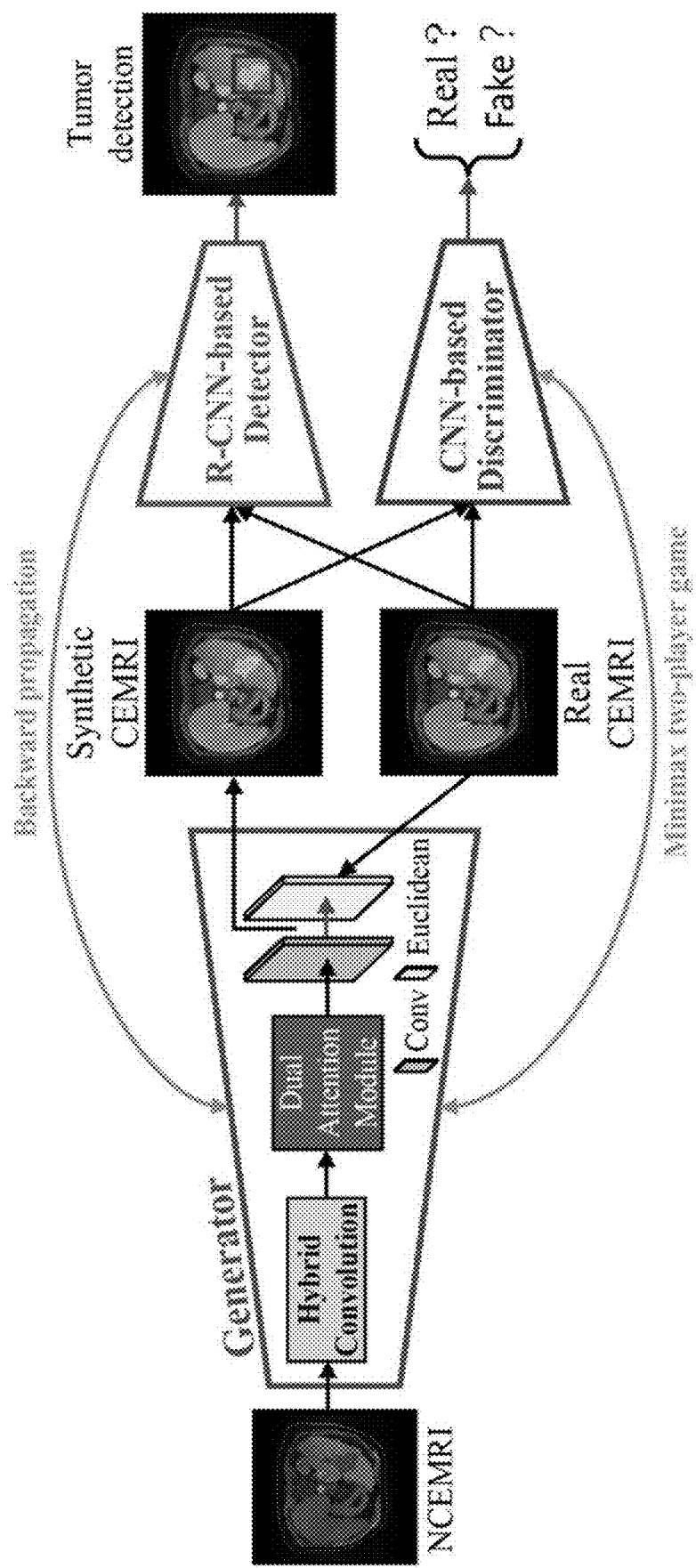

FIG. 17 shows a schematic of a variant of the present CA-free medical technology formed as a Tripartite-GAN that generates synthetic CEMRI for tumor detection by the combination of three associated-task networks, the attention-aware generator, the CNN-based discriminator and the R-CNN-based detector. The R-CNN-based detector directly detects tumor from the synthetic CEMRI and improves the accuracy of synthetic CEMRI generation via back-propagation. The CNN-based discriminator urges generator to generate more realistic synthetic CEMRI via adversarial-learning-strategy.

Figure 18:
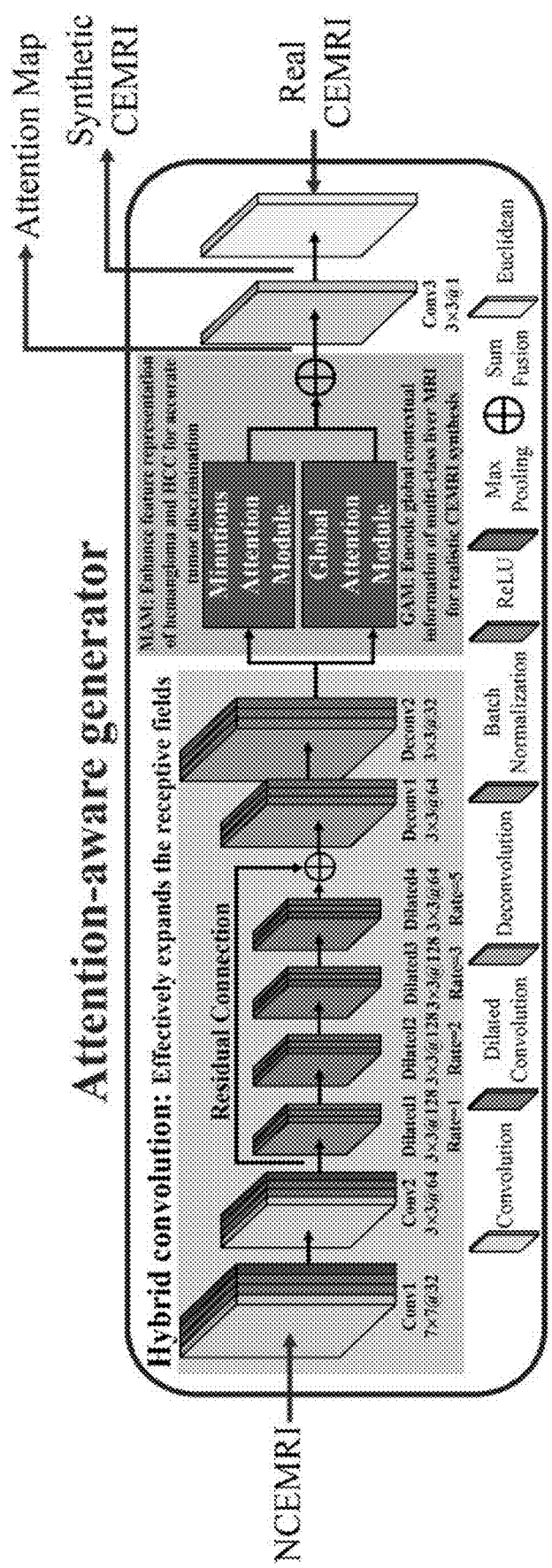

FIG. 18 shows that the generator in the Tripartite-GAN aims to synthesize accurate and realistic synthetic CEMRI. It uses a hybrid convolution including standard convolution layers, dilated convolution layers, and deconvolution layers. The dilated convolution is utilized to enlarge receptive fields. The two standard convolution layers and two deconvolution layers are connected to the front and back of dilated convolution, which reduces the size of feature maps to expand the receptive fields more efficiently. Following the hybrid convolution, the dual attention module (DAM including MAM and GAM) enhances the detailed feature extraction and aggregates long-range contextual information of the generator, which improves the detailed synthesis of the specificity of the tumor and the spatial continuity of the multi-class liver MRI.

Figure 19:
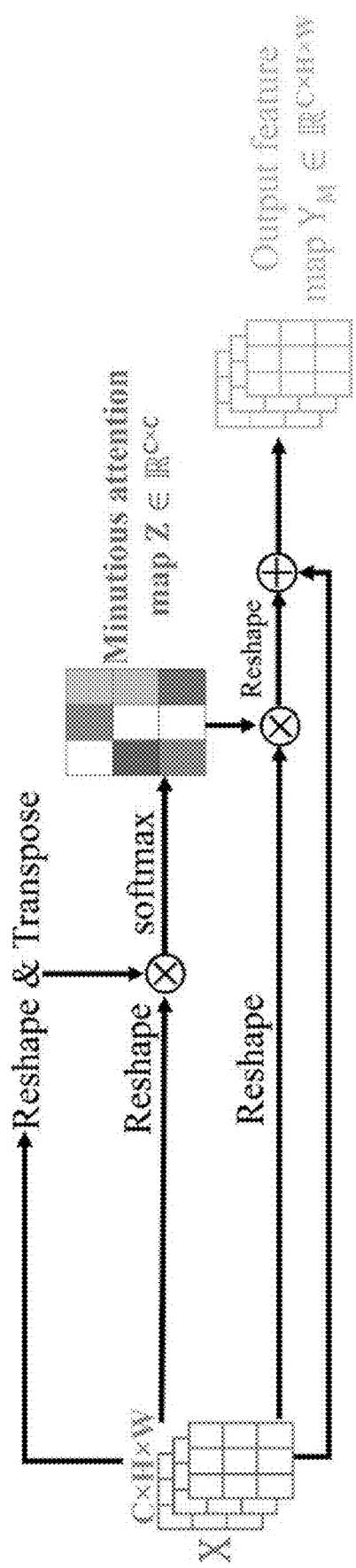

FIG. 19 shows a schematic of MAM that enhances the detailed feature extraction by utilizing the interdependencies between channel maps X.

Figure 20:
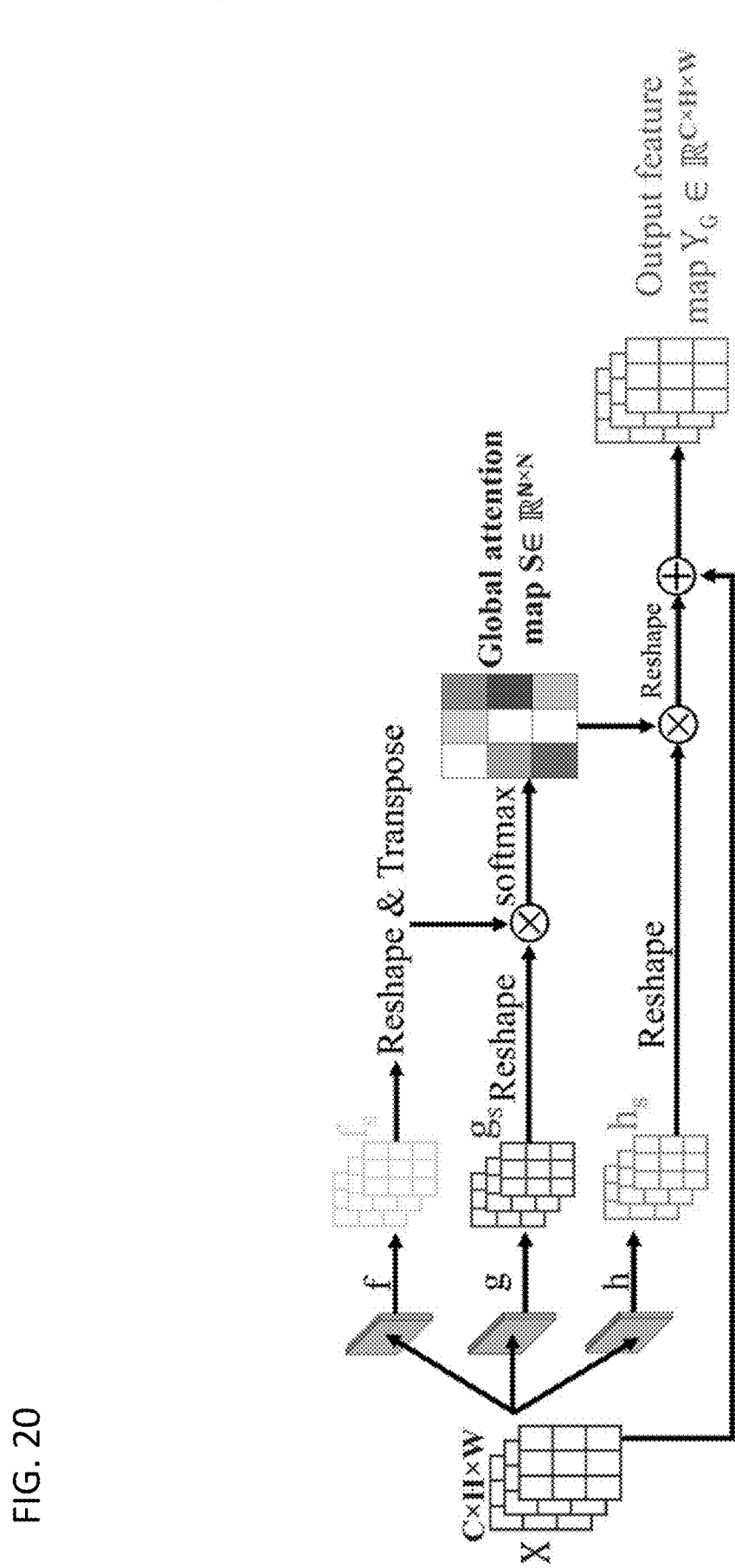

FIG. 20 shows a schematic of GAM that captures global dependencies of multi-class liver MRI by encoding global contextual information into local features.

Figure 21:
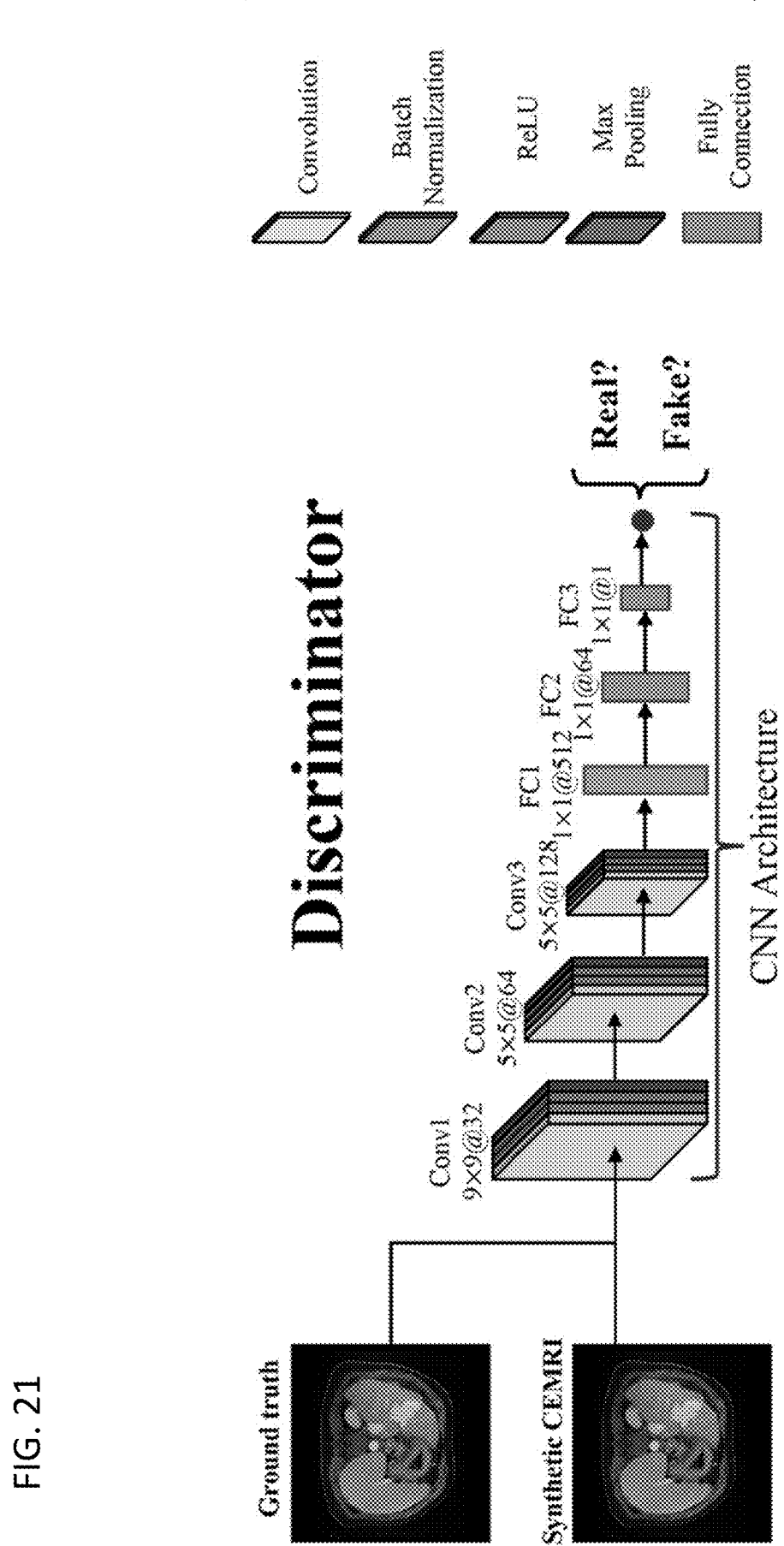

FIG. 21 shows a schematic of a CNN architecture of the discriminative network that receives the ground truth of CEMRI and the synthetic CEMRI, and then outputs the discriminative results of real or fake. Its adversarial strategy eagerly supervises attention-aware generator to find its own mistakes, which increased the authenticity of the synthetic CEMRI.

Figure 22:
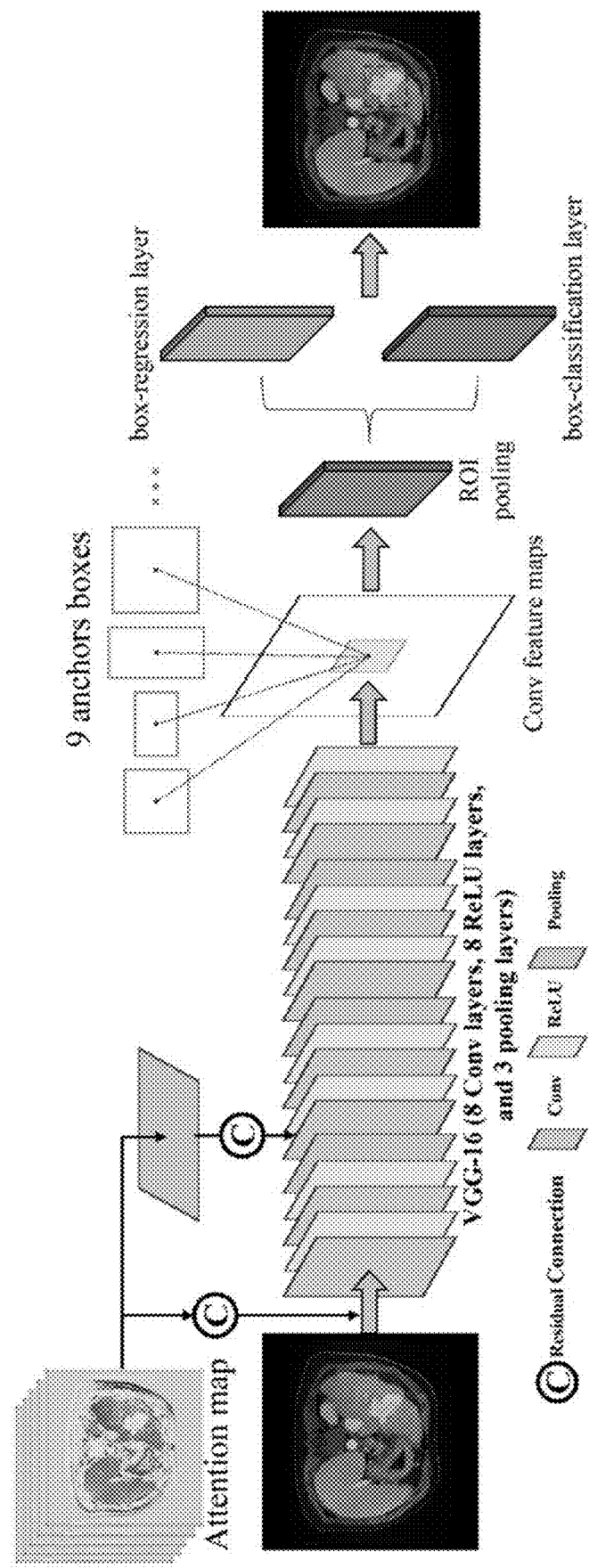

FIG. 22 shows a schematic of architecture of the tumor detection network that receives synthetic CEMRI and then accurately localizes the Region of Interest (RoI) of the tumor and classifies the tumor. Attention maps from the generator newly added into the detector in the manner of residual connection improve VGG-16 based convolution operation to extract tumor information better, which improves the performance of tumor detection. Meanwhile, the back-propagation of $L_{cls}$ prompts the generator to focus on the specificity between two types of tumors. Added $L_{cls}$ into Tripartite-GAN achieves a win-win between detector and generator via back-propagation.

Figure 23:
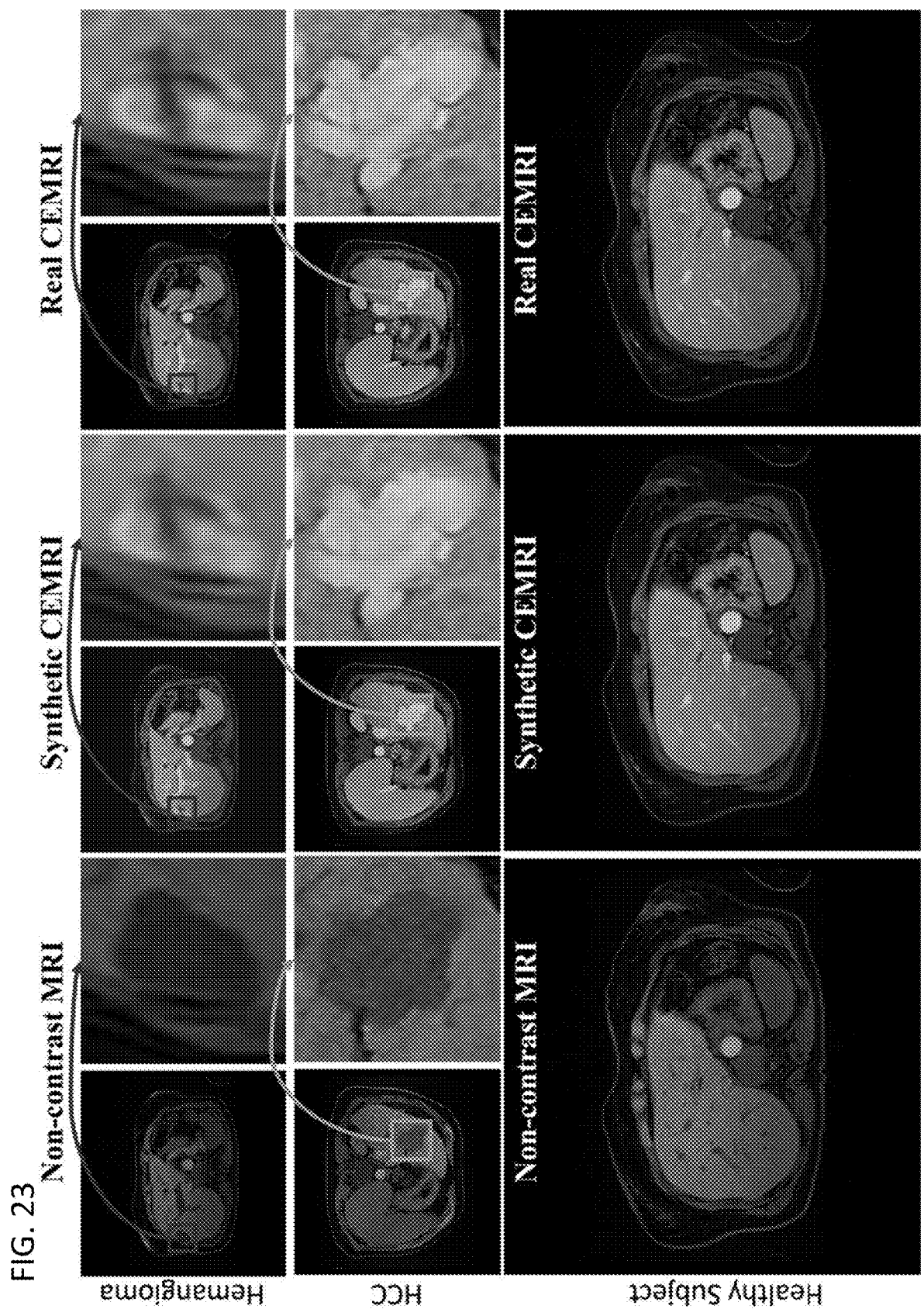

FIG. 23 shows that Tripartite-GAN generated synthetic CEMRI has an equal diagnostic value to real CEMRI. In the first and second rows, it is clear that the area of hemangioma becomes gradual central filling and bright at the edge in synthetic CEMRI, and the area of HCC becomes entirely or mostly bright through the whole tumor. The dark grey and light grey windows/boxes represent the hemangioma and HCC, respectively, and enlarge them on the right. The third (bottom) row is the synthesis result of healthy subjects.

Figure 24:
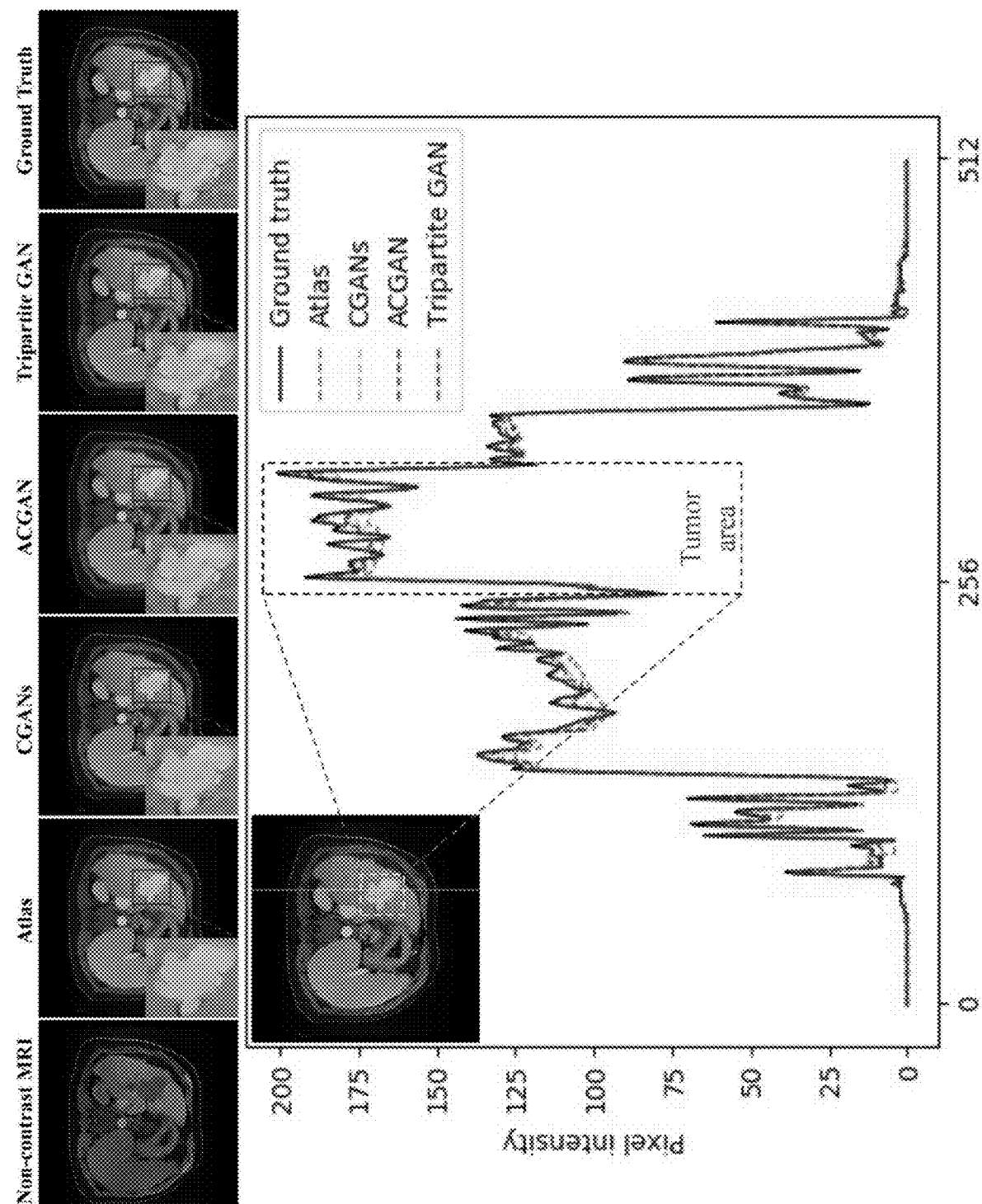

FIG. 24 shows Tripartite-GAN outperforms three other methods in comparison of detailed expression of the tumor and highly realistic synthetic-CEMRI. The pixel intensity curve and zoomed local patches of tumor area show that our Tripartite-GAN is more accurate than three other methods.

Figure 25:
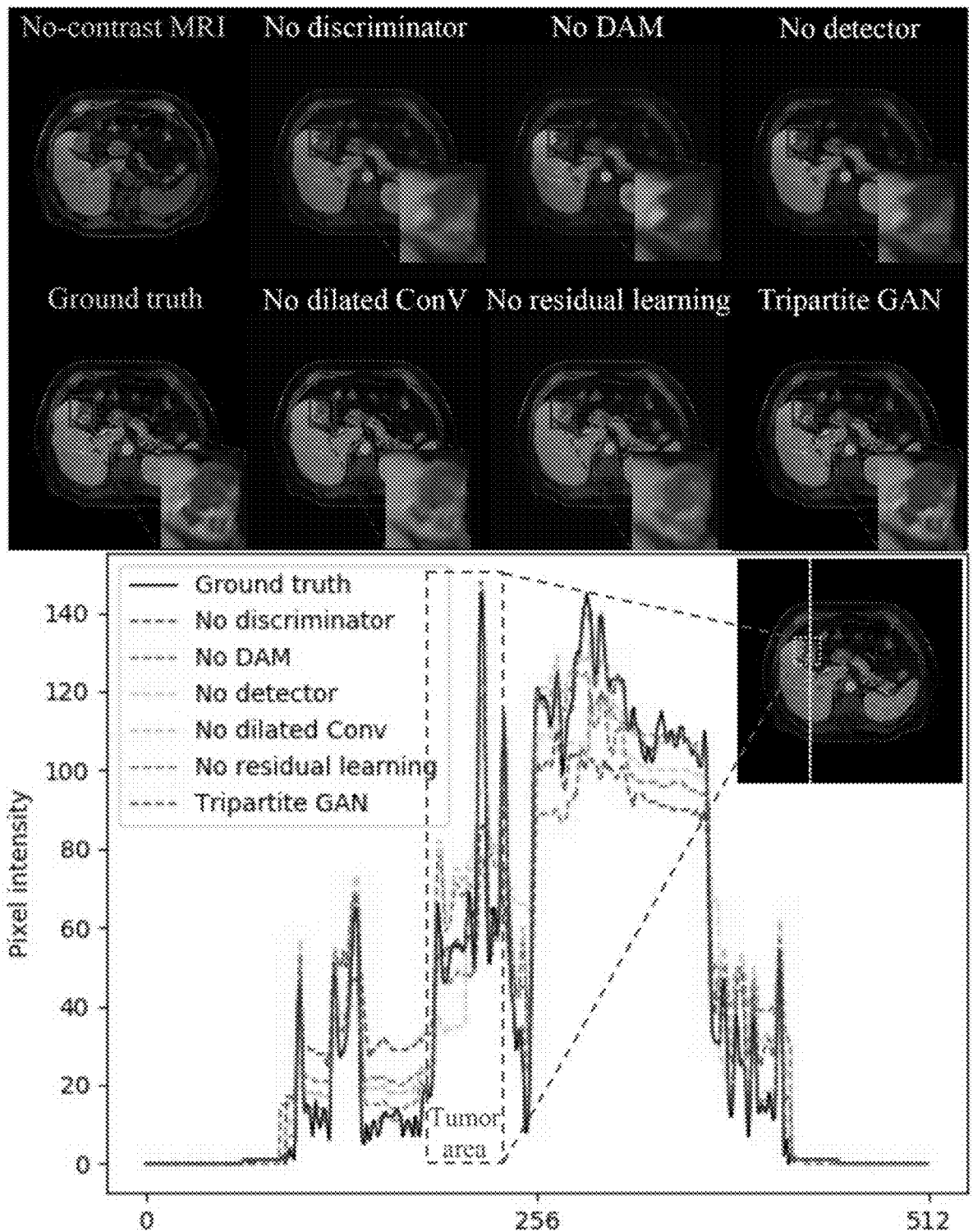

FIG. 25 shows that the ablation studies of No discriminator, No DAM, No detector, No dilated convolution, and No residual learning, which demonstrate contribution of various components of Tripartite-GAN to generation of synthetic CEMRI. The pixel intensity curve and zoomed local patches of tumor area demonstrate that our Tripartite-GAN is more accurate and more powerful in the detailed synthesis. The horizontal coordinate denotes pixel positions of the white line drawn in the ground truth, and the vertical coordinate is the pixel intensity of the corresponding pixel.

Figure 26:
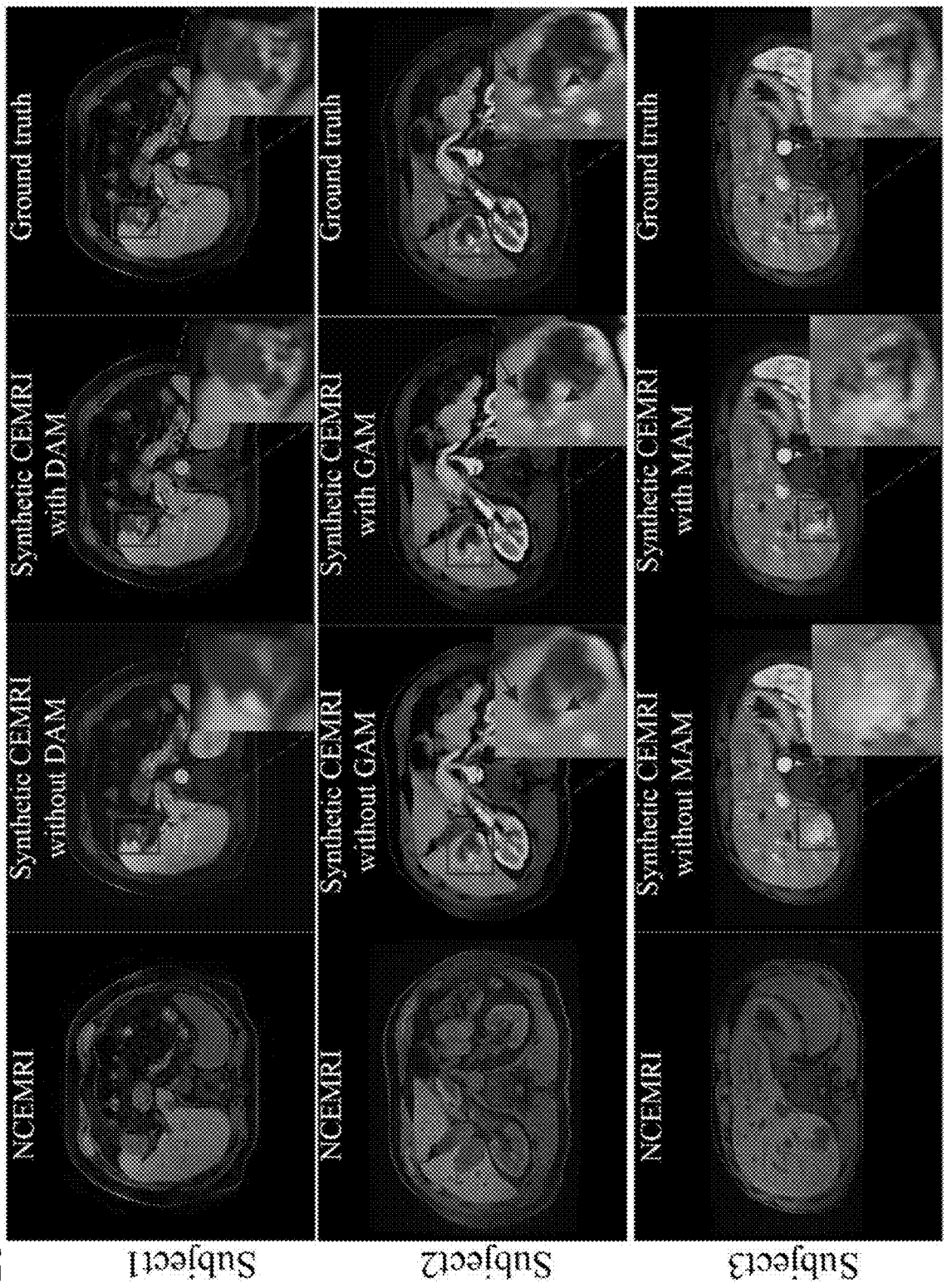

FIG. 26 show contributions of DAM, GAM, and MAM in Tri-partite GAN generated synthetic CEMRI. The subject1 demonstrates that DAM enhances the detailed synthesis of anatomy specificity and the spatial continuity. The subject2 demonstrates that GAM improves the spatial continuity of CEMRI synthesis. The subject3 demonstrates that MAM enhances the detailed feature extraction to improve the discrimination of hemangioma and HCC. The subject3 shows the failure of not being able to differentiate HCC and Hemangioma when MAM is removed, which incorrectly synthesizes the specificity of hemangioma into the specificity of HCC. The dark grey windows/boxes of zoomed local patches represent the tumor area. From left to right, they are the NCEMRI, the synthetic CEMRI without attention module, the synthetic CEMRI with attention module, and the ground truth, respectively.

Figure 27:
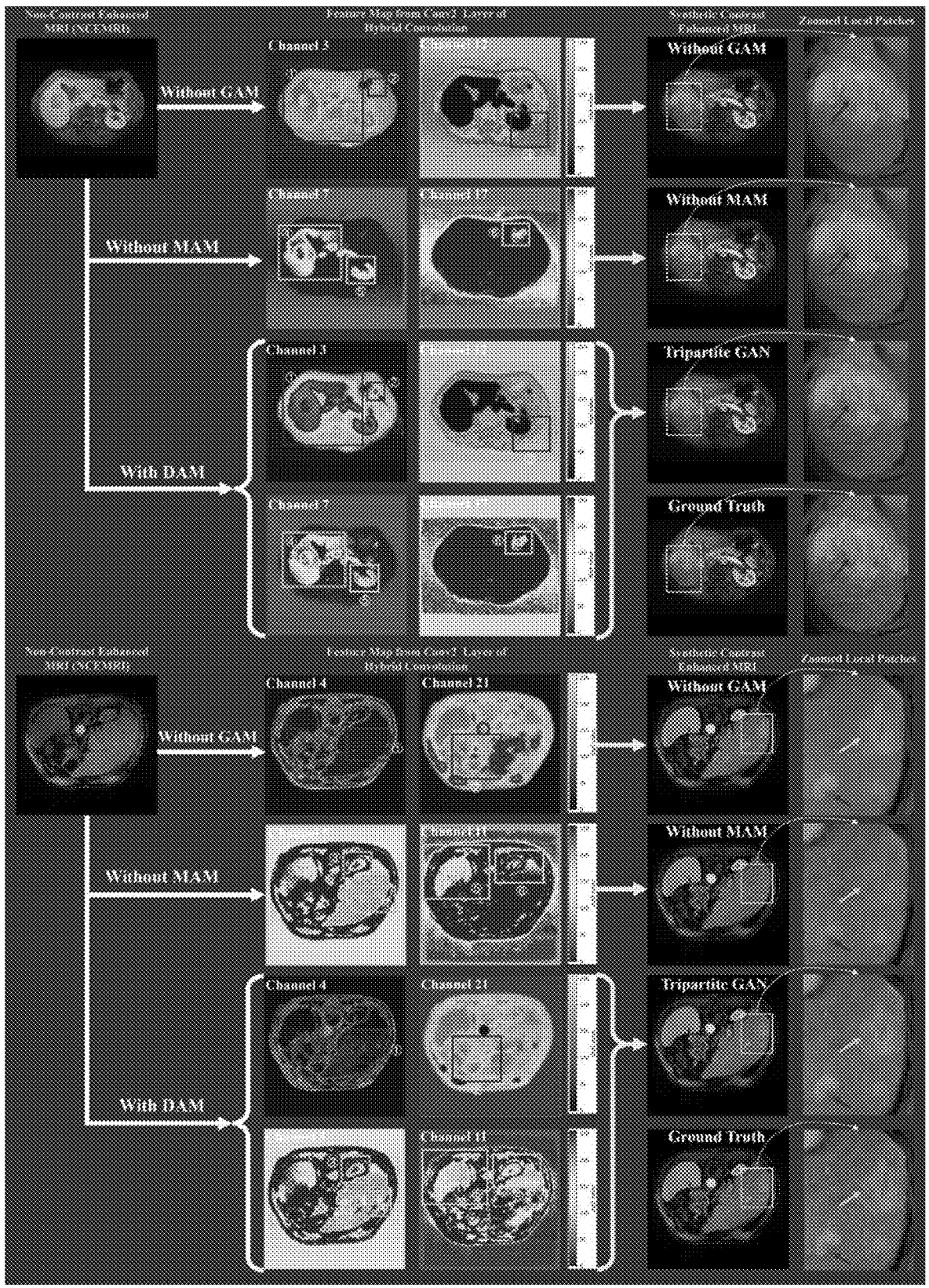

FIG. 27 shows two examples of CEMRI synthesis. The dark grey windows/boxes marked in the feature maps represent the difference of spatial continuity between Tripartite-GAN with and without GAM. The light grey windows/boxes marked in feature maps represent the difference of detailed feature extraction between Tripartite-GAN with and without MAM. The last two columns show the synthesis results and zoomed local patches of the tumor area. It is clear that MAM helps Tripartite-GAN enhance detailed synthesis, and GAM helps Tripartite-GAN improve the spatial continuity of synthetic CEMRI.

Figure 28:
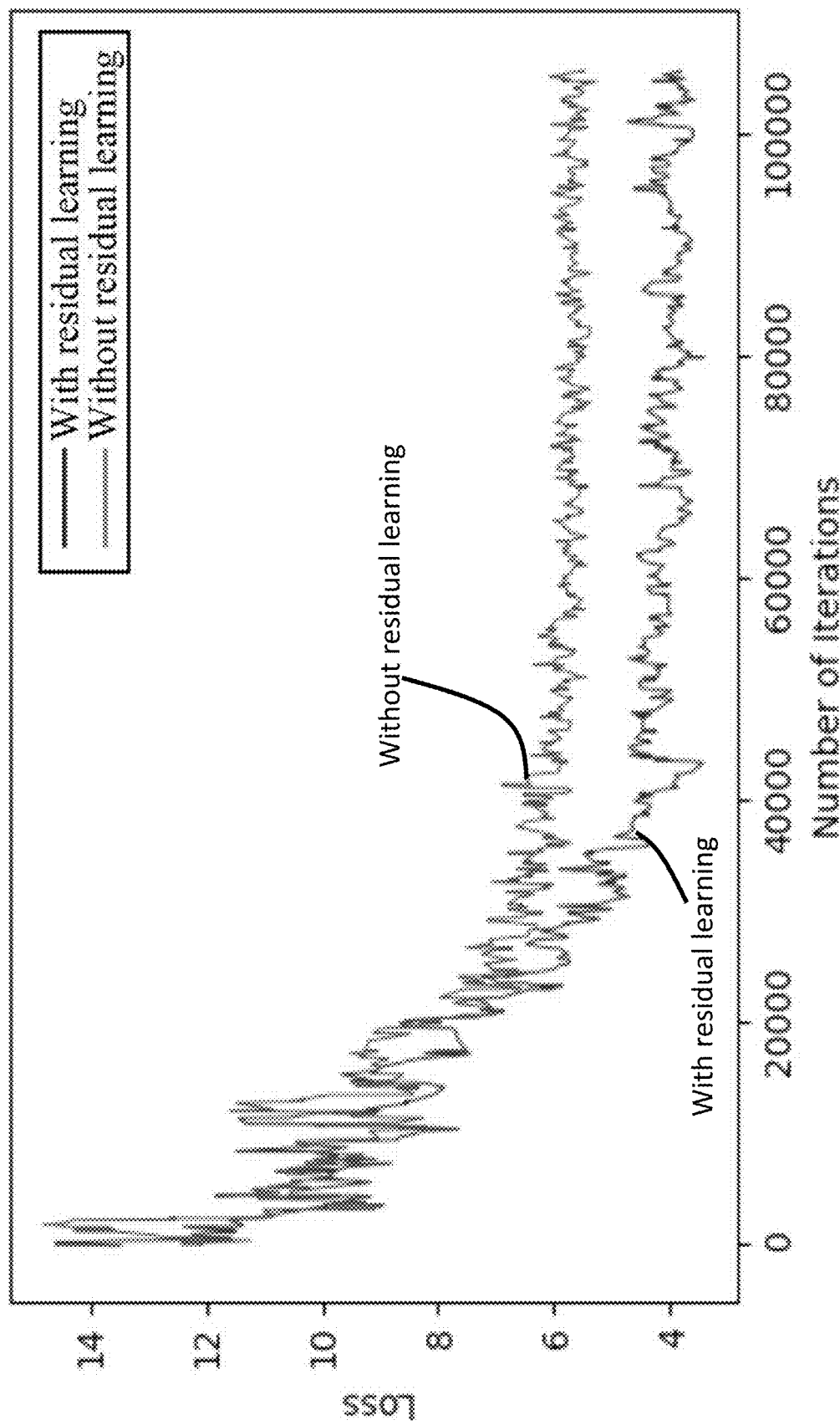

FIG. 28 shows that the generator of Tripartite-GAN with residual learning has lower training loss compared with the Tripartite-GAN without residual learning.

Figure 29:
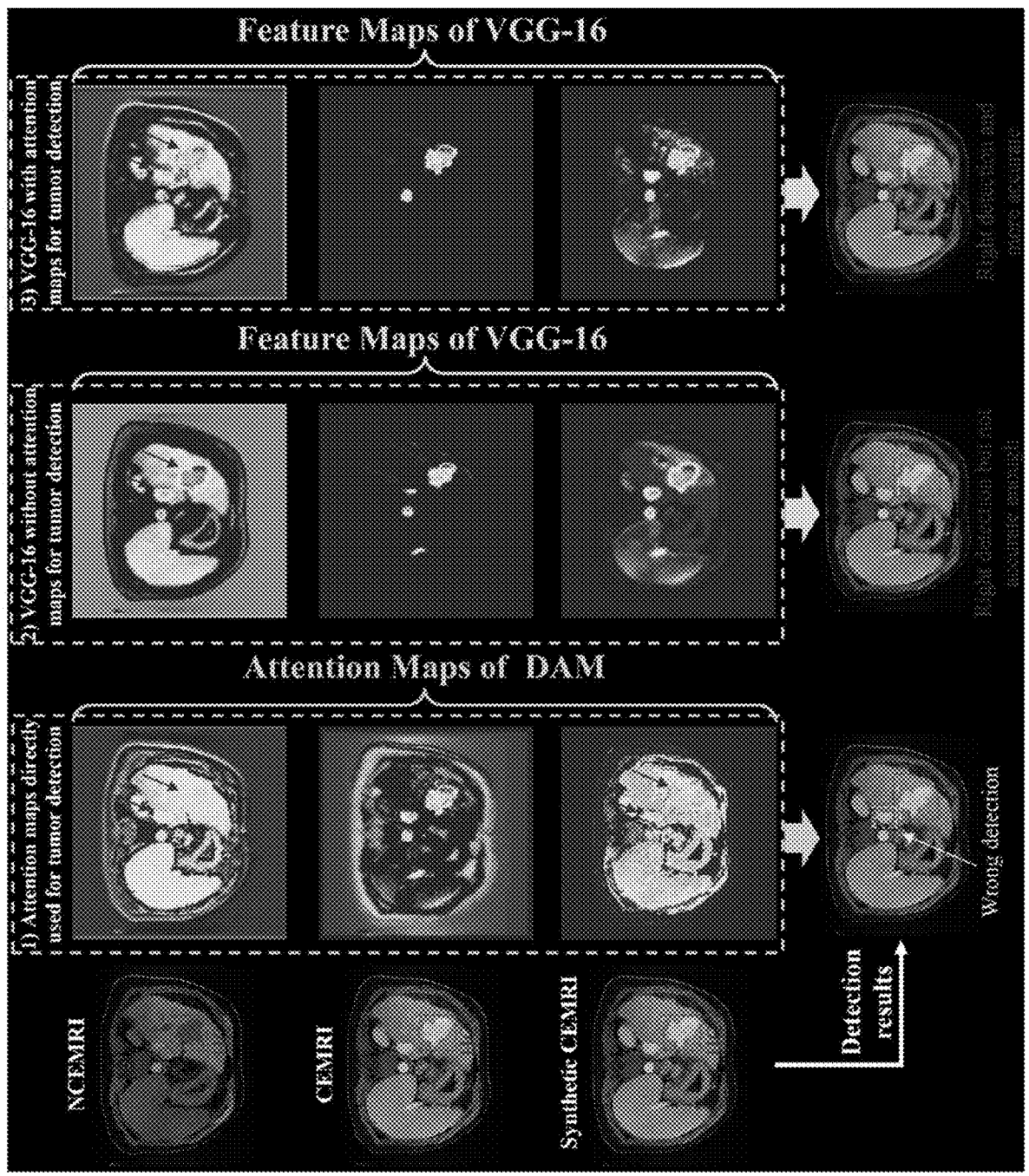

FIG. 29 shows that attention maps not only focus on the tumor but pay more attention to extract all features of all anatomy structure in liver MRI for multi-class liver MRI synthesis. The feature maps of VGG-16 without attention maps are more focused on tumor information. The feature maps of VGG-16 with attention maps also focus on tumor information but more accurate and detailed than without attention maps.

DETAILED DESCRIPTION OF PREFERRED EMBODIMENTS

With reference to the drawings, a system and method for CA-free-AI-enhanced imaging devoid of CA administration is described. The system and method compare favourably with current CA imaging techniques. The full wording of the term CA-free-AI-enhanced is contrast-agent-free-artificial-intelligence-enhanced with the CA-free component indicative of image or scan data acquired without CA administration and the AI-enhanced component indicative of machine learning enhancement of image/scan data acquired without CA administration.

Figure 1:
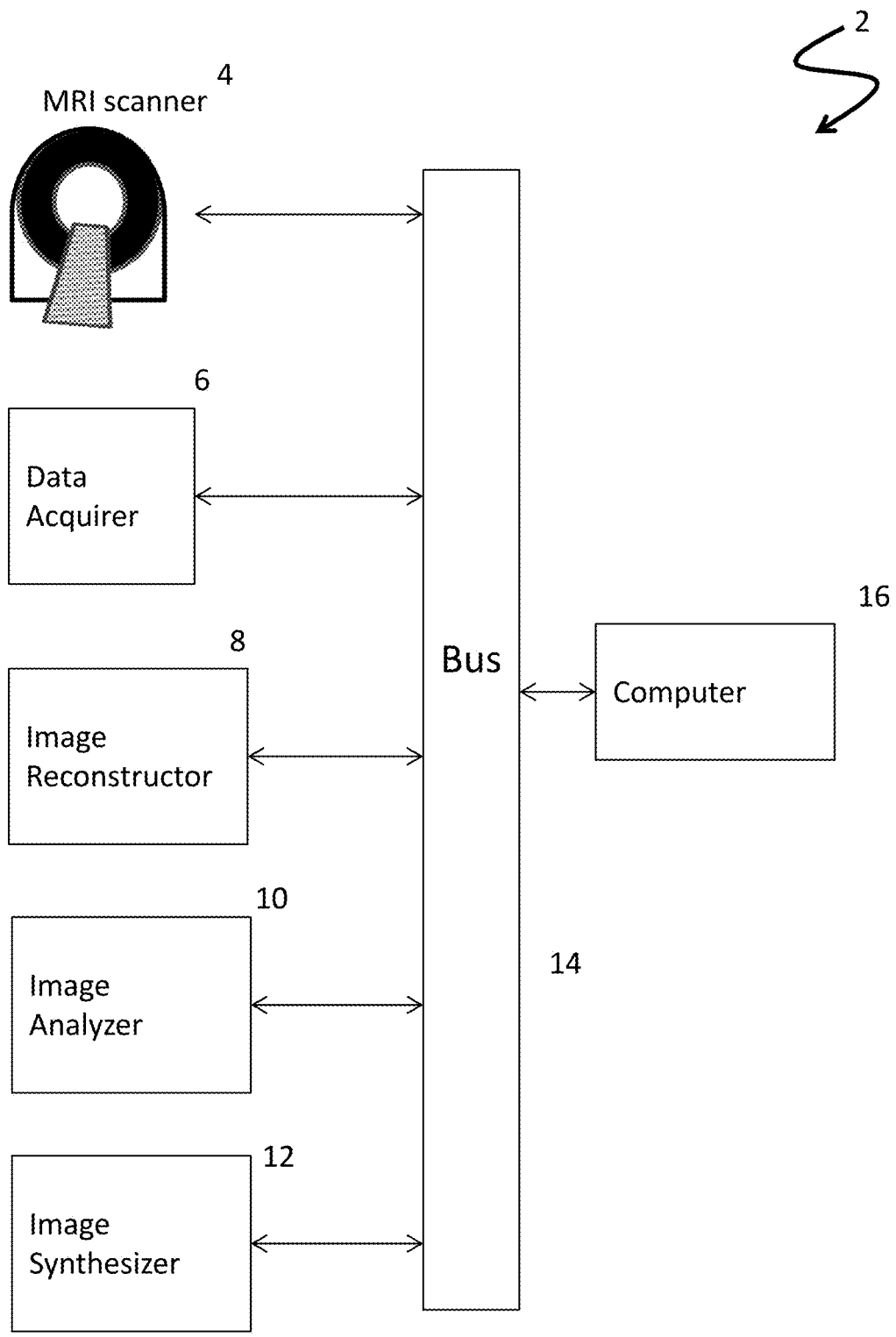
FIG. 1 shows a schematic of a contrast-agent-free (CA-free) medical imaging system.

FIG. 1 shows am example of a computer implemented imaging system 2, incorporating a MR scanner 4. The MR scanner 4 typically comprises a static field magnet, a gradient coil, and a radio frequency (RF) coil disposed in a cylindrical housing of a gantry and an adjustable, often motorized, support or table for maintaining a subject in a desired position (for example, a prone or supine position) in an open central chamber or bore formed in the gantry during a scan procedure.

The static field magnet of the gantry is typically substantially in cylindrical form, and generates a static magnetic field inside the open central chamber of the gantry which is an imaging region of a subject (patient) using electric current provided from a static magnetic field power source in an excitation mode. The gradient coil is also typically substantially in cylindrical form, and located interior to the static field magnet. The gradient coil applies gradient magnetic fields to the subject in the respective directions of the X axis, the Y axis and the Z axis, by using the electric currents supplied from the gradient magnetic field power sources. The RF coil transmits RF pulses toward the subject and receives MR signals as RF radiation emitted from the subject due to nuclear spin excitation and relaxation. RF pulse transmission includes an RF pulse synthesizer and pulse amplifier communicative with an RF coil, while MR signal reception includes an RF coil communicative with a signal amplifier and signal processor. One or more RF coils may be used for RF pulse transmission and MR signal reception, such that the RF coil for RF pulse transmission and MR signal reception may be the same or different. The static field magnet, the gradient coil and the RF coil are driven by one or more controllers.

Directed by a data acquisition scheme, the one or more controllers coordinate a scan of the subject by driving gradient magnetic fields, RF pulse transmission and MR signal reception, and then communicating the received scan data to a data acquisition component 6.

The data acquisition component 6 incorporates a data acquisition scheme or data acquisition computer code that receives, organizes and stores MR scan data from the RF coil/controller of the MR scanner. The scan data is sent to an image reconstruction component 8 incorporating an image reconstruction computer code. The scan data can then be processed using the image reconstruction computer code resulting in image data including multiple images of predetermined sampling site(s) of the subject. The image reconstruction computer code can easily be varied to accommodate any available MR imaging technique. The image data can then be processed by a machine learning image synthesis component 10 incorporating image synthesis computer code tasked with processing of image data to generate a CA-free-AI-enhanced image. The image data can be concurrently processed by a machine learning image analysis component 12 incorporating image analysis computer code tasked with processing of image data to generate a diagnostic image analysis, such as a tissue segmentation or a tumour detection. The image synthesis component 10 and image analysis component 12 are communicative to reciprocally guide their respective CA-free-AI-enhanced image synthesis and image analysis tasks, such that a synthesized CA-free-AI-enhanced image or a precursor thereof generated by the image synthesis component 10 is communicated to the image analysis component 12 to guide the diagnostic image analysis task, and conversely a diagnostic image result or precursor thereof generated by image analysis component 12 is communicated to the image synthesis component 10 to guide the image synthesis task.

The imaging system 2 is controlled by one or more computers 16 with data and operational commands communicated through bus 14. The imaging system 2 may include any additional component as desired for CA-free-AI-enhanced image synthesis and image analysis including multiplexers, digital/analog conversion boards, microcontrollers, physical computer interface devices, input/output devices, display devices, data storage devices and the like. The imaging system 2 may include controllers dedicated to different components of the MR scanner 4, such as a sequence controller to provide power and timing signals to control the gradient coil magnetic field, RF pulse transmission and/or MR signal reception, or such as a table controller to provide power and timing signals to a table motor to control table position and thereby control position of a subject in the gantry by moving the subject along a z-axis through an opening of the gantry communicative with the interior open chamber of the gantry.

FIG. 2 shows a computer implemented method 20 for contrast agent-free medical imaging. The method 20 comprises a pre-scan preparation 30 and positioning of a subject for MR scanning of a desired sampling site or anatomical region of interest. Once the subject is prepared and positioned within a MR scanner, MR scanning 40 is performed to acquire scan data at the sampling site. The scan data is processed to reconstruct 50 image data from the scan data. The image data is then concurrently processed in an image synthesis task 60 and a diagnostic image analysis task 70. The image synthesis task and the image analysis task reciprocally communicate for mutual dependent training of both tasks.

The contrast agent-free medical imaging system and method have been validated by experimental testing. Experimental testing results demonstrate the ability of the contrast agent-free medical imaging system and method to concurrently provide CA-free-AI-enhanced image synthesis and diagnostic image analysis. The following experimental examples are for illustration purposes only and are not intended to be a limiting description.

Experimental Example 1

The details of Experimental Example 1 are extracted from a prior scientific publication (Xu et al., (2020) "Contrast agent-free synthesis and segmentation of ischemic heart disease images using progressive sequential causal GANs", Medical Image Analysis, Vol. 62: article 101668), and this scientific publication is incorporated herein by reference in its entirety. In the event of inconsistency between the incorporated material and the express disclosure of the current document, the incorporated material should be considered supplementary to that of the current document; for irreconcilable inconsistencies, the current document controls.

In this Experimental Example 1, a CA-free image is an image that is synthesized from image data acquired in absence of contrast agent (CA) administration by a machine learning model to achieve an imaging equivalent to CA-enhanced imaging for purposes of a concurrent diagnostic image analysis by the machine learning model achieving diagnostic results comparable to human expert diagnosis using CA-enhanced imaging. Therefore, in Experimental Example 1, the term CA-free can be used interchangeably with the term CA-free-AI-enhanced (or contrast-agent-free-artificial-intelligence-enhanced); for example the term CA-free image can be used interchangeably with the term CA-free-AI-enhanced image.

Figure 3A:
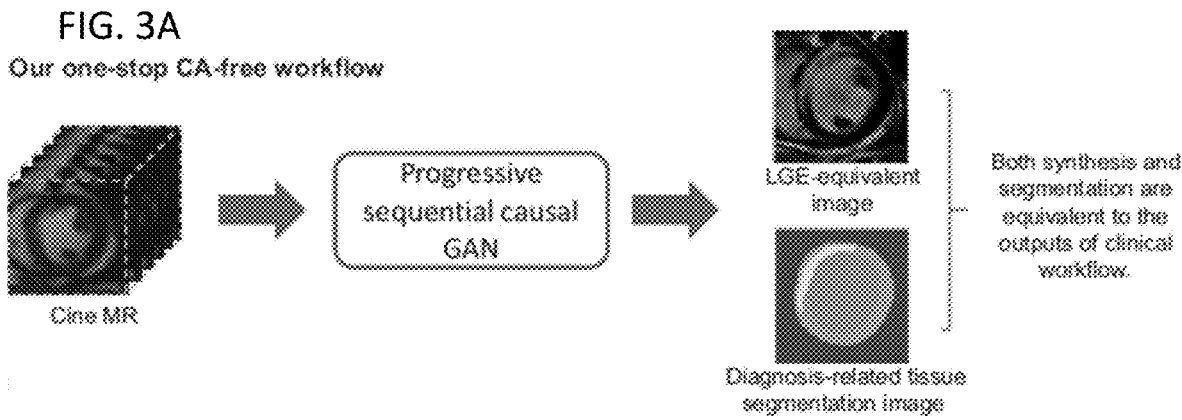
FIGS. 3A-3C show schematic advantages of the present CA-free medical imaging technology (FIG. 3A) compared to existing deep learning-based methods (FIG. 3B) and existing clinical CA-based imaging and manual segmentation by medical experts (FIG. 3C).
Figure 3B:
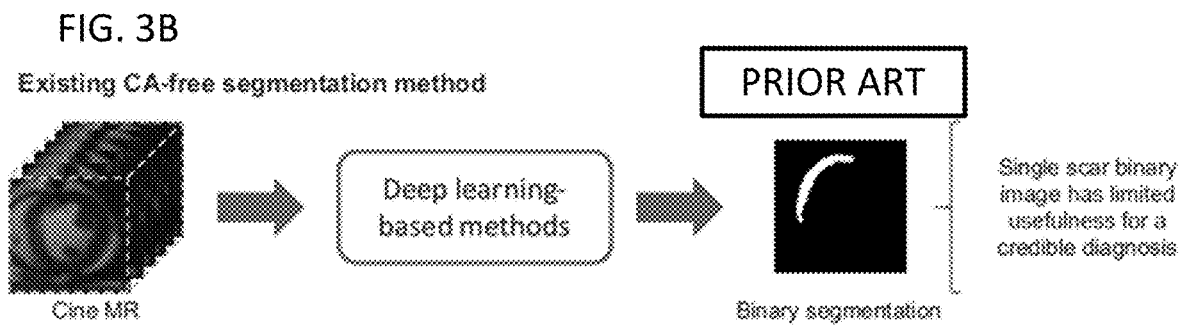
Figure 3C:
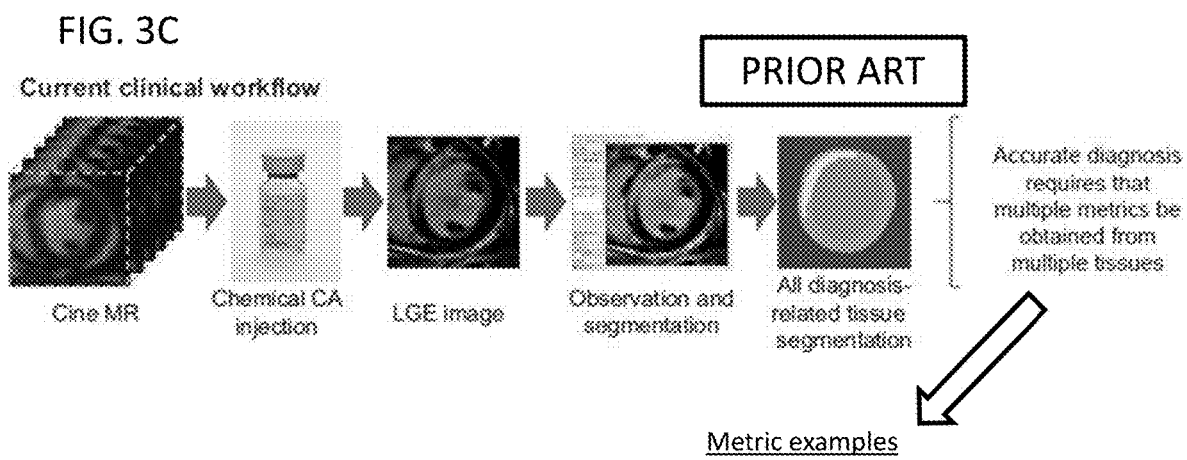

Current state-of-the-art CA-free segmentation methods only produce a binary scar image that fails to provide a credible diagnosis (Xu et al., 2018a; 2018b). As shown in FIG. 3B, this binary scar image can only indicate two categories of pixels: scar and background. This limited resolution thus fails to highlight several relevant tissues (e.g., myocardium and healthy myocardium, blood pool) recommended according to the clinical protocols of comprehensive IHD evaluation. Subsequently, it fails to help radiologists quantitatively assess multiple tissues to obtain the most powerful metrics for a credible IHD diagnosis (for example as shown in FIG. 3C, scar ratio=size of the scar/size of the myocardium). Because the use of multiple metrics based on multiple tissues results in far greater accuracy than using only a metric based on scar tissue alone in a credible IHD diagnosis, the limitations of existing segmentation methods need to be addressed. Thus, clinicians desire development of more advanced CA-free technology that can produce an LGE-equivalent image (i.e., an image that is equivalent to an LGE image in terms of usefulness in an IHD diagnosis or from which clinical metrics can be obtained without CA injections) and a segmented image (including diagnosis-related tissues, i.e., scar, healthy myocardium, and blood pools, as well as other pixels) (Leiner, 2019).

However, it is very challenging to synthesize an LGE-equivalent image and accurately segment diagnosis-related tissues (i.e., scar, healthy myocardium and blood pools) from 2D+T cine MR images. The pixel-level understanding of LGE images by representation learning of the 2D+T cine MR images faces numerous challenges. The differences in the enhancement effects of the CAs on different cardiac cells result in each of the numerous pixels of the LGE image requiring a definite non-linear mapping from the cine MR images. Representation learning of the 2D+T cine MR has a number of high-complexity issues. The time series characteristics of 2D+T cine MR images result in each non-linear mapping requiring a complex mixing of the spatial and temporal dependencies of a mass of pixels in the images, especially since these pixels often have high local variations. More importantly, a pixel-level understanding of LGE images is needed to differentiate between pixels that have very similar appearances (Xu et al., 2017). The highly similar intensity of pixels within the tissue on an LGE image often results in high similarities between the learned spatial and temporal dependencies of these pixels and often causes interference and inaccuracy during mixing.

Existing CA-free automated IHD-diagnosing methods are inefficient in the representation learning of cine MR images, as they must contend with a fixed local observation in both spatial dependency and temporal dependency extraction (e.g., only adjacent temporal frames of optical flow and a fixed spatial convolutional kernel size for deep learning). However, pixels in 2D+T cine MR images often have high local variations (i.e., different positions and motion ranges in different regions and timestamps). Furthermore, current spatial-temporal feature learning methods still struggle with constant learning weights during the mixing of spatial dependencies with temporal dependencies (e.g., both 3DConv and ConvLSTM often simply treat the two dependencies on each pixel as equal during learning) (Xu et al., 2017). However, different pixels have different selection requirements in terms of temporal dependencies and spatial dependencies.

Existing progressive networks. Recently, progressive generative adversarial networks (GAN) have shown great potential in the tasks of image synthesis and segmentation (Huang et al., 2017; Karras et al., 2017; Zhang et al., 2018b). Progressive GAN inherit the advantage of adversarial semi-supervised learning from GAN to effectively learn to map from a latent space to a data distribution of interest. More importantly, the progressive framework of such progressive GAN stacks multiple sub-GAN networks as different phases to take advantage of the result of the previous phase to guide the performance of the next phase and greatly stabilize training. However, current progressive GAN are designed to train on a single task because they lack a two-task generation scheme to handle the synthesis task and segmentation task.

Existing generative adversarial networks (GANs). GANs (Goodfellow et al., 2014) have become one of the most promising deep learning architectures for either image segmentation tasks or synthesis tasks in recent years but may face inefficient and unstable results when two or more tasks must be solved. GAN comprises two networks, a generator and a discriminator, where one is pitted against the other. The generator network learns to map from a latent space to a data distribution of interest, while the discriminative network distinguishes candidates produced by the generator from the true data distribution. However, a GAN may learn an erroneous data distribution or a gradient explosion when the latent space of the distributions of two tasks interfere with each other. Conditional GAN, a type of GAN implementation, has the potential to learn reciprocal commonalities of the two tasks to avoid interference with each other because of its considerable flexibility in how two hidden representations are composed (Mirza and Osindero, 2014). In conditional GAN, a conditioned parameter y is added to the generator to generate the corresponding data using the following equation:

$$\min_G \max_D V(D, G) = \qquad (1)$$
$$\mathbb{E}_{x \sim p_{data}(x)}[\log D(x \mid y)] + \mathbb{E}_{z \sim p_z(z)}[\log(1 - D(G(z \mid y)))]$$

where
$p_{data}(x)$ represents the distribution of the real data; and
$p_z$ represents the distribution of the generator.

Existing attention model. An attention model successfully weighs the positions that are highly related to the task, thereby improving the performance of the application in various tasks (Vaswani et al., 2017). It is inspired from the way humans observe images, wherein more attention is paid to a key part of the image in addition to understanding an image as a whole. Such a model uses convolutional neural networks as basic building blocks and calculates long-range representations that respond to all positions in the input and output images. It then determines the key parts that have high responses in the long-range representations and weights these parts to motivate the networks to better learn the images. Recent work on attention models embedded an auto regressive model to achieve image synthesis and segmentation by calculating the response at a position in a sequence through attention to all positions within the same sequence (Zhang et al., 2018a). This model has also been integrated into GANs by attending to internal model states to efficiently find global, long-range dependencies within the internal representations of the images. The attention model has been formalized as a non-local operation to model the spatial-temporal dependencies in video sequences (Wang et al., 2018). Despite this progress, the attention model has not yet been explored for the internal effects of different spatial and temporal combinations on synthesis and segmentation in the context of GANs.

A novel progressive sequential causal GAN. A novel progressive sequential causal GAN (PSCGAN) described herein, provides a CA-free technology capable of both synthesizing an LGE equivalent image and segmenting a diagnosis-related tissue segmentation image (for example, scar, healthy myocardium, and blood pools, as well as other pixels) from cine MR images to diagnose IHD. As shown schematically in FIG. 3A, this is the first technology to synthesize an image equivalent to a CA-based LGE-image and to segment multiple tissues equivalently to the manual segmentation performed by experts. A further advantage of the described technology is that it is capable of performing concurrent or simultaneous synthesis and segmentation.

PSCGAN builds three phases in a step-by-step cascade of three independent GANs (i.e., priori generation GAN, conditional synthesis GAN, and enhanced segmentation GAN). The first phase uses the priori generation GAN to train the network on a coarse tissue mask; the second phase uses the conditional synthesis GAN to synthesize the LGE-equivalent image; and the third phase uses the enhanced segmentation GAN to segment the diagnosis related tissue image. The PSCGAN creates a pipeline to leverage the commonalities between the synthesis task and the segmentation task, which takes pixel categories and distributions in the coarse tissues mask as a priori condition to guide the LGE-equivalent image synthesis and the fine texture in the LGE-equivalent image as a priori condition to guide the diagnosis-related tissue segmentation. PSCGAN use these two reciprocal guidances between the two tasks to gain an unprecedentedly high performance in both tasks while performing stable training.

The PSCGAN further includes the following novel features: (1) a novel sequential causal learning network (SCLN) and (2) the adoption of two specially designed loss terms. First, the SCLN creatively builds a two-stream dependency-extraction pathway and a multi-attention weighing unit. The two-stream pathway multi-scale extracts the spatial and temporal dependencies separately in the spatiotemporal representation of the images to include short-range to long-range scale variants; the multi-attention weighing unit computes the responses within and between spatial and temporal dependencies at task output as a weight and mixes them according to assigned weights. This network also integrates with GAN architecture to further facilitate the learning of interest dependencies of the latent space of cine MR images in all phases. Second, the two specially designed loss terms are a synthetic regularization loss term and a self-supervised segmentation auxiliary loss term for optimizing the synthesis task and the segmentation task, respectively. The synthetic regularization loss term uses a spare regularization learned from the group relationship between the intensity of the pixels to avoid noise during synthesis, thereby improving the quality of the synthesized image, while the self-supervised segmentation auxiliary loss term uses the number of pixels in each tissue as a compensate output rather than only the shape of the tissues to improve the discrimination performance of the segmented image and thereby improve segmentation accuracy.

Figure 4:
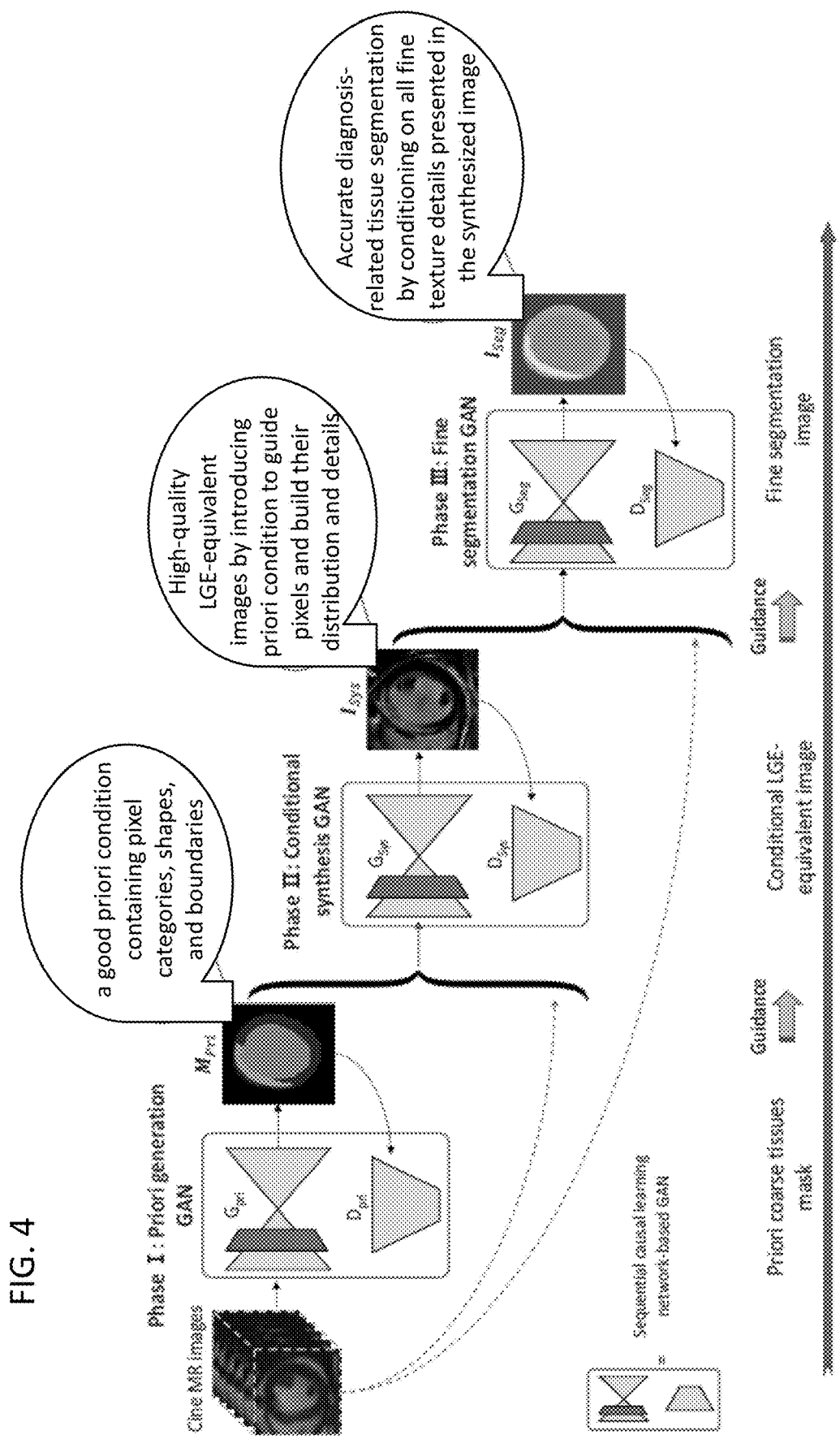
FIG. 4 shows a schematic of a variant of the present CA-free medical technology formed as a progressive sequential causal GAN (PSCGAN) framework.

Overview of PSCGAN. As depicted in FIG. 4, PSCGAN cascades three GANs to build three phases and connect them by taking the output of the previous GAN as an input of the next GAN. Moreover, to reduce the randomness during training, all three GANs encode the cine MR images by using the same foundational network architecture, a SCLN-based GAN that includes an encoder-decoder generator and a discriminator to specially design and handle time-series images. Thus, PSCGAN not only have great training stability by using divide-and-conquer to separate the segmentation task and synthesis task into different phases but also undergo effective training by progressively taking the output of the previous phase as the priori condition input to guide the next phase.

Phase I: priori generation GAN. This phase uses the priori generation GAN (Pri) to generate a coarse tissue mask ($M_{pri}$) from the cine MR images X by adversarial training. This coarse segmented image is a rich priori condition, as it contains all pixel categories and tissue shapes, locations, and boundaries.

Phase II: conditional synthesis GAN. This phase uses the conditional synthesis GAN (Sys) to integrate the coarse tissue mask and the cine MR image to build a conditional joint mapping to use the obtained pixel attributes and distributions from the mask to guide image synthesis for generating a high-quality LGE-equivalent image ($I_{sys}$).

Phase III: enhanced segmentation GAN. This phase uses the enhanced segmentation GAN (Seg) to introduce the synthesized image from Sys as a priori condition to generate the diagnosis-related tissue segmentation image $I_{Seg}$. The synthesized image and all detailed textures effectively guide the classification of the tissue boundary pixels.

A component of the PSCGAN is a novel SCLN. SCLN improves the accuracy of time-series image representations by task-specific dependence selecting between and within extracted spatial and temporal dependencies. By integrating SCLN into the GAN architecture as the encoder of cine MR images in the generator, the SCLN-based GAN improves the learning effectiveness of the interest distribution from the latent space of cine MR images, thereby effectively improving the generating performance on adversarial training.

Sequential causal learning network (SCLN). The SCLN uses a two-stream structure that includes a spatial perceptual pathway, a temporal perceptual pathway and a multi-attention weighing unit. This network gains diverse and accurate spatial and temporal dependencies for improving the representation of the time-series images. In addition, this is a general layer that can be used individually or stacked flexibly as the first or any other layer.

Figure 5:
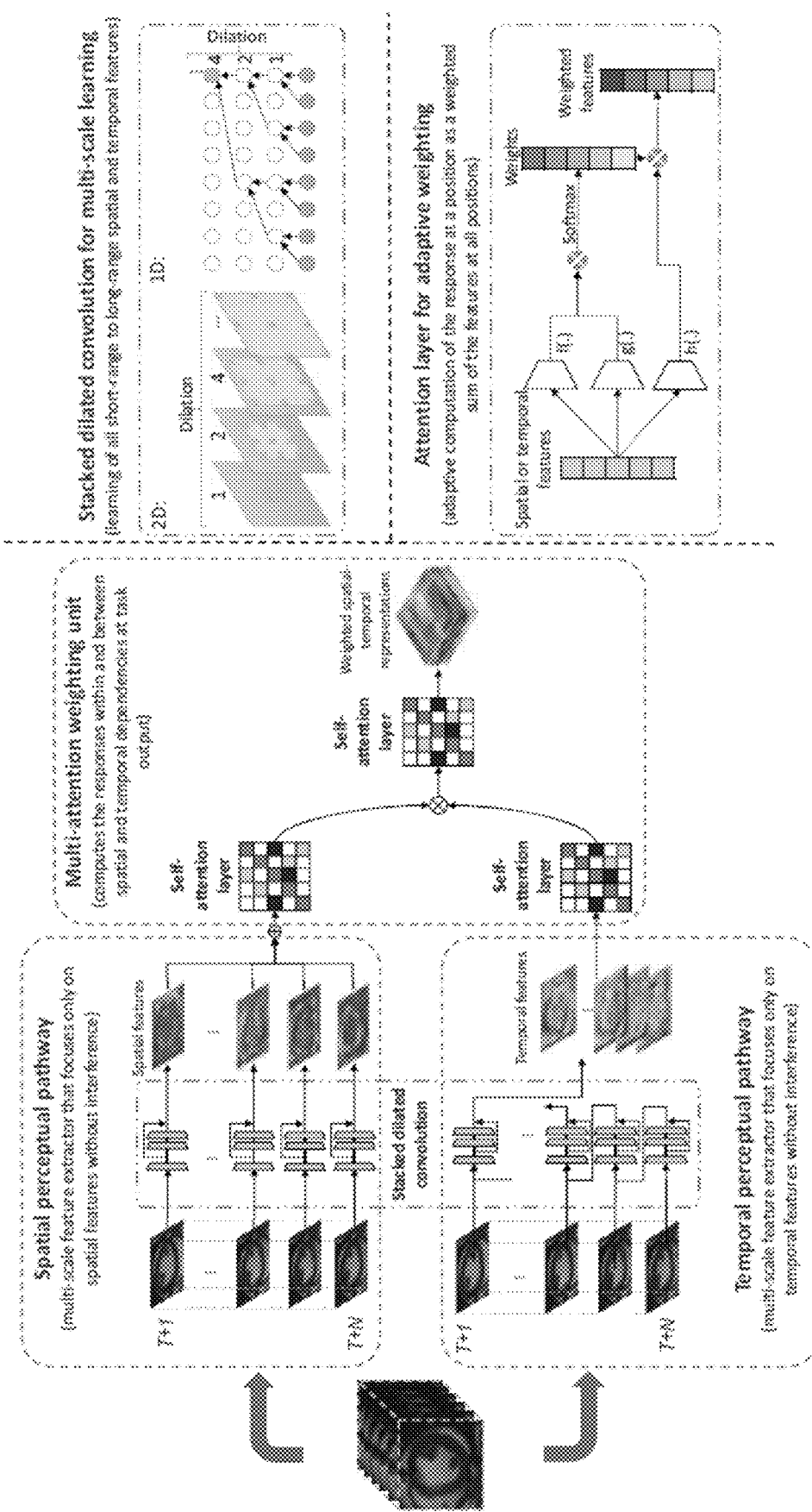
FIG. 5 shows a schematic of a sequential causal learning network (SCLN) component integrated within the PSCGAN framework shown in FIG. 4.

Two-stream structure for multi-scale spatial and temporal dependency extraction. As shown in FIG. 5, a two-stream structure, which includes a spatial perceptual pathway and a temporal perceptual pathway, correspondingly match the two-aspect dependencies in the time-series image. It uses two independent, stacked dilated convolutions as multi-scale extractors to respectively focus the spatial dependencies and the temporal dependencies in the time-series images. Dilated convolution includes sparse filters that use skip points during convolution to exponentially grow the receptive field to aggregate multi-scale context information. It improves the diversity of both spatial dependencies and temporal dependencies to include all short-range to long-range scale variants. The 1D/2D dilated convolutions are formulated as:

$$1D: (\text{kernel} *_l x)_t = \sum_{s=-\infty}^{\infty} \text{kernel}_s \cdot f_{t-ls} \quad (2)$$

$$2D: (x *_l \text{kernel})(p) = \sum_{s+lt=p} x(s)\text{kernel}(t) \quad (3)$$

where x is the 1D/2D signal/image, and/is the dilation rater.

The spatial perceptual pathway uses 2D dilated convolution, and the temporal perceptual pathway uses 1D dilated convolution. The inputs of both pathways are cine MR images. The spatial perceptual pathway regards 2D+T cine MR images as multiple (time t to time t+n) independent 2D images. Each input image is learned by a 2D dilated convolution, where the number of 2D dilated convolution is the same as the number of frames. The output of the 2D dilated convolution in time t is the spatial feature convolved with the frame of time t only. Thus, the spatial feature of 2D+T cine MR images can be effectively captured when combining all 2D dilated convolution from time t to time t+n. By contrast, the spatial perceptual pathway regards 2D+T cine MR images as a whole 1D data. This 1D data is learned by 1D dilated convolutions according to its order, where the hidden units of the 1D dilated convolution that are the same length as the 1D form of each frame (the length of a 64×64 frame is 4096). The output of each 1D dilated convolution time t is the temporal feature convolved with the frame of time t and the earlier time in the previous layer. Thus, the temporal feature of 2D+T cine MR can be effectively captured when the 1D dilated convolution process reaches the time t+n.

In this experimental example, both pathways initially stack 6 dilated convolutions, and the corresponding dilation rate is [1, 1, 2, 4, 6, 8]. This setting allows the learned representation to include all 3×3 to 65×65 motion and deformation scales. Note that the stack number still varies with the spatial and temporal resolution of the time-series image during encoding. Moreover, both spatial and temporal perceptual pathways stack 3 stacked dilated convolutions (1D/2D) again to build a residual block framework for deepening the network layers and enriching hierarchical features. In this experimental example, both paths also adopt a causal padding to ensure that the output at time t is only based on the convolution operation at the previous time. This causal-based convolution means that there is no information leakage from the future to the past. Advantages of this two-stream structure include: 1) two pathways used to focus on two aspect dependencies independently; 2) dilated convolution with residual blocks and shortcut connections used to extract multiscale and multilevel dependencies and 3) causal padding used to understand the time order within the dependencies.

Multi-attention weighing unit for task-specific dependence selection. As shown in FIG. 5, the multi-attention weighing unit includes three independent self-attention layers and an add operator to adaptively weigh the high-contribution dependences between and within spatial and temporal dependencies at the output to perform accurate task-specific dependence selection (Vaswani et al., 2017). Two self-attention layers first embed behind both the spatial perceptual pathway and the temporal perceptual pathway to adaptively compute the response of each pathway's dependence at the output as their weights; then, the add operator element-wise fuses the weighed spatial and temporal dependencies; finally, the third self-attention layer determines which of the fused spatial-temporal dependences is the task-specific dependence. The spatial dependencies from the spatial perceptual pathway are defined as $$\mathcal{F}_{S_{Conv}} \in R^{C \times N}$$

where:
C is the number of channels; and
N is the number of dependencies.

The spatial self-attention layer first maps these spatial dependencies into two feature spaces:

$$f(\cdot) = W_f \mathcal{F}_{S_{Conv}} \text{ and } g(\cdot) = W_g \mathcal{F}_{S_{Conv}}.$$

It calculates the weight $\alpha_i$ to the ith dependencies, where $$\alpha = (\alpha_1, \alpha_2, \ldots, \alpha_j, \ldots, \alpha_N) \in R^{C \times N}:$$

$$\alpha_i = \frac{\exp(s_i)}{\sum_{i=1}^{N} \exp(s_i)}, \text{ where } s_i = f(\mathcal{F}_{S_{Conv\ i}})^T g(\mathcal{F}_{S_{Conv\ i}}) \quad (4)$$

The weighed spatial dependencies $\alpha \mathcal{F} S_{Conv}$ are as follows:

$$v\left(\sum_{i=1}^{N} \alpha_i h(\mathcal{F}_{S_{Conv\ i}})\right), \quad (5)$$

$$h(\mathcal{F}_{S_{Conv\ i}}) = W_h \mathcal{F}_{S_{Conv\ i}}, v(\mathcal{F}_{S_{Conv\ i}}) = W_v \mathcal{F}_{S_{Conv\ i}} \quad (6)$$

where $W_g$, $W_f$, $W_h$, $W_v$ are the learned weight matrices. For memory efficiency, $\{W_g, W_f, W_h, W_v\} \in \mathbb{R}^{\tilde{C} \times C}$, where $\tilde{C}$ is the reduced channel number; and $\tilde{C} = C/8$.
Note that 8 is a hyperparameter.

By the same token, the temporal self-attention layer enhances the temporal dependencies $\mathcal{F} T_{Conv}$ from the temporal perceptual path to an attention-weighted $$\beta \mathcal{F} T_{Conv} \in R^{C \times N}, \text{ where}$$

$$\beta = (\beta_1, \beta_2, \ldots, \beta_j, \ldots, \beta_N) \in R^{C \times N} \text{ are the weights of the temporal dependencies.}$$

The add operator elementwise fuses the weighed spatial dependencies and temporal dependencies:

$$\mathcal{F} ST_{Conv} = \alpha \mathcal{F} S_{Conv} + \beta \mathcal{F} T_{Conv} \quad (7)$$

The fused self-attention layer weighs the fused spatial-temporal dependencies: $\mathcal{F} ST_{Conv}$.
The output of this layer is $^O ST_{Conv} \in R^{C \times N}$.
This output further adds the input of the map layer after modification with a learnable scalar ($\gamma$).
Therefore, the final output is given by $\gamma ^O St_{Conv} + \mathcal{F} ST_{Conv}$.

Figure 6:
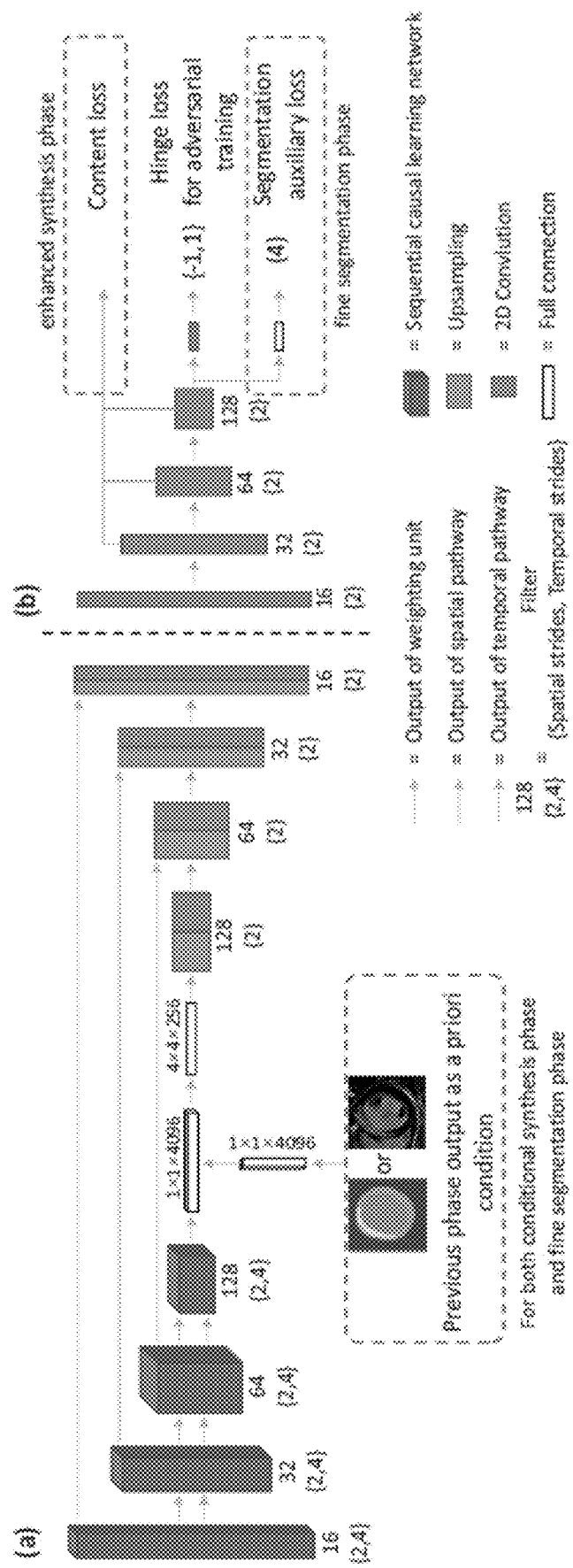
FIG. 6 shows that by integrating SCLN into the GAN architecture as the encoder of cine MR images in the generator, the SCLN-based GAN improves the learning effectiveness of interest distribution from the latent space of cine MR images, thereby effectively improving the generating.

Implementation of an SCLN-based GAN for the basic network architecture. This network stacks 4 SCLNs and 4 corresponding up-sampling blocks to build a generator. The network further stacks 5 convolutional layers to build a discriminator. Both the generator and discriminator use conditional adversarial training to effectively perform the segmentation and synthesis. As shown in FIG. 6, the generator is an encode-decode 2D+T to 2D framework modified from U-Net (Ronneberger, O., Fischer, P., Brox, T., 2015. U-net: Convolutional networks for biomedical image segmentation, in: International Conference on Medical image computing and computer-assisted intervention, Springer. pp. 234-241). It first encodes the input $X \in R^{25 \times 64 \times 64 \times 1}$ (25 frames, image size per frame 64×64×1) by using 4 SCLNs with 2, 2, 2, 2 strides on the spatial perceptual pathway and 4, 4, 4, 4 strides on the temporal perceptual pathway. The first SLCN uses two copies of X as the inputs into its spatial perceptual pathway and temporal perceptual pathway. Thus, beginning from the second SCLN, the generator takes the spatial and temporal perceptual pathway outputs of the previous SCLN as the input and encodes a 25×4×4×128 feature from the multi-attention weighing unit output of the fourth SCLN. Then, this encoded feature is further reduced to 1×1×4096 by a fully connected layer and is then passed to another fully connected layer to reshape the encoded feature into a 4×4×256 feature. Four upsampling blocks (Upsampling-Conv2D-LN) then use this reshaped feature to encode an image (i.e., the coarse tissue mask, the LGE-equivalent image or the diagnosis-related tissue segmentation image)$\in R^{64 \times 64 \times 1}$. Moreover, the generator also uses a dot layer to reduce the first dimension of the multi-attention weighing unit output from the first to the third SCLN and a skip connection that is the same as the U-Net to feed the corresponding upsampling block with the same feature map size.

The discriminator encodes the output of the generator of the corresponding phase and determines whether this output is consistent with the domain of its ground truth. All 5 convolutional layers have strides of 2. Note that the attention layer is added between the second convolutional layer and the third convolutional layer. These attention layers endow the discriminator with the ability to verify that highly detailed features in distant portions of the image are consistent with each other and to improve the discrimination performance.

An advantage of this SCLN-based GAN is an accurate encoding of interest dependencies from the latent space of cine MR image.

Figure 7:
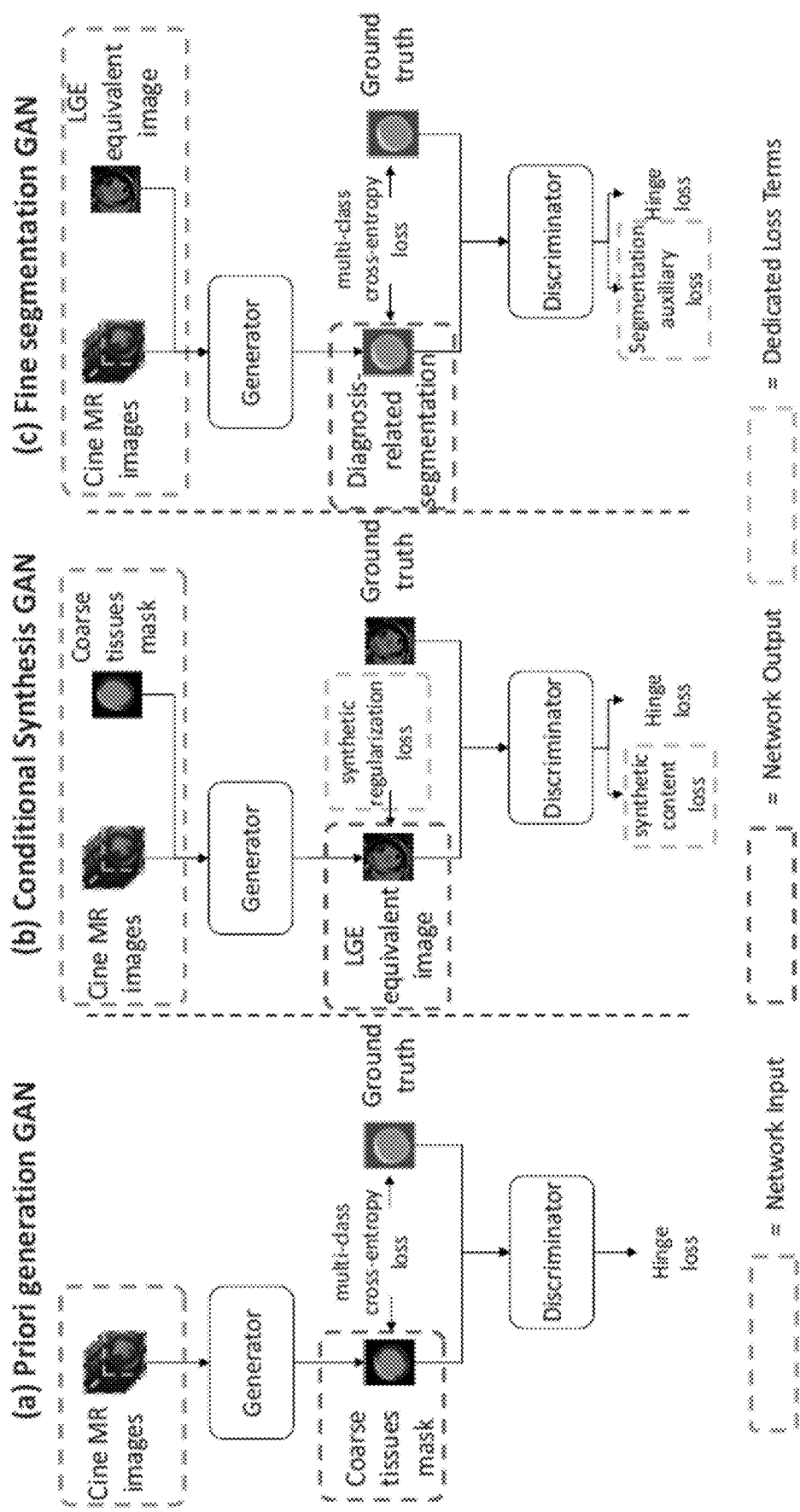
FIG. 7 shows a schematic of data flow within the PSCGAN framework and three linked GANs executing three progressive phases of PSCGAN—priori generation GAN (panel a), conditional synthesis GAN (panel b), and segmentation GAN (panel c). GANs in the three phases leverage adversarial training and dedicated loss terms to enhance the performance of image synthesis and segmentation tasks. The conditional synthesis GAN and segmentation GAN leverage the output of the respective previous GANs to guide the training of the next GAN as part of its input.

Phase I: priori generation GAN for coarse tissue mask generation. The priori generation GAN (Pri) is built with the same architecture as the SCLN-based GAN, as shown in FIG. 7 (part a). It includes a generator $G_{Pri}$ and a discriminator $D_{Pri}$. This GAN generates a coarse tissue mask $M_{Pri}$, which focuses on drawing the shape, contour and correct categories for four classifications (scar, healthy myocardium, blood pool, and other pixels). This GAN does not seek a final result in one step but takes advantage of the shape, contour, and categories of this rough segmentation as a priori information to guide the next module to learn the attributes and distributions of the pixels. Training of this generator uses multi-class cross-entropy loss. Although $M_{Pri}$ contains four classes, the generator is treated as a single classification problem for the samples in one of these classes by encoding both the generator output and ground truth to one-hot vector classes. The generator can be formulated as follows:

$$\mathcal{L}_{G_{Pri}} = \sum_{n=1}^{N} mce(G_{Pri}(X), \tilde{I}_{Seg}) \tag{8}$$

$$mce = -\frac{1}{N}\sum_{n=1}^{N} \left[\tilde{I}_{Seg} \log M_{Pri} + (1 - \tilde{I}_{Seg}) \log(1 - M_{Pri})\right] \tag{9}$$

where
$\tilde{I}_{Seg}$ is the ground truth of $M_{Pri}$, and N=4.

The discriminator training uses the adversarial loss $\mathcal{L}_{Adv}^{Pri}$, which adopts the recently developed hinge adversarial loss (Vaswani, A., Shazeer, N., Parmar, N., Uszkoreit, J., Jones, L., Gomez, A. N., Kaiser, Ł., Polosukhin, I., 2017. Attention is all you need, in: Advances in Neural Information Processing Systems, pp. 5998-6008). This hinge adversarial loss maps the true sample to a range greater than 1 and maps the false sample to an interval less than −1. It better converges to the Nash equilibrium between the discriminator and generator, thus resulting in less mode collapsing and more stable training performance than other GAN losses. It can be formulated as follows:

$$\mathcal{L}_{Adv}^{D_{Pri}} = -\mathbb{E}_{(\tilde{I}_{Seg}) \sim p_{data}}[\min(0, -1 + D_{Pri}(\tilde{I}_{Seg}))]$$
$$-\mathbb{E}_{X \sim p_X}[\min(0, -1 - D_{Pri}(G_{Pri}(X)))]$$

$$L_{Adv}^{G_{Pri}} = -\mathbb{E}_{X \sim p_X} D_{Pri}(G_{Pri})) \tag{10}$$

Phase II: conditional synthesis GAN for high-quality LGE-equivalent image synthesis. The conditional synthesis GAN (Sys) includes a generator $G_{Sys}$ and a discriminator $D_{Sys}$ to generate an LGE-equivalent image $I_{Sys}$. As shown in FIG. 7 (part b), this GAN introduces the previously generated course tissue mask to guide the network training by modifying the SCLN-based GAN with a fully connected layer in the generator to concatenate the 1×1×4096 feature and the mask, the output of which is then fed into the following fully connected layer and 4 upsampling blocks. Thus, this GAN builds a conditional joint mapping space between the segmentation and the synthesis to use the basic attributes and distributions (i.e., shape, contour, location, and categories) of the tissues to disentangle different tissue-feature learning in the cine MR images and allows the generator to perform accurate and detailed synthesis.

The generator uses the synthetic regularization loss $\mathcal{L}G_{Sys}$ for the training. This loss incorporates an L2-regularization term and an overlapping group sparsity anisotropic operator into the recently developed total variation loss to improve the quality of the synthesized image (Pumarola, A., Agudo, A., Martinez, A. M., Sanfeliu, A., Moreno-Noguer, F., 2018. Ganimation: Anatomically-aware facial animation from a single image, in: Proceedings of the European Conference on Computer Vision, pp. 818-833). The total variation loss has recently shown the ability to significantly reduce the noise in the synthesized image during image synthesis. L2-regularization is further incorporated into the total variation loss to measure the computation complexity and prevent overfitting by penalizing this complexity. The overlapping group sparsity anisotropic operator is further incorporated into the total variation loss. It takes into account group sparsity characteristics of image intensity derivatives, thereby avoiding staircase artifacts that erroneously consider smooth regions as piecewise regions. This loss is formulated as follows:

$$\mathcal{L}_{G_{Sys}} = \tag{11}$$
$$\mathbb{E}_{I_{Sys} \sim P_G}\left[\frac{1}{2}\|I_{Sys}\|_2^2 + v\left(\phi(I_{Sys_{i+1,j}} - I_{Sys_{i,j}}) + \phi(I_{Sys_{i,j+1}} - I_{Sys_{i,j}})\right)\right]$$

where i and j are the ith and jth pixel entry of $I_{Sys}$,
$v>0$ is a regularization parameter, and
$\varphi(\cdot)$ is overlapping group sparsity function. Overlapping group sparsity anisotropic operator is described as $$\phi(u) = \sum_{i,j=1}^{n} \|u_{i,j,K}(:)\|_2 \tag{12}$$

$$u_{i,j,K} = \begin{bmatrix} u_{i-m_1,j-m_1} & u_{i-m_1,j-m_1+1} \\ u_{i-m_1+1,j-m_1} & u_{i-m_1+1,j-m_1+1} \end{bmatrix} \tag{13}$$

where K is the group size;

$$m_1 = \left\lfloor \frac{K-1}{2} \right\rfloor; \text{ and}$$

$$m_2 = \left\lfloor \frac{K}{2} \right\rfloor.$$

The discriminator is trained using an adversarial loss term and a synthetic content loss term: 1) the synthesis adversarial loss $\mathcal{L}_{Adv}^{D_{Sys}}$ adopts the hinge adversarial loss and can be formulated as:

$$\mathcal{L}_{Adv}^{D_{Sys}} = -\mathbb{E}_{(\tilde{I}_{Sys}) \sim p_{data}}[\min(0, -1 + D_{Sys}(\tilde{I}_{Sys}))]$$

$$- \mathbb{E}_{X \sim p_X}[\min(0, -1 - D_{Sys}(G_{Sys}(X|M_{Pri})))]$$

$$L_{Adv}^{G_{Sys}} = -\mathbb{E}_{X \sim p_X} D_{Sys}(X|M_{Pri})) \quad (14)$$

where
$\tilde{I}_{Sys}$ is the ground truth (i.e, LGE image);

2) the synthetic content loss $\mathcal{L}_{Cont}^{Sys}$ uses feature maps of the 2nd, 3rd and 4th convolution layers outputted from discriminator to evaluate $I_{Sys}$ by comparing it to its ground truth $\tilde{I}_{Sys}$.

This multiple feature map evaluation allows the discriminator to discriminate the image in terms of both the general detail content and higher detail abstraction during the activation of the deeper layers, thereby improving the discriminator performance. It is defined as follows:

$$\mathbb{E}_{I_{Sys} \sim P_{data}}\left[\frac{1}{W_i H_i} \sum_{x=1}^{W_i} \sum_{y=1}^{H_i} (D_{Sys}^{Conv_i}(\tilde{I}_{Sys})_{x,y} - D_{Sys}^{Conv_i}(G_{Sys}(X|M_{Pri}))_{x,y})^2\right] \quad (15)$$

where:
$D_{Sys}^{Conv_i}$ is the feature map;
and $W_i$ and $H_i$ obtained by the ith convolution layer (after activation).

Advantages of the conditional synthesis GAN include: 1) the coarse tissue mask is used as an a priori condition to guide the accurate synthesis of the tissues, 2) the synthetic regularization loss is used to reduce the image noise during synthesis, and 3) the synthetic content loss is used to improve the detail restoration in the image synthesis.

Phase III: enhanced segmentation GAN for accurate diagnosis-related tissues segmentation. The enhanced segmentation GAN (Seg) includes a generator $G_{Seg}$ and a discriminator $D_{Seg}$ to generate an accurate diagnosis-related tissue segmentation image $I_{Seg}$, as shown in FIG. 7 (part c). Compared to the basic SCLN-based GAN, this GAN has following two differences: 1) it adds a fully connected layer into the generator at the same position as that of the conditional synthesis GAN to introduce the synthesized image output from phase II as a condition to guide the segmentation (the synthesized image already includes all detailed textures of the tissues, which effectively aids the fine classification of the tissue boundary pixels), and 2) it adds a linear layer at the end of the discriminator to regress the size (number of pixels) of the 4 different segmentation categories at the end of the discriminator to perform a self-supervised segmentation auxiliary loss. This self-supervised loss prevents the discriminator from only judging the segmented image based on the segmentation shape, causing the discriminator to extract a compensate feature from the input image to improve its discrimination performance. The generator with multi-class cross-entropy loss and the discriminator with segmentation adversarial loss can be formulated as follows:

$$\mathcal{L}_{G_{Seg}} = \sum_{n=1}^{N} mce(G_{Seg}(X|I_{Sys}), \tilde{I}_{seg}) \quad (16)$$

$$\mathcal{L}_{Adv}^{D_{Seg}} = -\mathbb{E}_{(\tilde{I}_{Seg}) \sim p_{data}}[\min(0, -1 + D_{Seg}(\tilde{I}_{Seg}))] -$$

$$\mathbb{E}_{X \sim p_X}[\min(0, -1 - D_{Seg}(G_{Seg}(X|\tilde{I}_{Sys})))]$$

$$L_{Adv}^{G_{Seg}} = -\mathbb{E}_{X \sim p_X} D_{Seg}(G_{Seg}(X|I_{Sys}))$$

The discriminator with self-supervised segmentation auxiliary loss can be formulated as follows:

$$\mathcal{L}_{Seg}^{Aux} = \mathbb{E}_{\tilde{I}_{seg} \sim P_{data}} \|D_{Seg}^{Aux}(Si|\tilde{I}_{Seg}) - D_{Seg}^{Aux}(Si|G_{Seg}(X|I_{Sys})))\|_1 \quad (17)$$

where
$Si = \sum_{n=1}^{4}(Si_1, Si_2, Si_3, Si_4)$ is the size of the 4 segmentation categories of pixels in the image outputted from the linear layer of the discriminator $D_{Seg}^{Aux}$.

Advantages of the enhanced segmentation GAN include: 1) the boundaries of tissues within synthesized images are used to guide the tissue's boundary segmentation and 2) the self-supervised segmentation auxiliary loss is used to improve the segmentation adversarial.

Materials and implementation for Experimental Example 1.

A total of 280 (230 IHD and 50 normal control) patients with short-axis cine MR images were selected. Cardiac cine MR images were obtained using a 3-T MRI system (Verio, Siemens, Erlangen, Germany). Retrospectively gated balanced steady-state free-precession non-enhanced cardiac cine images with 25 reconstructed phases were acquired (repetition time/echo time, 3.36 msec/1.47 msec; field of view, 286×340 mm$^2$; matrix, 216×256; average temporal resolution, 40 msec). LGE MRI was performed in the same orientations and with the same section thickness using a two-dimensional segmented, fast low-angle shot, phase-sensitive inversion recovery sequence 10 min after intravenous injection of a gadolinium-based contrast agent (Magnevist, 0.2 mmol/kg; Bayer Healthcare, Berlin, Germany). Moreover, a network with heart localization layers, as described in (Xu et al., 2017), was used to automatically crop both cine MR images and LGE images to 64×64 region-of-interest sequences, including the left ventricle. Furthermore, the cropped cine and LGE images were registered at the end-diastole phase.

The ground truth of the LGE-equivalent image is the real LGE images. The ground truth of the diagnosis-related tissue segmentation image is an LGE segmented image that includes the contours of the healthy myocardium, scar, and blood pool. These contours were manually delineated on the LGE MRI by a radiologist (N. Z., with 7 years of experience in cardiovascular MRI) from the LGE image. All manual segmentations were reviewed by another expert (L. X., with 10 years of experience in cardiovascular MRI), and in cases of disagreement, a consensus was reached.

The PSCGAN randomly selected ¾ of the patients for training and the remaining ¼ (70) patients were used for independent testing. All three GANs were trained using an adaptive moment optimization (ADAM) solver with a batch size of 1 and an initial learning rate of 0.001. For every 2 optimization steps of the discriminator, a single optimization step was performed for the generator. Layer normalization and leaky rectified linear unit (LeakyReLU) activation were used both in the generators and the discriminators. The pixel values were normalized to [−1, 1].

The PSCGAN connects three GANs by taking the output of the previous GAN as an input of the next GAN. Each GAN includes a generator and a discriminator. All discriminators are used only during adversarial training.

Priori generation GAN inputs the 2D+T cine MR images $X \in R^{H \times W \times T \times C}$, where H=W=64 are the height and width of each temporal frame, T=25 is a temporal step, C=1 is the number of channels. This GAN outputs coarse tissue masks of 64×64×1. When adversarial training, the generator of this GAN inputs 2D+T cine MR images and outputs coarse tissue masks. The discriminator of this GAN inputs coarse tissue masks and the corresponding ground truth is 64×64×1. This discriminator outputs 1×4 probability values.

Conditional synthesis GAN inputs a combination of coarse tissue masks of 64×64×1 and cine MR images of 25×64×64×1. This GAN outputs LGE-equivalent images of 64×64×1. During the adversarial training, the generator of this GAN inputs a combination of coarse tissue masks, and cine MR images, and outputs LGE-equivalent images. The discriminator of this GAN inputs LGE-equivalent images and the corresponding ground truth of 64×64×1. This discriminator outputs 1×1 probability values.

Enhanced segmentation GAN inputs the combination of LGE-equivalent images of 64×64×1 and cine MR images of 25×64×64×1. This GAN outputs diagnosis-related tissue segmentation images of 64×64×1. During the adversarial training, the generator of this GAN inputs a combination of LGE-equivalent images and cine MR images, and outputs diagnosis-related tissue segmentation images. The discriminator of this GAN inputs LGE-equivalent images and the corresponding ground truth of 64×64×1. This discriminator outputs 1×4 probability values, and 1×4 vectors.

Note that the 64×64×1 coarse tissue masks and segmented images are categorical data, which are quickly converted to and from 64×64×4 one-hot data during adversarial training.

PSCGAN performance is evaluated in two aspects: 1) clinical metrics and 2) imagology metrics. Clinical metrics include the scar size, the segment-level scar localization (16-segment model), the MI ratio (scar pixels/healthy myocardium pixels), and the transmurality. All these metrics compare the results of PSCGAN diagnosis-related tissue segmentation image with the results of the ground truth by using the correlation coefficient, Bland-Altman analysis (Altman and Bland, 1983), sensitivity, specificity and positive and negative predictive values (PPV and NPV). In imagology metrics, PSCGAN segmented image is compared with the ground truth by calculating the accuracy, sensitivity, specificity, and Dice coefficient. The LGE-equivalent image is also compared with the LGE image (ground truth) by calculating the structural similarity index (SSIM), peak signal-to-noise ratio (PSNR), and normalized root-mean-squared error (NRMSE).

Results for Experimental Example 1.

Comprehensive experiments indicated that the PSCGAN synthesizes a high-quality LGE-equivalent image and accurately segments all diagnosis-related tissues. PSCGAN achieved an NRMSE of 0.14 when comparing the LGE-equivalent image to ground truth and achieved 97%, 96%, and 97% segmentation accuracy when comparing the clinicians' manual segmentation of the scar, healthy myocardial tissues, and blood pools, respectively. The correlation coefficient between the scar ratio obtained from PSCGAN and that from the current clinical workflow was 0.96. These results demonstrated that PSCGAN could perform full diagnosis-related tissue observation and segmentation, thereby obtaining highly accurate diagnosis metrics in a real clinic setting.

TABLE 1

PSCGAN achieved accurate diagnosis-related tissues segmentation image and high-quality LGE-equivalent image synthesis in terms of imageology metrics.

| Accurate diagnosis-related tissues segmentation image | | | | |
|---|---|---|---|---|
| | Accuracy | Sensitivity | Specificity | Dice coefficient |
| Overall | 97.17(0.48)% | 91.68% | 98.53% | 0.918(0.17) |
| Scar | 97.13(0.23)% | 90.84% | 98.48% | 0.932(0.11) |
| Healthy myocardium | 96.34(0.51)% | 91.07% | 99.11% | 0.908(0.19) |
| Blood pool | 97.97(0.44)% | 91.84% | 98.36% | 0.936(0.15) |

| High-quality LGE-equivalent image synthesis | | |
|---|---|---|
| SSIM | NRMSE | PSNR |
| 0.78(0.10) | 0.11(0.05) | 23.03(1.42) |

Figure 8:
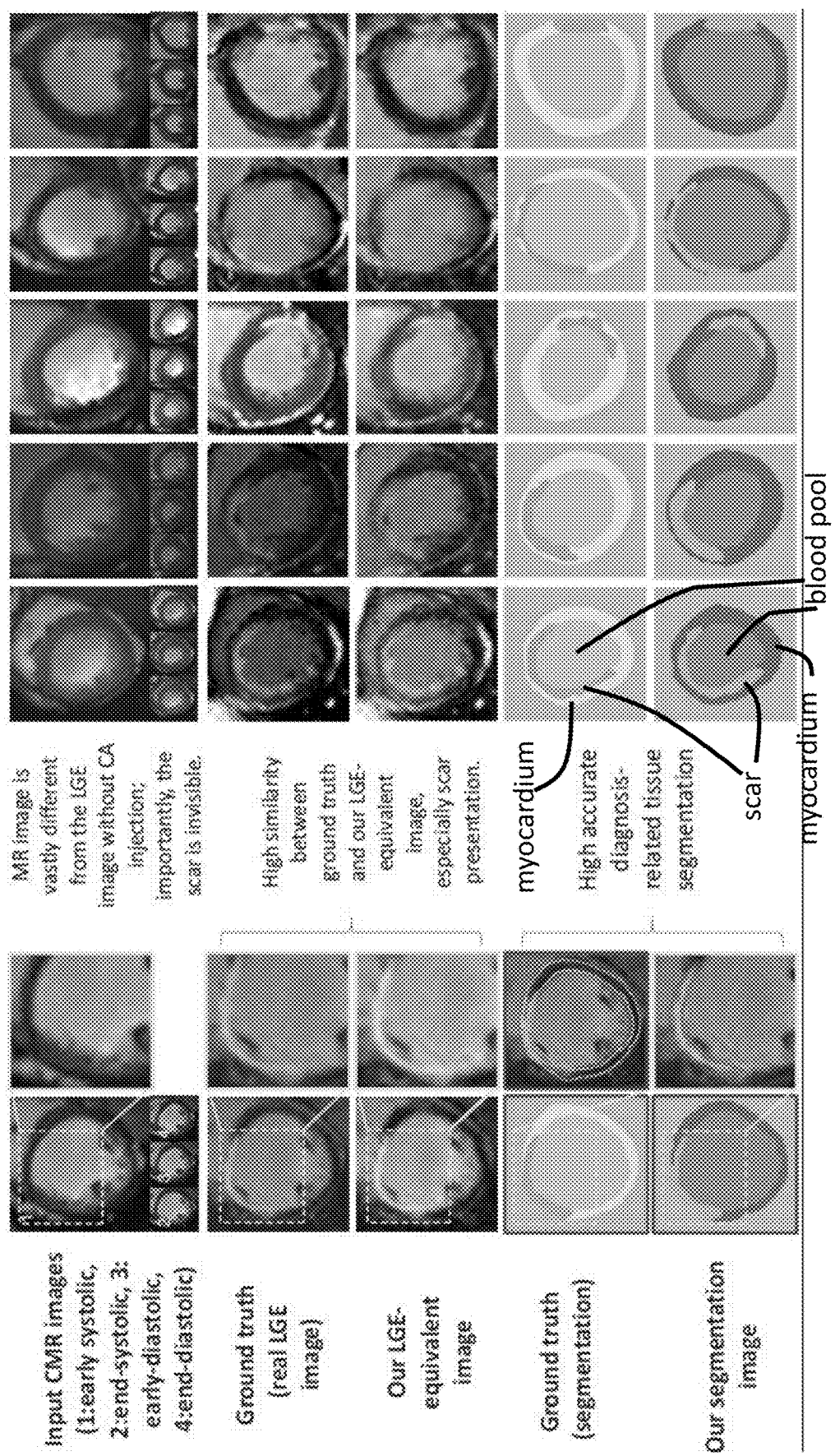
FIG. 8 shows PSCGAN-based synthesis of high-quality late-gadolinium-enhanced-equivalent (LGE-equivalent) images and PSCGAN-based accurate diagnosis-related tissue segmentation images. In LGE-equivalent images, the scar (dashed box, the high contrast area in left ventricle (LV) wall) has a clear and accurate presentation when compared to the real LGE image. This high contrast area is invisible in cine MR images without CA injection. In diagnosis-related tissue segmentation images, the segmented scar (light grey), health myocardium (dark grey), and blood pool (intermediate grey) from our method are highly consistent with the ground truth in terms of shape, location, and size.
Figure 9:
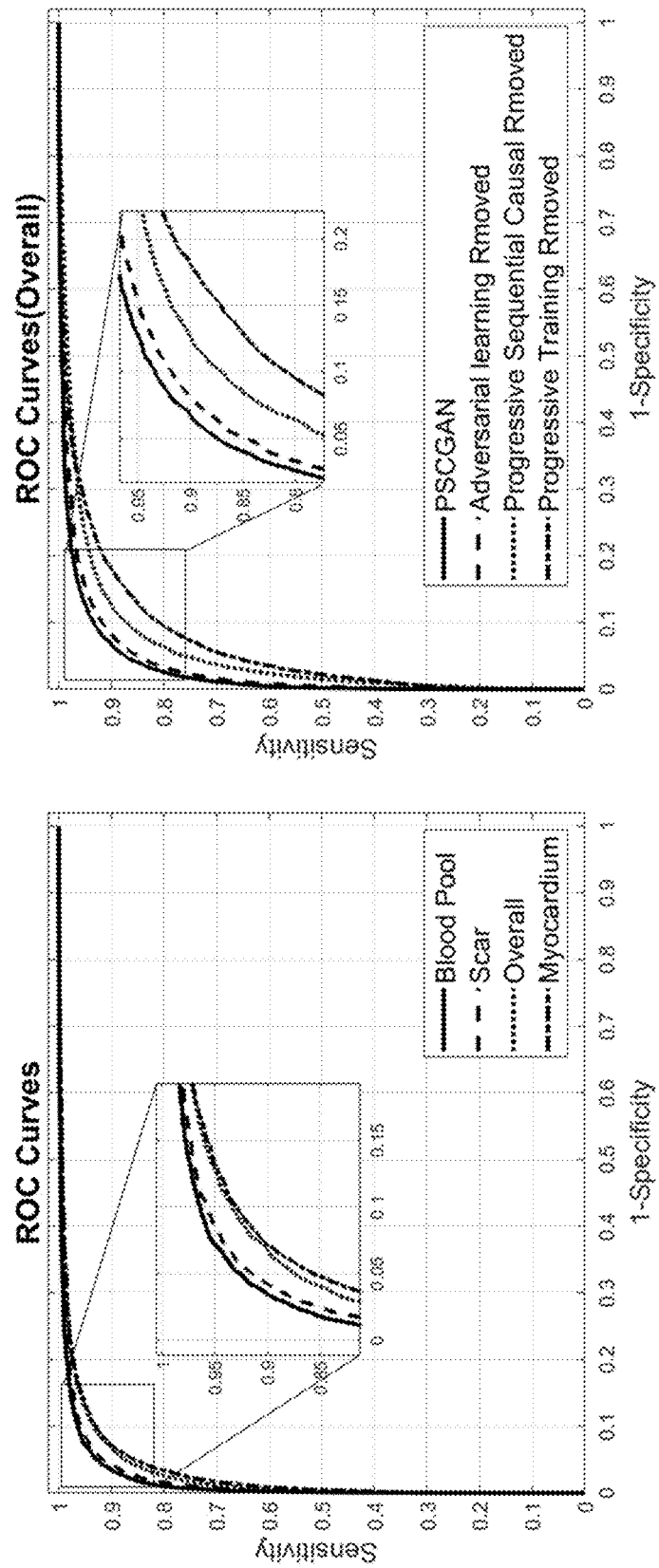
FIG. 9 shows that PSCGAN generated an accurate diagnosis-related tissue segmentation image and that each component in the PSCGAN effectively improved the segmentation accuracy.

Imageology metrics. Table 1 and FIG. 8 indicate that PSCGAN were able to synthetize high-quality LGE-equivalent images, which were almost identical to the LGE image based on CA injection, in terms of the imageology metrics. It achieved an SSIM of 0.78±0.10, a PSNR of 23.03±1.42, and an NRMSE of 0.11±0.05. Moreover, PSCGAN achieved an average SSIM of 0.76±0.18, a PSNR of 23.17±1.60, and an NRMSE of 0.10±0.09 when using the 10-fold random cross-validation. Note that higher values for SSIM and PSNR and lower values for NRMSE indicated better performance. Table 1, FIGS. 8 and 9 show that PSCGAN accurately segmented IHD scars, healthy myocardium and blood pools in terms of the imageological metrics. PSCGAN achieved an overall pixel segmentation accuracy of 97.17% with a sensitivity of 91.68% and a specificity of 98.53%. In particular, the accuracy of the scar segmentation is 97.13%, that of the healthy myocardium segmentation is 96.34% and that of the blood pool segmentation is 97.97%. PSCGAN obtained Dice coefficients of 0.93 for the scar tissue, 0.90 for the healthy myocardial tissue, and 0.93 for the blood pools. Moreover, when using the 10-fold random cross-validation, PSCGAN achieved an overall pixel segmentation accuracy of 97.11% with a sensitivity of 91.24% and a specificity of 98.67%. In particular, the accuracy of the scar segmentation is 96.94%, that of the healthy myocardium segmentation is 96.37% and that of the blood pool segmentation is 98.01%. PSCGAN obtained Dice coefficients of 0.90 for the scar tissue, 0.91 for the healthy myocardial tissue, and 0.93 for the blood pools (Table 2).

Figure 10:
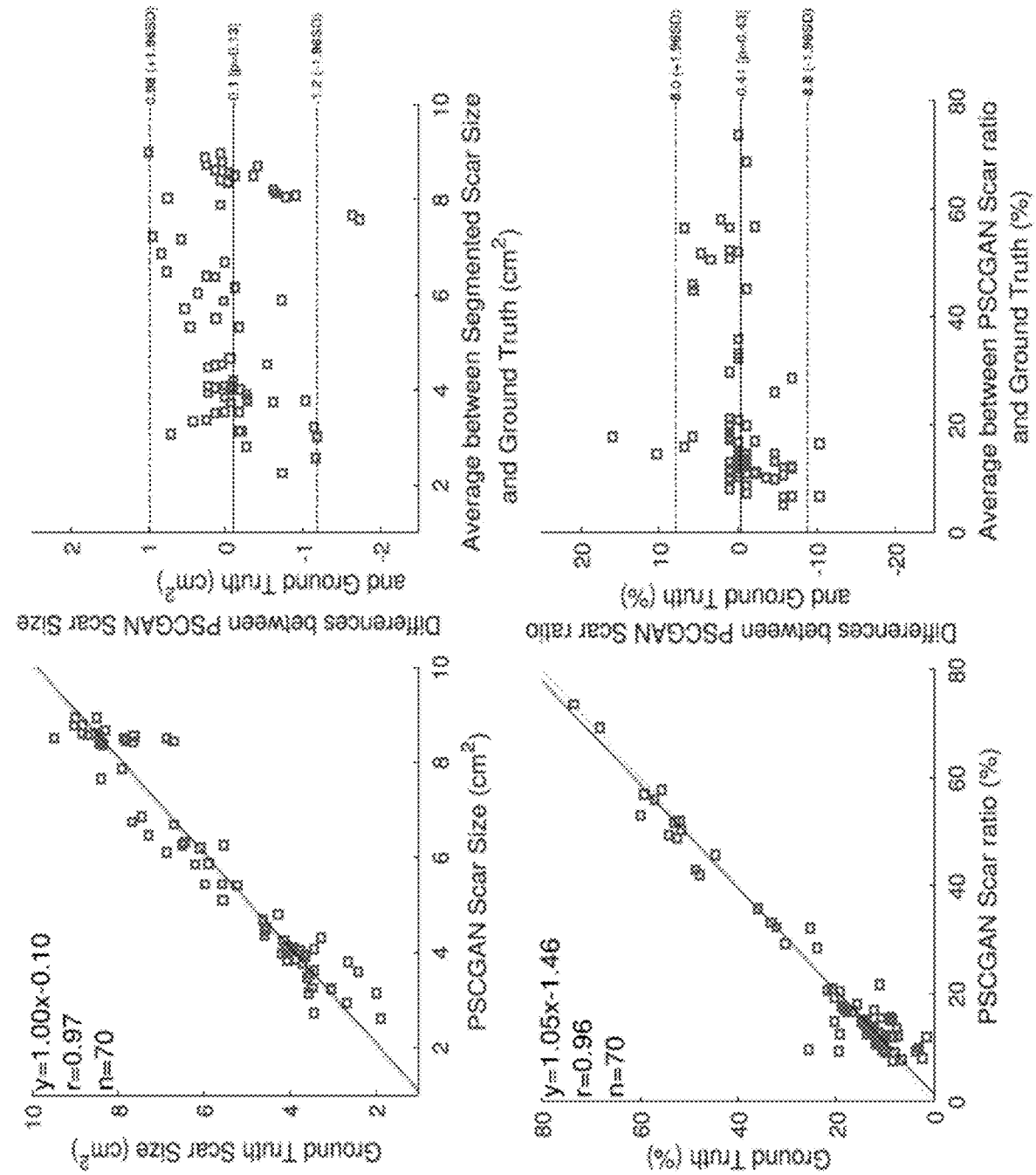
FIG. 10 shows that PSCGAN calculated scar sizes and scar ratios are highly consistent with those from the current clinical workflow as shown by comparisons with Bland-Altman analysis.

Clinical metrics. The experimental results also show that PSCGAN can provide radiologists with the same clinical metrics for diagnosis as current clinical workflows, as shown in FIG. 10, Tables 2 and 3. When compared to the ground truth, the PSCGAN achieved a correlation coefficient of 0.97 and −0.1 (0.98, −1.2) cm² for the corresponding biases (limits of agreement) in scar size, a sensitivity of 85.27% and a specificity of 97.47% in the segment-level scar localization, a correlation coefficient of 0.96 and 0.41 (8.0, −8.8)% for the corresponding biases (limits of agreement) in scar ratio, and a sensitivity of 86.95% and a specificity of 97.87% in scar transmurality. Moreover, when using the 10-fold random cross-validation, the PSCGAN achieved a correlation coefficient of 0.95 in scar size, a sensitivity of 84.80% and a specificity of 97.67% in the segment-level scar localization, a correlation coefficient of 0.94, in scar ratio, and a sensitivity of 82.61% and a specificity of 98.17% in scar transmurality.

TABLE 2

Clinical metrics obtained by PSCGAN are highly consistent with those obtained from the current clinical workflow.

|  | Sensitivity | Specificity | AUC |
|---|---|---|---|
| Scar segment-level localization | 85.27% | 97.47% | 0.90 |
| Scar transmurality | 86.95% | 97.87% | 0.91 |

|  | PSCGAN | Ground truth | Pearson's r (P-value) |
|---|---|---|---|
| Scar size (cm²) | 7.37 ± 2.17 | 5.64 ± 1.93 | 0.97 (0.24) |
| Scar ratio (%) | 29.10 ± 19.73 | 25.31 ± 17.62 | 0.96 (0.11) |

TABLE 3

Each technological innovation component in PSCGAN has effectively improved the its performance.

|  | Accuracy of overall segmentation image | SSIM of CA-free enhancement image | Pearson's r of scar size |
|---|---|---|---|
| PSGAN | 97.17(0.48)% | 0.78(0.10) | 0.97 |
| Adversarial learning removed | 95.92(0.57)% | 0.55(0.21) | 0.95 |
| Progressive training removed | 94.91(0.59)% | 0.61(0.19) | 0.93 |
| Sequential casual learning removed (3DConv) | 95.13(0.50)% | 0.64(0.17) | 0.96 |

Advantage of generative adversarial learning. FIG. 7 and Table 3 indicate that generative adversarial learning improves the performance of both the segmentation and the synthesis. Among them, the improvement of synthesis is particularly obvious. The generative adversarial learning of PSCGAN improved overall segmentation accuracy by 1.2%, the SSIM by 0.23, and the pearson's r of scar size by 0.02 compared to a network with adversarial learning removed, which only uses an SCLN-based generator with parallel output for segmentation and synthesis. Moreover, PSCGAN improved overall segmentation accuracy by 0.94%, the SSIM by 0.21, and the pearson's r of scar size by 0.02 when using the 10-fold random cross-validation. This improved performance fully proves that generative adversarial learning using game theory enables the learning of better representations from a latent space of data distribution, thereby optimizing the segmentation contours and enhancing the fine synthesis details.

Figure 11:
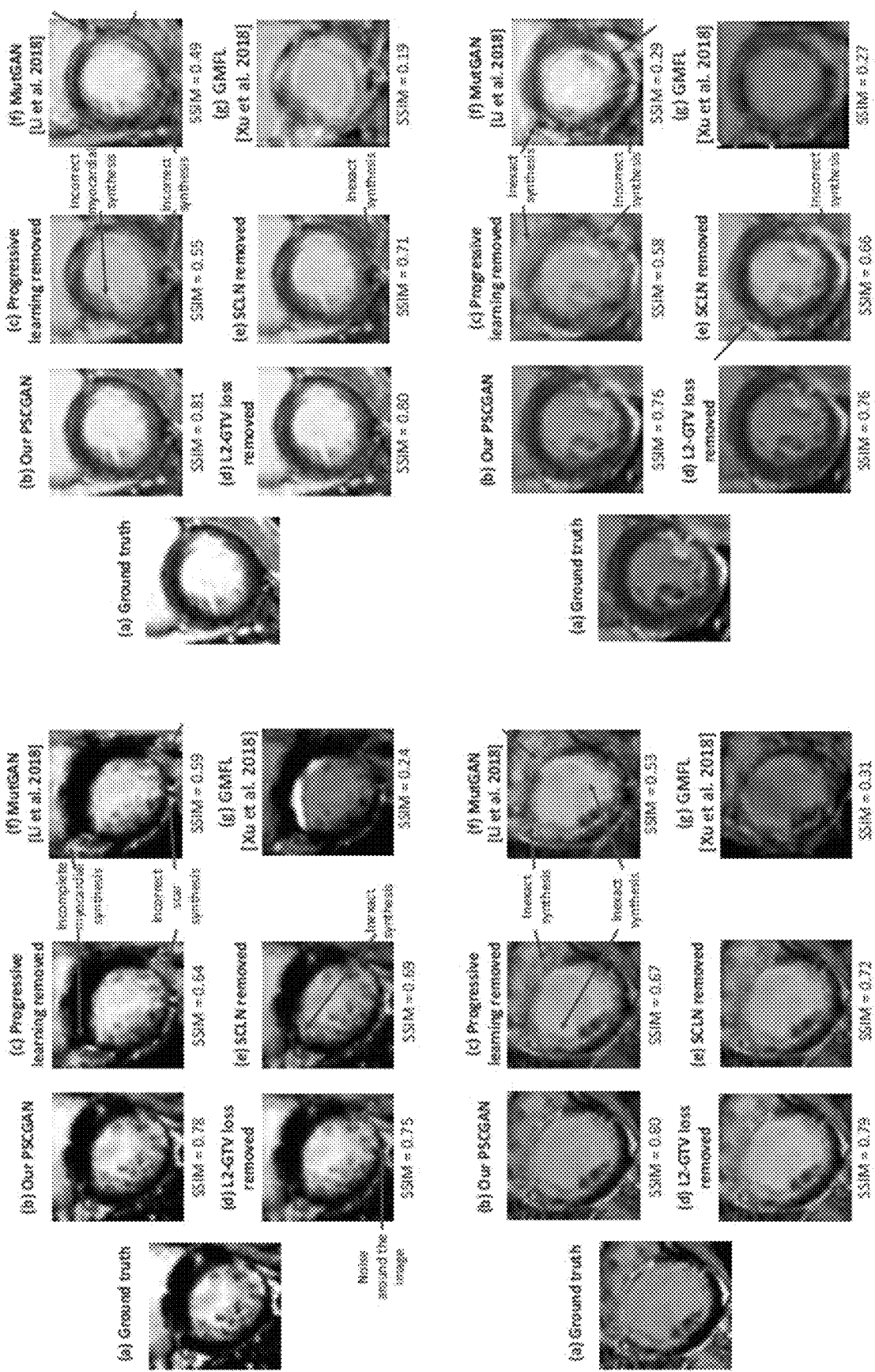
FIG. 11 shows that each component in the PSCGAN effectively improves LGE-equivalent image quality.
Figure 12:
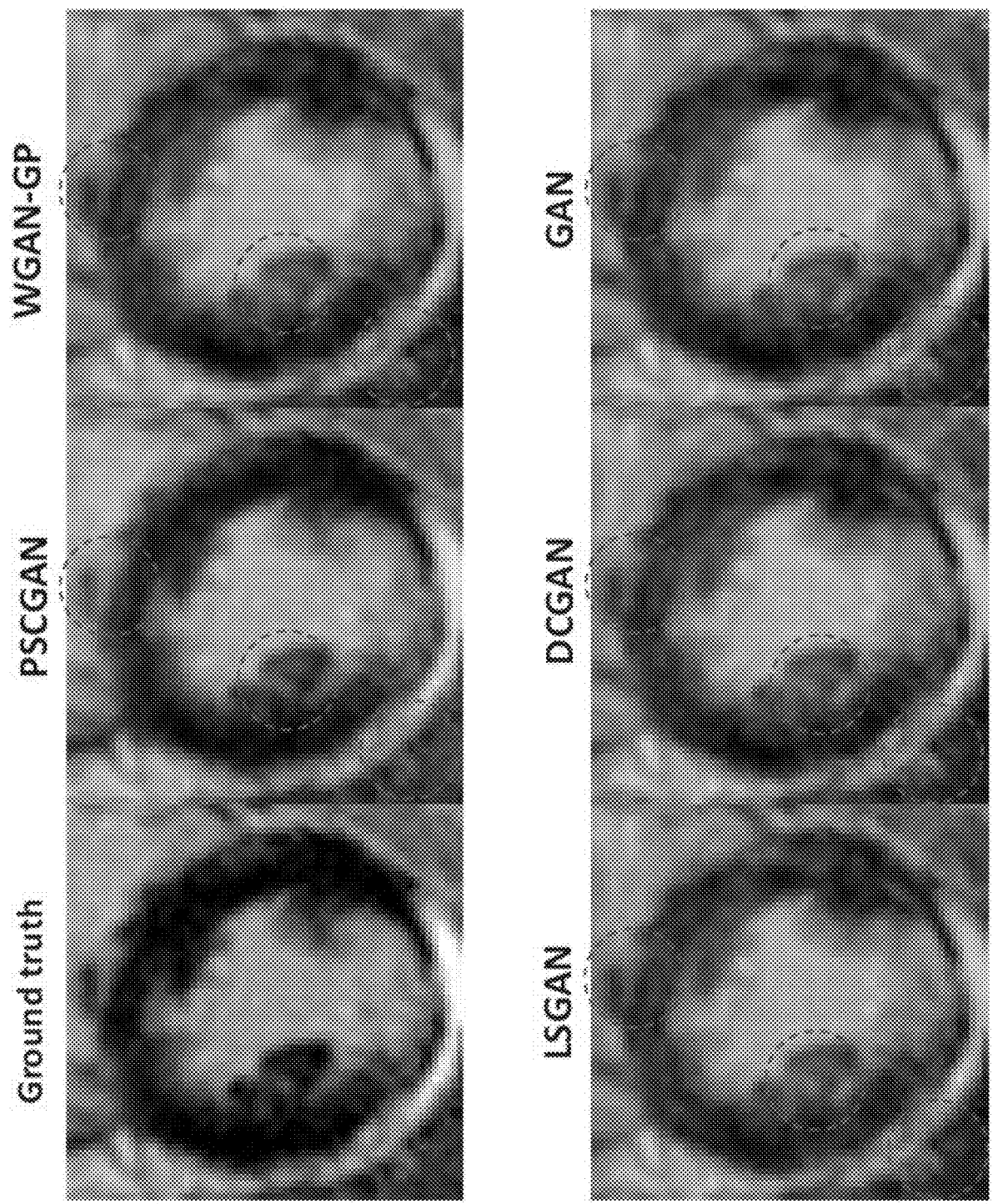
FIG. 12 shows that a hinge adversarial loss term in the PSCGAN improved performance in LGE-equivalent image synthesis.

Advantage of progressive training framework. FIGS. 9 and 11 and Table 3 indicate that the progressive training framework of the PSCGAN significantly improves the training stability while improving the learning efficiency and accuracy in both the segmentation and the synthesis. The PSCGAN improved the overall segmentation accuracy by 2.2%, the SSIM by 0.17, and the pearson's r of scar size by 0.04 compared with a network with the progressive framework removed that produced a parallel output of segmentation and synthesis using one generator ($G_{pri}$) and one discriminator ($D_{pri}$). The PSCGAN improved the overall segmentation accuracy by 1.92%, the SSIM by 0.11, and the pearson's r of scar size by 0.03 when using the 10-fold random cross-validation and progressive framework removed network. The standard deviation of the segmentation accuracy of the full PSCGAN was also reduced by 0.11% compared to the network with the framework removed, while the standard deviation of the SSIM was reduced by 0.09. Furthermore, the progressive framework also reduced the difference between the segmentation results from the ground truth and those from the LGE-equivalent images (0.09% in the PSCGAN and 1.20% in the progressive framework-removed version). All these improvements proved that the progressive framework created joint mappings that successively augmented the tissue mask and LGE-equivalent images in the synthesis and segmentation training. These joint mappings successfully exploited the commonalities between the LGE-equivalent images and the diagnosis-related segmentation images, thereby avoiding interference between the conditional probability distribution of the generative model-based synthetic task and the decision function of the discriminative model-based segmentation task (FIG. 12).

Figure 14:
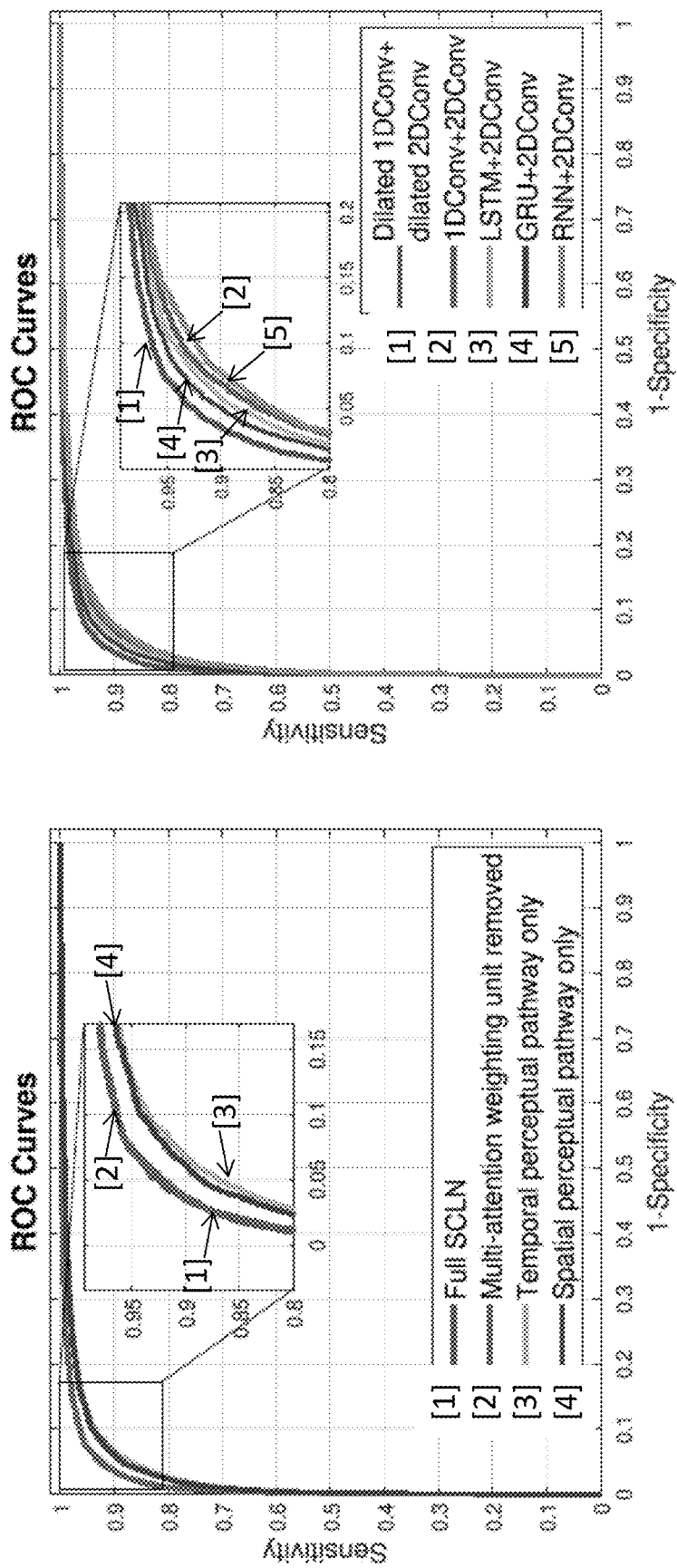
FIG. 14 shows that two-stream pathways and the weighing unit in the SCLN effectively improve segmentation accuracy, as does multi-scale, causal dilated convolution.
Figure 15:
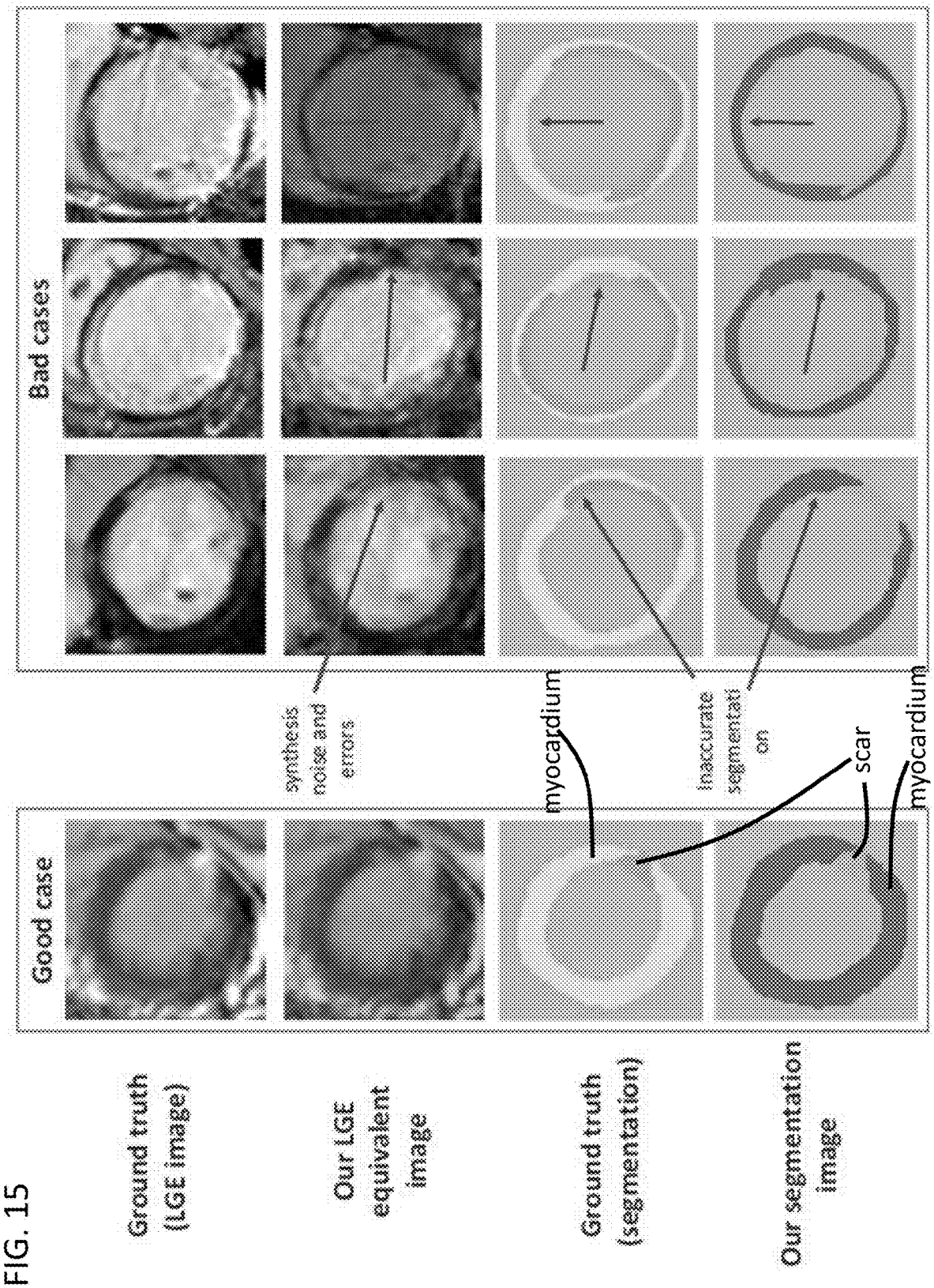
FIG. 15 shows visual examples of the synthesis and segmentation, including both good case and bad cases (arrows). The segmented scar appears as light grey and intermediate grey areas in our method and the ground truth, respectively. The segmented myocardium appears as dark grey and white areas in our method and the ground truth, respectively.

Advantage of sequential causal learning network (SCLN). FIGS. 9, 11, and 14 and Tables 3 and 4 indicate that the SCLN effectively improved both segmentation accuracy and synthesis quality. Compared with existing 2D+T time-series learning methods, SCLN improved the segmentation accuracy, the SSIM and the pearson's r of scar size by 2.14%, 0.14 and 0.01, respectively, compared to Conv3D, by 1.13%, 0.07 and 0.06, respectively, compared to ConvLSTM, and by 0.73%, 0.08 and 0.04, respectively, compared to 3DConv+LSTM. This is because SCLN creates a multi-scale, two-stream extractor to match spatial and temporal dependencies in time-series image learning, thereby avoiding the interference between these two dependencies during learning, and a multi-attention weighing unit is used to select the task-specific dependencies between and within the spatial and temporal dependencies. Particularly, the experimental results also indicate that each component of the SLCN effectively improved performance, especially that of synthesis, as shown in FIG. 14 and Table 4. Compared with the spatial perceptual pathway-alone version, the temporal perceptual pathway-alone version, and the multi-attention weighing unit-removed version, the SCLN shows improvements of 23.56%, 7.75%, and 0.45%, respectively, in segmentation accuracy, improvements of 0.30, 0.21, and 0.04, respectively, in SSIM, and improvements of 0.26, 0.14, and 0.03, respectively, in the Pearson's r of the scar size. Furthermore, FIG. 14 and Table 4 also indicate that, within the SCLN, multi-scale 2D causal dilated convolution+1D causal dilated convolution drive both the spatial perceptual pathway and the temporal perceptual pathway to achieve better performance. Compared with the other temporal information and spatial information separating learning methods, SCLN improved the segmentation accuracy and the SSIM by 2.65% and 0.08, respectively, compared to 2DConv+1DConv, by 1.95% and 0.05, respectively, compared to LSTM+2DConv, by 1.87% and 0.03, respectively, compared to GRU+2DConv, and by 4.06% and 0.17, respectively, compared to RNN+2DConv. This is because multi-scale, causal dilated convolution successfully handles the high local variations of pixels in the cine MR images by changing the dilation ratio to extract both long-range and short-range spatial and temporal dependencies. The cases where the PSCGAN method may be further improved are illustrated in FIG. 15, and mainly focus on the inaccurate synthesis and segmentation of scars. The PSCGAN method may be further improved by an imaging input other than the cine MR images that can improve the spatiotemporal representation learning of the heart. The spatiotemporal representation of the heart is a complex 3D change in both kinematics and morphology. Although cardiac cine MR images are the most effective and widely available protocol for imaging the beating heart, they are single short-axis images and are insufficient for presenting a complete spatiotemporal representation of the 3D swirl and spiral of the muscle cells in the heart. Therefore, the PSCGAN method can be expected to be further improved by introducing extra modality images (such as T2WI images) and extra view images (such as long-axis images).

mance. Moreover, Table 5 indicates that segmentation auxiliary loss improved the overall segmentation accuracy by 0.13% compared with the version with this loss term removed. This is because the segmentation auxiliary loss adds additional tissue size information to the discriminator, thereby motivating the network to learn more aspects of the distribution of the segmented images to improve the performance of the network. In addition, the experimental results indicated that hinge adversarial loss has the overall best performance when compared with other, recently developed adversarial losses, as shown in FIG. 12. In terms of segmentation, hinge adversarial loss term achieved the highest accuracy (97.17%), which was the same as that of WGAN-GP loss (Gulrajani et al., 2017) and LSGAN loss terms (Mao et al., 2017). In terms of synthesis, the hinge adversarial loss term achieved the highest SSIM (0.78), and the WGAN-GP loss term achieved the second highest SSIM (0.76).

Comparison with other state-of-the-art methods. The PSCGAN represent the first networks to combine CA-free IHD-diagnosing image synthesis and segmentation technologies, produced a greater number of diagnosis metrics and yielded higher IHD segmentation and diagnosis accuracies than existing state-of-the-art methods (Zhang et al., 2019; Bleton et al., 2015; Xu et al., 2017; Popescu et al.,

TABLE 4

SCLN outperforms recent time-series image learning methods, and each component in the SCLN effectively improves performance.

| | Full SCLN | Spatial perceptual pathway only | Temporal perceptual pathway only | multi-attention weighing removed | ConvLSTM | 3DConv + LSTM |
|---|---|---|---|---|---|---|
| Accuracy (Overall) | 97.17% | 73.61% | 89.42% | 96.72% | 95.97% | 96.47% |
| SSIM | 0.78 | 0.48 | 0.57 | 0.74 | 0.71 | 0.70 |
| Pearson's r (scar size) | 0.97 | 0.71 | 0.83 | 0.94 | 0.91 | 0.93 |

TABLE 5

Synthetic regularization loss effectively improved the quality of the LGE-equivalent images; segmentation auxiliary loss also effectively improved the accuracy of the diagnosis-related tissue segmentation images.

| PSCGAN | | Synthetic regularization loss removed | |
|---|---|---|---|
| SSIM | PSNR | SSIM | PSNR |
| 0.78(0.10) | 23.03(1.42) | 0.77(0.12) | 21.50(2.07) |

| PSCGAN Accuracy (overall) | Segmentation auxiliary loss removed Accuracy (overall) |
|---|---|
| 97.17(0.48)% | 97.04(0.58)% |

Figure 13:
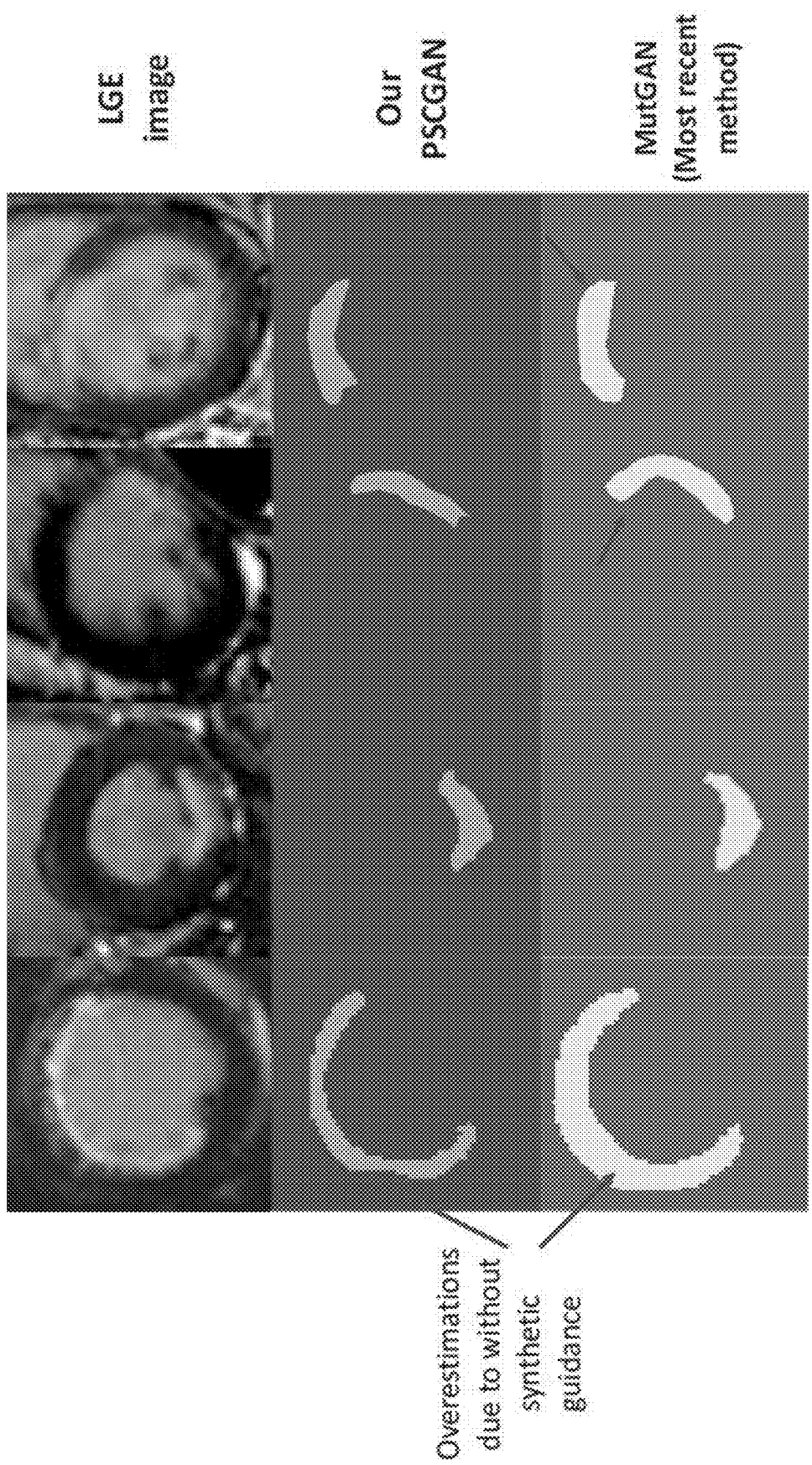
FIG. 13 shows that PSCGAN corrects the overestimation and boundary error issues in existing state-of-the-art scar segmentation methods.

Advantage of synthetic regularization loss and segmentation auxiliary loss. FIG. 11 and Table 5 indicate that synthetic regularization loss improved the quality of the synthesized image, especially in terms of PSNR. Synthetic regularization loss improved the PSNR by 1.8 compared to the network with the loss term removed. This is because synthetic regularization loss builds a group sparsity structure that has a natural grouping of its components and the components within a group. Thus, this loss reduces the degrees of freedom in the total variation during noise optimization, thereby leading to better synthesis perfor- 2016; Xu et al., 2018a), as shown in Table 6. PSCGAN improved scar segmentation accuracy 0.36%-12.74% compared to the other methods. PSCGAN correct the overestimation and boundary error issues in existing state-of-the-art scar segmentation methods, as shown in FIG. 13, by leveraging the textures and edges in LGE-equivalent images as priori conditions and by also leveraging the novel segmentation auxiliary loss terms. Moreover, PSCGAN successfully synthesized LGE-equivalent images. Note that some existing segmentation methods can be used mechanically for the synthesis task due to having the same input and output formats. PSCGAN achieved the highest SSIM values and improved the image quality in terms of scar presentation, boundary clarity, texture accuracy, and noise control, as shown in FIG. 11. This is because the progressive framework, the SCLN, and the synthetic regulation loss terms built accurate spatiotemporal representations of the cine MR images for each pixel of the LGE image. Importantly, the PSCGAN produced credible diagnosis metrics that cannot be produced by any existing IHD diagnosis or segmentation method, such as scar ratio. This is because PSCGAN enables the segmentation of all diagnosis-related tissues used for credible diagnosis metrics, rather than only scar-based metrics produced by existing binary segmentation methods.

TABLE 6

PSCGAN achieved more diagnosis metrics and higher segmentation and diagnosis accuracy than existing state-of-the-art methods in IHD diagnosis and segmentation.

|  | Seg/Sys | Accuracy (Scar) | Accuracy (Overall) | SSIM | Pearson's r for scar ratio |
|---|---|---|---|---|---|
| PSCGAN | Sys/Multi-Seg | 97.13% | 97.17% | 0.78 | 0.96 |
| (Xu et al., 2018a) | only scar Seg | 96.77% | NaN (94.60%) | 0.59* | NaN (0.93) |
| (Zhang et al., 2019) | only scar Seg | 95.03% | NaN (92.37%) | 0.31* | NaN (0.84) |
| (Xu et al., 2017) | only scar Seg | 94.93% | NaN (92.51%) | 0.31* | NaN (0.83) |
| (Popescu et al., 2016) | only scar Seg | 86.47% | — | — | — |
| (Bleton et al., 2015) | only scar Seg | 84.39% | — | — | — |

NaN(.) means that this method can only estimate this index after the radiologist manually segments the endocardium and epicardium.
*means that the framework of this method can be used to synthesize LGE-equivalent image.
— means that this method is incapable of estimating this index.

REFERENCES FOR EXPERIMENTAL EXAMPLE 1

Altman, D. G., Bland, J. M., 1983. Measurement in medicine: the analysis of method comparison studies. J. R. Stat. Soc. Ser. D 32 (3), 307-317.

Ba, J. L., Kiros, J. R., Hinton, G. E., 2016. Layer normalization stat 1050, 21. arXiv: 1607.06450.

Bandanau, D., Cho, K., Bengio, Y., 2015. Neural machine translation by jointly learning to align and translate. 3rd International Conference on Learning Representations. ICLR. arXiv: 1409.0473.

Beckett, K. R., Moriarity, A. K., Langer, J. M., 2015. Safe use of contrast media: what the radiologist needs to know. Radiographics 35 (6), 1738-1750.

Bijnens, B., Claus, P., Weidemann, F., Strotmann, J., Sutherland, G. R., 2007. Investigating cardiac function using motion and deformation analysis in the setting of coronary artery disease. Circulation 116 (21), 2453-2464.

Bleton, H., Margeta, J., Lombaert, H., Delingette, H., Ayache, N., 2015. Myocardial infarct localization using neighbourhood approximation forests. In: International Workshop on Statistical Atlases and Computational Models of the Heart. Springer, pp. 108-116.

Duchateau, N., De Craene, M., Allain, P., Saloux, E., Sermesant, M., 2016. Infarct localization from myocardial deformation: prediction and uncertainty quantification by regression from a low-dimensional space. IEEE Trans. Med. Imaging 35 (10), 2340-2352.

Fox, C. S., Muntner, P., Chen, A. Y., Alexander, K. P., Roe, M. T., Cannon, C. P., Saucedo, J. F., Kontos, M. C., Wiviott, S. D., 2010. Use of evidence-based therapies in short-term outcomes of st-segment elevation myocardial infarction and non-st-segment elevation myocardial infarction in patients with chronic kidney disease. Circulation 121 (3), 357-365.

Goodfellow, I., Bengio, Y., Courville, A., Bengio, Y., 2016. Deep Learning, vol. 1. MIT press Cambridge.

Goodfellow, I., Pouget-Abadie, J., Mirza, M., Xu, B., Warde-Farley, D., Ozair, S., Courville, A., Bengio, Y., 2014. Generative adversarial nets. In: Advances in Neural Information Processing Systems, pp. 2672-2680.

Gulrajani, I., Ahmed, F., Arjovsky, M., Dumoulin, V., Courville, A. C., 2017. Improved training of wasserstein gans. In: Advances in Neural Information Processing Systems, pp. 5767-5777.

He, K., Zhang, X., Ren, S., Sun, J., 2016. Deep residual learning for image recognition. In: Proceedings of the IEEE Conference on Computer Vision and Pattern Recognition, pp. 770-778.

Huang, X., Li, Y., Poursaeed, O., Hoperoft, J., Belongie, S., 2017. Stacked generative adversarial networks. In: Proceedings of the IEEE Conference on Computer Vision and Pattern Recognition, pp. 5077-5086.

Ingkanisorn, W. P., Rhoads, K. L., Aletras, A. H., Kellman, P., Arai, A. E., 2004. Gadolinium delayed enhancement cardiovascular magnetic resonance correlates with clinical measures of myocardial infarction. J. Am. Coll. Cardiol. 43 (12), 2253-2259.

Isola, P., Zhu, J.-Y., Zhou, T., Efros, A. A., 2017. Image-to-image translation with conditional adversarial networks. In: Proceedings of the IEEE conference on computer vision and pattern recognition. IEEE, pp. 1125-1134.

Johnson, J., Alahi, A., Fei-Fei, L., 2016. Perceptual losses for real-time style transfer and super-resolution. European Conference on Computer Vision. Springer, pp. 694-711.

Kali, A., Cokic, I., Tang, R. L., Yang, H.-J., Sharif, B., Marbán, E., Li, D., Berman, D., Dharmakumar, R., 2014. Determination of location, size and transmurality of chronic myocardial infarction without exogenous contrast media using cardiac magnetic resonance imaging at 3t. Cir. Cardiovasc. Imaging 7, 471-481.

Karras, T., Aila, T., Laine, S., Lehtinen, J., 2017. Progressive growing of gans for improved quality, stability, and variation. arXiv: 1710.10196.

Kingma, D. P., Ba, J. L., 2014. Adam: a method for stochastic optimization. In: Proc. 3rd Int. Conf. Learn. Representations.

Ledesma-Carbayo, M. J., Kybic, J., Desco, M., Santos, A., Suhling, M., Hunziker, P., Unser, M., 2005. Spatio-temporal nonrigid registration for ultrasound cardiac motion estimation. IEEE Trans. Med. Imaging 24 (9), 1113-1126.

Leiner, T., 2019. Deep learning for detection of myocardial scar tissue: goodbye to gadolinium. Radiology 291 (3).

Luc, P., Couprie, C., Chintala, S., Verbeek, J., 2016. Semantic segmentation using adversarial networks. NIPS Workshop on Adversarial Training. arXiv: 1611.08408.

Mao, X., Li, Q., Xie, H., Lau, R. Y., Wang, Z., Smolley, S. P., 2017. Least squares generative adversarial networks. In: Computer Vision (ICCV), 2017 IEEE International Conference on. IEEE, pp. 2813-2821.

Mirza, M., Osindero, S., 2014. Conditional generative adversarial nets. arXiv preprint arXiv: 1411.1784.

Moon, J. C., Reed, E., Sheppard, M. N., Elkington, A. G., Ho, S., Burke, M., Petrou, M., Pennell, D. J., 2004. The histologic basis of late gadolinium enhancement cardiovascular magnetic resonance in hypertrophic cardiomyopathy. J. Am. Coll. Cardiol. 43 (12), 2260-2264.

van den Oord, A., Dieleman, S., Zen, H., Simonyan, K., Vinyals, O., Graves, A., Kalchbrenner, N., Senior, A., Kavukcuoglu, K., 2016. Wavenet: a generative model for raw audio. 9th ISCA Speech Synthesis Workshop, p. 125. arXiv: 1609.03499.

Ordovas, K. G., Higgins, C. B., 2011. Delayed contrast enhancement on mr images of myocardium: past, present, future. Radiology 261 (2), 358-374.

Peyré, G., Fadili, J., 2011. Group sparsity with overlapping partition functions. In: 2011 19th European Signal Processing Conference. IEEE, pp. 303-307.

Popescu, I. A., Irving, B., Borlotti, A., Dall'rmellina, E., Grau, V., 2016. Myocardial scar quantification using slic supervoxels-parcellation based on tissue characteristic strains. In: International Workshop on Statistical Atlases and Computational Models of the Heart. Springer, pp. 182-190.

Pumarola, A., Agudo, A., Martinez, A. M., Sanfeliu, A., Moreno-Noguer, F., 2018. Ganimation: anatomically-aware facial animation from a single image. In: Proceedings of the European Conference on Computer Vision, pp. 818-833.

Ronneberger, O., Fischer, P., Brox, T., 2015. U-net: convolutional networks for biomedical image segmentation. In: International Conference on Medical image computing and computer-assisted intervention. Springer, pp. 234-241.

Su, R., Xie, W., Tan, T., 2020. 2.75 d convolutional neural network for pulmonary nodule classification in chest ct. arXiv preprint arXiv: 2002.04251.

Suinesiaputra, A., Ablin, P., Alba, X., Alessandrini, M., Allen, J., Bai, W., Cimen, S., Claes, P., Cowan, B. R., D'hooge, J., et al., 2017. Statistical shape modeling of the left ventricle: myocardial infarct classification challenge. IEEE J. Biomed. Health Inf. 22 (2), 503-515.

Tan, T., Platel, B., Huisman, H., Sanchez, C. I., Mus, R., Karssemeijer, N., 2012. Computer-aided lesion diagnosis in automated 3-d breast ultrasound using coronal spiculation. IEEE Trans. Med. Imaging 31 (5), 1034-1042.

Tan, T., Platel, B., Mann, R. M., Huisman, H., Karssemeijer, N., 2013. Chest wall segmentation in automated 3d breast ultrasound scans. Med. Image Anal. 17 (8), 1273-1281.

Tan, T., Platel, B., Mus, R., Tabar, L., Mann, R. M., Karssemeijer, N., 2013. Computer-aided detection of cancer in automated 3-d breast ultrasound. IEEE Trans. Med. Imaging 32 (9), 1698-1706.

Vaswani, A., Shazeer, N., Parmar, N., Uszkoreit, J., Jones, L., Gomez, A. N., Kaiser, L., Polosukhin, I., 2017. Attention is all you need. In: Advances in Neural Information Processing Systems, pp. 5998-6008.

Wang, X., Girshick, R., Gupta, A., He, K., 2018. Non-local neural networks. In: Proceedings of the IEEE Conference on Computer Vision and Pattern Recognition, pp. 7794-7803.

Wang, Z., Bovik, A. C., Sheikh, H. R., Simoncelli, E. P., et al., 2004. Image quality assessment: from error visibility to structural similarity. IEEE Trans. Image Process. 13 (4), 600-612.

Welstead, S. T., 1999. Fractal and Wavelet Image Compression Techniques. SPIE Optical Engineering Press Bellingham, Washington Wong, K. C., Tee, M., Chen, M., Bluemke, D. A., Summers, R. M., Yao, J., 2016. Regional infarction identification from cardiac ct images: a computer-aided biomechanical approach. Int. J. Comput. Assist. Radiol. Surg. 11 (9), 1573-1583.

Xu, C., Xu, L., Brahm, G., Zhang, H., Li, S., 2018. Mutgan: simultaneous segmentation and quantification of myocardial infarction without contrast agents via joint adversarial learning. In: MICCAI. Springer, pp. 525-534.

Xu, C., Xu, L., Gao, Z., Zhao, S., Zhang, H., Zhang, Y., Du, X., Zhao, S., Ghista, D., Li, S., 2017. Direct detection of pixel-level myocardial infarction areas via a deep-learning algorithm. In: International Conference on Medical Image Computing and Computer-Assisted Intervention. Springer, pp. 240-249.

Xu, C., Xu, L., Gao, Z., Zhao, S., Zhang, H., Zhang, Y., Du, X., Zhao, S., Ghista, D., Liu, H., et al., 2018. Direct delineation of myocardial infarction without contrast agents using a joint motion feature learning architecture. Med. Image Anal. 50, 82-94.

Yu, F., Koltun, V., 2015. Multi-scale context aggregation by dilated convolutions. arXiv preprint arXiv: 1511.07122.

Zhang, H., Goodfellow, I., Metaxas, D., Odena, A., 2019a. Self-attention generative adversarial networks. International Conference on Machine Learning, pp. 7354-7363. arXiv preprint arXiv:1805.08318

Zhang, H., Xu, T., Li, H., Zhang, S., Wang, X., Huang, X., Metaxas, D. N., 2018. Stackgan++: realistic image synthesis with stacked generative adversarial networks. IEEE Trans. Pattern Anal. Mach. Intell. 41 (8), 1947-1962.

Zhang, N., Yang, G., Gao, Z., Xu, C., Zhang, Y., Shi, R., Keegan, J., Xu, L., Zhang, H., Fan, Z., et al., 2019. Deep learning for diagnosis of chronic myocardial infarction on nonenhanced cardiac cine mri. Radiology 291 (3), 606-617.

Zhao, J., Mathieu, M., LeCun, Y., 2019. Energy-based generative adversarial network. 5th International Conference on Learning Representations. ICLR.

Zhou, P., Shi, W., Tian, J., Qi, Z., Li, B., Hao, H., Xu, B., 2016. Attention-based bidirectional long short-term memory networks for relation classification. In: Proceedings of the 54th Annual Meeting of the Association for Computational Linguistics (Volume 2: Short Papers), pp. 207-212.

Experimental Example 2

The details of Experimental Example 2 are extracted from a prior scientific publication (Zhao et al., (2020) "Tripartite-GAN: Synthesizing liver contrast-enhanced MRI to improve tumor detection", Medical Image Analysis, Vol. 63: article 101667), and this scientific publication is incorporated herein by reference in its entirety. In the event of inconsistency between the incorporated material and the express disclosure of the current document, the incorporated material should be considered supplementary to that of the current document; for irreconcilable inconsistencies, the current document controls.

In this Experimental Example 2, a synthetic CEMRI or a CEMRI equivalent synthesis is an image that is synthesized from image data acquired in absence of contrast agent (CA) administration by a machine learning model to achieve imaging equivalent to CA-enhanced imaging for purposes of a concurrent diagnostic image analysis by the machine learning model achieving diagnostic results comparable to human expert diagnosis using CA-enhanced imaging. Therefore, in Experimental Example 2, synthetic CEMRI, synthesized CEMRI, CEMRI equivalent synthesis or terms implying the same can used interchangeably with the terms CA-free image or CA-free-AI-enhanced image or CA-free-AI-enhanced imaging.

Figure 16:
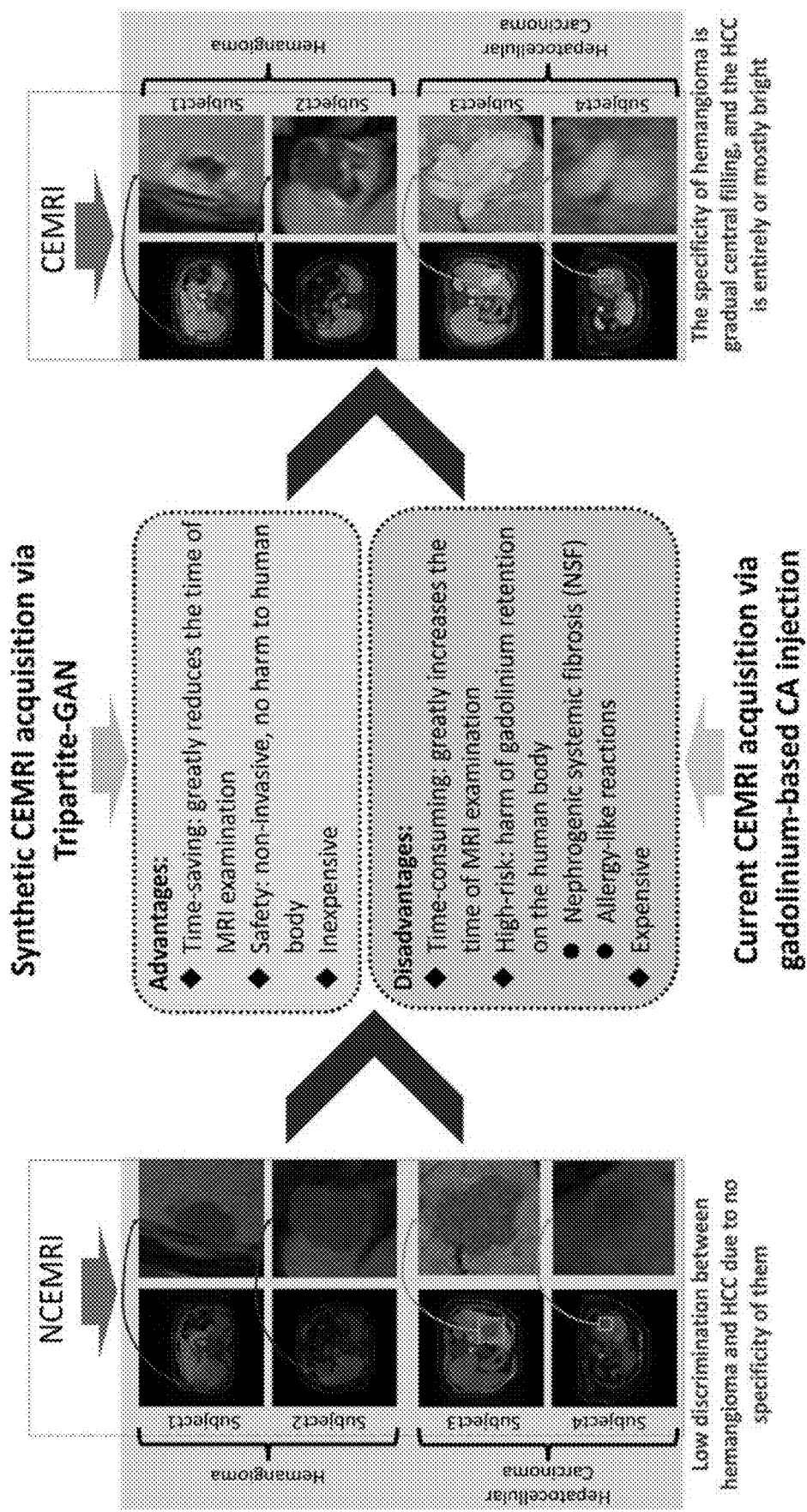
FIG. 16 shows a schematic of advantages of the present CA-free medical imaging technology (synthetic CEMRI) compared to existing non-contrast enhanced MRI (NCEMRI) methods and compared to existing contrast enhanced MRI (CEMRI) methods. There are four cases of synthesizing CEMRI from NCEMRI. Subject1 and Subject2 are hemangioma, a benign tumor. Subject3 and Subject4 are hepatocellular carcinoma (HCC), a malignant tumor.

There is currently no reported synthesis of non-contrast-enhanced-equivalent of liver contrast-enhanced MRI (CEMRI) for tumor detection because of three unique challenges: 1) The difficulty in discriminating the tumor features extracted in non-contrast-enhanced MRI (NCEMRI), in that it is easy to confuse the features of hemangioma (a benign tumor) and hepatocellular carcinoma (HCC, a malignant tumor) when extracting the features because of the low discrimination of hemangioma and HCC in NCEMRI as shown for example in FIG. 16. 2) The difficulty in learning the highly nonlinear mapping between multi-class NCEMRI and multi-class CEMRI in that each anatomy can be seen as a class, and different from the synthesis of single-class medical images (for example, brain MRI or lesion area patches), liver MRI has multi-class anatomy (i.e., liver, spleen, spine, and so on). Therefore, multi-class liver MRI has the risk of causing misclassification of the anatomy. 3) The difficulty in alleviating the blurring problem of synthetic CEMRI. The blurring of synthetic image is a problem that GAN needs to alleviate (Korkinof et al., 2018), and the problem becomes more serious due to the complex anatomy of multi-class liver MRI in that tumor detection is improved by not only a high quality of CEMRI synthesis but also the clarity of the tumor area.

A novel Tripartite Generative Adversarial Network (Tripartite-GAN) is provided herein as a non-invasive, time-saving, and inexpensive clinical tool to synthesize liver CEMRI without CA injection for tumor detection. Specifically, for the first time, the Tripartite-GAN combines three associated-network (an attention-aware generator, a convolutional neural network-based (CNN-based) discriminator, and a region-based convolutional neural network-based (R-CNN-based) detector), which concurrently or simultaneously achieves CEMRI synthesis and tumor detection in an end-to-end framework. Firstly, in order to overcome the aforementioned challenges of 1) and 2), the newly designed attention-aware generator expands the receptive field via hybrid convolution, integrates local features with their global dependencies via dual attention module (DAM), and improves the convergence of loss via residual learning. This is capable of effectively extracting the diagnosis-specific features of two types of tumor and accurately learning the highly nonlinear mapping between multi-class NCEMRI and multi-class CEMRI. Secondly, in order to overcome the aforementioned challenge of 3) for achieving high-quality CEMRI synthesis, which is equivalent to real CEMRI, the CNN-based discriminator is trained to discriminate the real or fake of synthetic CEMRI, and then promotes the generator to synthesize highly authentic CEMRI via adversarial-strategy. Thirdly, the R-CNN-based detector is combined to the generator via back-propagation for the first time, which achieves that CEMRI synthesis and tumor detection promote each other in an end-to-end framework. Moreover, the attention maps obtained from the generator newly added into the detector improve the performance of tumor detection.

Existing automated analysis in liver MRI. Although there are many works focused on medical image synthesis (for example, Costa et al., 2017), no work has achieved liver CEMRI-equivalent synthesis from NCEMRI without CA injection due to challenges of complex anatomy and patient diversity in liver MRI. Existing works are limited to medical image synthesis and tumor detection done separately, while the synthesis work is mostly focused on the single-class medical image (e.g., brain MRI, liver lesion area patch) and not a multi-class medical image such as would be needed for tumor detection in liver.

Existing GAN for medical image analysis. GAN has demonstrated great power in the medical image analysis since it was proposed by Goodfellow et al. (2014), which is used to model the image distribution of generated samples to be indistinguishable from target images. There are many studies focusing on medical image synthesis have obtained certain success (Nie et al., 2018). Besides, based on the generated samples, a wide variety of applications are derived. Such as improving liver lesion classification via GAN-based synthetic image, improving the accuracy and clarity of retinal vessel segmentation by using GAN-based network, accelerating automatic spondylolisthesis grading from MRIs across modalities by using a customized GAN, and improving lesion detection by using GAN-based network to synthesize PET from CT. These GAN-based works highlight the importance of image synthesis quality. It is worth noting that these works focus more on high-quality medical image synthesis, and then using the generated samples to improve the associated tasks. Although these works attempt to use GAN to promote another associated network, the GAN and the associated network work separately. None of them achieve the combination and mutual improvement between GAN and other associated networks in an end-to-end framework. Recently, in the field of natural images, some studies have attempted to combine GAN and other tasks networks and obtained some success (Simon et al., 2019; Shen et al., 2018; Chongxuan et al., 2017). For instance, in (Simon et al., 2019), a three-player GAN which combined the GAN and classifier by back-propagation was proposed to improve classification networks.

Existing Attention Module in networks. Since work (Vaswani et al., 2017) proposed to use the self-attention mechanism to draw global dependencies of inputs, which was successfully applied to machine translation, the attention mechanism has been widely used in various deep learning-based tasks. For example, Zhang et al., (2018) proposed a self-attention GAN to model long-range dependencies effectively. In other examples, relation modules were proposed to learn the information between objects for improving object recognition in an end-to-end object detector. In another example, (Fu, J., Liu, J., Tian, H., Li, Y., Bao, Y., Fang, Z., Lu, H., 2019. Dual attention network for scene segmentation, in: Proceedings of the IEEE Conference on Computer Vision and Pattern Recognition, pp. 3146-3154) a channel attention module and position attention module were embedded into a network of scene segmentation to adaptively integrate local features with their global dependencies.

An overview of the novel Tripartite-GAN. For effective CEMRI synthesis and tumor detection, the Tripartite-GAN provided herein executes the competition between three participants: the newly designed attention-aware generator, the CNN-based discriminator, and the R-CNN-based detector. FIG. 17 shows the design of the Tripartite-GAN. Specifically, the attention-aware generator is a hybrid convolution network to synthesize tumor-specific CEMRI, which facilitates tumor detection. The generator is embedded the DAM which includes a minutious attention module (MAM) and a global attention module (GAM) in a parallel manner. The MAM exploits the interdependencies between channel feature maps to emphasize interdependent feature maps and improve the feature representation of specific anatomy, which can enhance the detailed synthesis of tumor specificity. The GAM encodes a wider range of contextual information of multi-class liver MRI into local features to make the Tripartite-GAN context-aware, which enhances the learning ability of highly nonlinear mapping between multi-class NCEMRI and CEMRI, and then improves the accuracy and spatial continuity of CEMRI synthesis. Furthermore, the hybrid convolution was adopted to reserve the useful information without the pooling operation and expanding the receptive field in the step of feature extraction. The discriminator is a CNN designed to distinguish real or fake of synthetic CEMRI and promote the generator to synthesize high-quality CEMRI via adversarial-strategy. The detector is a R-CNN designed to locate and classify the tumor. The detector prompts the generator to focus on the difference between NCEMRI and CEMRI via the back-propagation, especially for the specificity of hemangioma and HCC. Meanwhile, the generator improves the performance of tumor detection via newly adding attention maps into the detector in the manner of residual connection.

Attention-aware generator with DAM for CEMRI synthesis. The attention-aware generator is designed based on a fully convolutional network (FCN) by embedding DAM in a parallel manner, which aims to synthesize CEMRI from NCEMRI by learning the nonlinear mapping between CEMRI and NCEMRI. Firstly, the generator extracts feature from NCEMRI via hybrid convolution. Moreover, the application of residual learning in CNN has achieved promising results in many challenging generic image processing tasks. For the generator in our Tripartite-GAN, the residual learning is performed to connect the layer of Conv2 and the layer of Dilated4, which improves the convergence of generator loss to facilitate the training of the generator. Secondly, the feature map obtained from the layer of Deconv2 is fed into the DAM (MAM and GAM), the MAM enhances detailed feature extraction by utilizing the interdependencies between channel maps of the layer of Deconv2, and the GAM explicitly captures global dependencies of multi-class liver MRI by encoding global contextual information into local features. Followed the DAM, we perform an element-wise sum to accomplish the feature fusion of MAM and GAM. Lastly, the last layer of Conv3 is used to generate the final synthetic CEMRI.

The architecture of the attention-aware generator. As shown in FIG. 18, the generator synthesis of CEMRI mainly goes through three steps: hybrid convolution, DAM, and the last convolution layer. Specifically, the generator adopts four dilated convolution layers rather than standard convolution layers for enlarging receptive fields. Furthermore, two convolution layers and two deconvolution layers are added to the front end and back end of dilated convolution operations, respectively. The two convolution layers contain the operation of convolution, batch normalization (BN), Rectified Linear Unit (ReLU), and max-pooling. The four dilated convolution layers contain the operation of dilated convolution, BN, and ReLU. The two deconvolution layers contain the operation of deconvolution, BN, and ReLU. Note that we do not adopt all the eight layers as dilated convolution. This reduces the size of feature maps and increases the receptive field more efficiently. The kernel sizes from the first convolution operation Conv1 to the last convolution operation Conv3 are 7×7, 3×3, 3×3, 3×3, 3×3, 3×3, 3×3, 3×3 and 3×3, respectively. The numbers of filters are 32, 64, 128, 128, 128, 64, 64, 32 and 1, respectively. Furthermore, the dilated rates are set to 1, 2, 3, and 5 from the layer of Dilated1 to Dilated4 to avoid a gridding issue.

MAM: Enhancing the feature representation of hemangioma and HCC for accurate tumor discrimination. The MAM explicitly models the interdependencies between channels of the Deconv2 in hybrid convolution. For the hybrid convolution, each channel map of high-level features can be regarded as an anatomy-specific response, and the different anatomic structure responses are associated with each other (Fu et al., 2019). Therefore, the MAM emphasizes interdependent feature maps and improves the feature representation of specific anatomy by utilizing the interdependencies between channel maps. Especially for the CEMRI, the difference between the specificity of tumors and normal tissues are more conspicuous than the NCEMRI. Accordingly, the MAM is embedded into the generator to enhance detailed feature extraction, especially for the details of tumor specificity. Specifically, after the feature map of the Deconv2 feeding into MAM, the MAM goes through three steps to obtain the output feature. Firstly, a channel attention matrix is generated, which models the channel relationship between any two pixels of the feature map. Secondly, a matrix multiplication operation is performed between the channel matrix and the original features. Thirdly, an element-wise sum operation is performed on the above multiplied resulting matrix and original features to obtain the final representations reflecting the specificity of the different anatomy.

The MAM as shown in FIG. 19, directly calculates the minutious attention feature map $Z \in R^{C \times C}$ from the feature $X \in R^{C \times H \times W}$ of Deconv2.

Firstly, we reshape X to $R^{C \times N}$, and then perform a matrix multiplication between X and its transpose.

Next, we apply a softmax layer to obtain the minutious attention map $Z \in R^{C \times C}$:

$$\text{Minutious Attention Matrix:} \quad Z_{ji} = \frac{\exp(X_i \cdot X_j)}{\sum_{i=1}^{C} \exp(X_i \cdot X_j)} \quad (18)$$

where $Z_{ji}$ measures the impact of ith channel on jth channel. In addition, we perform a matrix multiplication between the transpose of Z and X, then reshape their result to $R^{C \times H \times W}$ Lastly, we multiply the result by a scale parameter $\beta$ and use an execution element summation operation to get the final output $Y_M$:

$$\text{Output of } MAM: Y_{Mj} = \beta \sum_{i=1}^{C} (Z_{ji} X_i) + X_j \quad (19)$$

where $\beta$ is initialized as 0 and gradually increases weight through learning. The $Y_M$ shows the final feature of each channel is a weighted sum of the features of all channels and original features, it boosts feature discriminability.

GAM: Aggregating long-range contextual information of multi-class liver MRI for CEMRI synthesis. Context relationship is useful for anatomic structure understanding, especially for the liver MRI with complex anatomical structures. However, many works (Peng et al., 2017; Zhao et al., 2017) suggest that traditional FCN could lead to misclassification of objects with local feature representations generated. To overcome the defect of local feature representations, the GAM explicitly captures global dependencies regardless of locations, which adaptively aggregate long-range contextual information to make the framework context-aware. Specifically, after the feature map of the Deconv2 feeding into GAM, the GAM goes through three steps to obtain the output feature, which is similar to the MAM. The first step is to generate a spatial attention matrix that models the spatial relationship between any two pixels of the feature map. Secondly, a matrix multiplication operation is performed between the spatial matrix and the original features. Thirdly, an element-wise sum operation is performed on the above multiplied resulting matrix and original features to obtain the final representations reflecting long-range contexts.

The GAM encodes the global contextual information into local features, thus enhancing their representative capability. The operation of GAM as illustrated in FIG. 20, first give the feature $X \in R^{C \times H \times W}$ of Deconv2 to the GAM. Then feed X into two parallel convolution layers f and g to generate two feature map $f_S$ and $g_S$, where the kernel size of layer f and layer g are all 1×1. Next, we reshape $f_S$ and $g_S$ from $R^{C \times H \times W}$ to $R^{C \times N}$ where N=H×W is the number of features. After that we perform a matrix multiplication between the transpose of $f_S$ and $g_S$, and apply a softmax layer to calculate the global attention map $S \in R^{N \times N}$:

$$\text{Global Attention Matrix: } S_{mn} = \frac{\exp(f_{sn} \cdot g_{sm})}{\sum_{i=1}^{N} \exp(f_{sn} \cdot g_{sm})} \quad (20)$$

where $S_{mn}$ measures the impact of nth position on mth position. Note that the more similar feature representations of the two positions contribute to greater correlation between them.

The bottom path (FIG. 20) is a convolution layer with 1×1 kernel size. It is used to generate a feature map $h_S \in R^{C \times H \times W}$, and then reshape it to $h_S \in R^{C \times N}$. Next, we perform a matrix multiplication between $h_S$ and the transpose of S, and then reshape the result to $R^{C \times H \times W}$. Finally, we multiply it by a scale parameter α and perform an element-wise sum operation with the features X to obtain the final output feature maps $Y_G \in R^{C \times H \times W}$ as follows:

$$\text{Output of GAM: } Y_{GM} = \alpha \sum_{n=1}^{N} (S_{mn} h_{sn}) + X_m \quad (21)$$

where α is initialized as 0 and gradually increases weight through learning. In Eq. (21), the final feature $Y_G$ at each position is a weighted sum of the features at all positions and the original feature X. Therefore, it has a global contextual view and selectively aggregates contexts according to the global attention map. These feature representations achieve mutual gains and more robust for the CEMRI synthesis.

Advantages of the attention-aware generator include: 1) hybrid convolution expands the receptive fields more efficiently; 2) DAM enhances the ability to extract features by modeling the interdependencies between channels and encoding global contextual information into local features; and 3) residual learning facilitates the convergence of the training loss of Tripartite-GAN, which makes the loss of Tripartite-GAN lower.

The CNN-based discriminator makes the Tripartite-GAN adversarial-strategy-aware. As shown in FIG. 21, the CNN-based discriminator includes three convolution layers and three fully connected layers, where each convolution is followed by the operation of BN, ReLU, and max-pooling. The discriminator makes the Tripartite-GAN adversarial-strategy-aware because it receives either the synthetic CEMRI from the generator or real CEMRI from ground truth, and outputs a single scalar to indicate the image is real or fake and feedbacks to the generator. With learning through this confrontation, the discriminative eagerly prompts the generator to synthesize highly realistic CEMRI, until the truth or false is hard to discriminate.

The detector is the first time combined with the regular GAN in an end-to-end framework for tumor detection. FIG. 22 shows the architecture of the detector, which is a customized Faster R-CNN. The detector aims to directly locate the tumor location for obtaining the Region of Interest (RoI) of hemangioma and HCC. And the detector distinguishes whether it is a benign tumor or a malignant tumor. The detector encourages the generator to pay more attention to the specificity of the two types of tumors via back-propagation, which makes the generator synthesize CEMRI accurately. The detection is mainly comprised of two steps. The first stage is proposing the candidate tumor bounding boxes via the Region Proposal Network. The second stage is performing classification and bounding-box regression on the RoI of the tumor proposed in the first stage. It adopts a customized Simonyan and Zisserman model (Simonyan, K., Zisserman, A., 2014. Very deep convolutional networks for large-scale image recognition. arXiv preprint arXiv: 1409.1556) (VGG-16) with the help of attention maps obtained from DAM in the generator for feature extraction, in which the VGG-16 based network has eight shareable convolutional layers. The advantage over a single detection network is that we can get help from the attention maps extracted by the attention-aware generator. Although the tasks of the generator and detector are different, the generator is used to synthesize CEMRI, and the detector is used to detect tumors. While the generator extracts the global features of the entire liver MRI to ensure the quality of the entire synthetic CEMRI, it can also extract local features (such as tumor-specific features). Similar to the generator, the detector needs to extract the tumor feature for tumor location and classification. Therefore, the features extracted by the generator can help the feature extraction of the detector in the characterization of tumor details. In our Tripartite-GAN, we achieve the help of the generator to the detector by adding the attention maps to VGG-16 based convolution operation in the manner of residual connection. It mainly has two shortcuts of adding the attention map to VGG-16. The first shortcut is to add the attention map from DAM directly before the first convolution layer of VGG-16, and the second shortcut is to add the attention map after the pooling layer operation to the third convolution layer of VGG-16.

Tripartite loss joint strategy combines three associated-tasks. In order to synthesize high-quality CEMRI of equivalent clinical value to real CEMRI, and then promote tumor detection, tripartite-GAN uses a tripartite loss function $L_G$ to train the attention-aware generator. The tripartite loss includes three items corresponding to three robust losses of three tasks. The three tasks are the synthesis of CEMRI, discrimination of CEMRI, and classification of hemangioma and HCC. It means that the generator not only mutually promotes with the discriminator by adversarial strategy but also mutually optimizes with the detector by back-propagation. The tri-partite loss $L_G$ of the generator is shown in Equation 22. The first item is an Euclidean loss $L_E$, which is used to maximize peak signal-to-noise rate (PSNR) for producing high-quality synthetic-CEMRI. The second item is Cross-Entropy loss $L_{CE}$. Like the learning strategy of traditional GAN, we perform the two-participant minimax game between generator and discriminator by using loss $L_{CE}$. The loss $L_{CE}$ is used to minimize the probability of the samples generated by the generator to be recognized while maximizing the probability of the discriminator making a mistake. In other words, through the adversarial learning strategy, the ability of the generator to synthesize CEMRI, and the ability of discriminator to discriminate real or fake are improved simultaneously. The third item is the loss function of $L_{cls}$ for training detector. It helps to optimize the softmax-based tumor classification. The $L_G$ is a weighted sum of three items comprising $L_E$, $L_{CE}$ and $L_{cls}$. The tripartite loss adopted to train the generator has a stable performance, which is formulated as follow:

$$L_G(X, Y, p, u) = \overset{\text{Synthesis loss}}{\overline{L_E(X, Y)}} + \lambda_1 \overset{\text{Discrimination loss}}{\overline{L_{CE}(D(G(X)), 1))}} + \lambda_2 \underset{\text{Classification loss}}{\underline{L_{cls}(p, u)}} \quad (22)$$

where the hyper-parameter $\lambda_1$ and $\lambda_2$ are used for maintaining the weight of joint learning of adversarial learning and back-propagation of $L_{cls}$. The G(X) is the synthetic CEMRI from NCEMRI (X) by the generator, and Y represents the real CEMRI, which is the ground truth. The D(G(X)) is the probability computed by the discriminator, and the value of D(G(X)) was taken into 0 or 1 (0 corresponds to fake, and 1 corresponds to real). Meanwhile, the $L_{CE}$ (D(G(X), 1)) function promotes generator to produce more realistic CEMRI for confusing the discriminator, and it makes the network adversarial-strategy-wise. The loss function $L_E$ and $L_{CE}$ are formulated as follows:

$$L_E(X, Y) = \|Y - G(X)\|_2^2 \quad (23)$$

$$L_{CE}(\hat{Y}, Y) = -\sum_i Y_i \log(\hat{Y}_i) + (1 - Y_i)\log(1 - \hat{Y}_i) \quad (24)$$

where Y is the real CEMRI and
$\hat{Y}$ is the synthetic-CEMRI by the generator, and
the loss function of $L_D$ for training discriminator is defined as:

$$L_D(X,Y) = L_{CE}(D(Y),1) + L_{CE}(D(G(X)),0) \quad (25)$$

that is, the principle of the discriminator is similar to a classifier, one classifier classifies the X as 'real' or 'fake'. The third item $L_{cls}$ of tripartite loss is one part of the detection loss $L_{D\_e}$, which is a multi-task loss to jointly train for tumor classification and bounding-box regression. The multi-task loss $L_{D\_e}$ can be defined as follow:

$$L_{D_e}(p, u, t^u, v) = \overset{\text{Classification loss}}{\overline{L_{cls}(p, u)}} + \lambda_3 \overset{\text{Bounding-box loss}}{\overline{[u \geq 1]L_{box}(t^u, v)}} \quad (26)$$

where the hyper-parameter $\lambda_3$ set to one for maintaining the balance of two tasks losses of $L_{cls}$ and $L_{box}$. The classification loss and bounding-box loss $L_{box}$ are identical as those defined in Fast R-CNN (Girshick, 2015):

$$\begin{cases} L_{cls}(p, u) = -\log p_u \\ L_{box}(t^u, v) = \sum_{i \in [x,y,w,h]} \text{smooth}_{L_1}(t_i^u - v_i) \end{cases} \quad (27)$$

in which $$\text{Smooth}_{L_1}(x) = \begin{cases} 0.5x^2 & \text{if } |x| < 1 \\ |x| - 0.5 & \text{otherwise} \end{cases}, \quad (28)$$

where the p represents the probability distribution of RoI of the tumor, u represents which type of tumor belongs to, the [u≥1] evaluates to 1 when u≥1 and 0 otherwise. $t^u$ is the predicted tuple of bounding-box, and V is a true tuple of the bounding-box.

Advantages of tripartite loss include a stable network performance and also that three tasks of liver CEMRI synthesis, CEMRI discrimination, and tumor detection mutually promote each other in an end-to-end framework.

Materials and Implementation for Experimental Example 2. The experimental datasets used totaled 265 subjects (75 subjects of hemangioma, 138 subjects of HCC, and 52 subjects of health), with each subject having corresponding NCEMRI and CEMRI (after gadolinium CA injection) collected after standard clinical liver MRI examinations. All subjects are provided after approval by the McGill University Health Centre. The corresponding axial T1 FS Pre-Contrast MRI [4 mm; 512×512px] and axial T1 FS Delay MRI [4 mm; 512×512px] are selected for our experiments, in which axial T1 FS Pre-Contrast MRI is used as NCEMRI and axial T1 FS Delay MRI is used as CEMRI (Algorithm 1). Specifically, we perform one 5-fold cross-validation test to train our Tripartite GAN for performance evaluation and comparison. The 265 subjects are divided into 5 groups following random rules grouping, and each group contains 53 subjects. Each of the first four groups contains 15 subjects of hemangioma, 28 subjects of HCC, and 10 subjects of health. And the last group contains 15 subjects of hemangioma, 26 subjects of HCC, and 12 subjects of health. In our experiments, 4 groups were used for training and 1 group was used for testing. Then executed this process 5 times in a loop, until each group is used as the training and testing object. Inspired of (Simon et al., 2019), the values of hyper-parameter $\lambda_1$ in Eq. (22) is set to one, and $\lambda_2$ in Eq. (22) updated according to scheme (Springenberg, J. T., 2015. Unsupervised and semi-supervised learning with categorical generative adversarial networks. arXiv preprint arXiv:1511.06390):

$$\lambda_2 = 1 - \frac{2\omega}{1 + \exp(-10t)} \quad (29)$$

where t is reducing linearly from 1 to 0 during training progress, the value of ω is set to 0.5 smaller than one to raise the priority of high-quality CEMRI synthesis. The $\lambda_2$ gradually grows during training, ensuring the weight of classification increases with the quality of the synthetic-CEMRI. The hyper-parameter $\lambda_3$ in $L_{D\_e}$ (Eg. 26) is set to one in all experiments for maintaining balance of two tasks of bounding-box regression and tumor classification. The Tripartite-GAN is implemented on Pytorch library by using a server platform with four Tesla P100 GPUs.

| Algorithm 1 Tripartite generative adversarial network. |
| --- |
| Input: A dataset of non-contrast MRI x; Ground truth maps of contrast-enhanced MRI y; The label of the types of tumor u; The true tuple of the bounding-box v; The loss balanced weights $\lambda_1, \lambda_2, \lambda_3$; Learning rates $\eta_1, \eta_2, \eta_3$; Mini-batch size n; The number of iterations M; |
| output: Learned parameters $\{\theta_g, \theta_{di}, \theta_{de}, p, t^u\}$; |
| 1:     Initialize the parameters $\{\theta_g, \theta_{di}, \theta_{de}\}$ randomly and construct model graph; |
| 2: for step in M do |
| 3:     fed u, v, $x_n$, $y_n \leftarrow x_n$ and $y_n$ represent the x and y with mini-batch size n; |
| 4:     /* The forward propagation of $G(x_n)$: */ |
| 5:     $X_n$ = Hybrid − Conv($x_n$); |
| 6:     $Atten_n$ = MAM($X_n$) + GAM($X_n$); |
| 7:     $G(x_n)$=Conv3($Atten_n$); |
| 8:     /* The forward propagation of D(•): */ |
| 9:     $D(G(x_n))$ = CNN($G(x_n)$); |
| 10:     $D(y_n)$ = CNN($y_n$); |
| 11:     /* The forward propagation of $D_e$(•): */ |
| 12:     p, $t^u$ = R − CNN($G(x_n)$ + $Atten_n$) |
| 13:     /* The backward propagation of $G(x_n)$: */ |
| 14:     $\theta_g = \theta_g - \eta_1 \nabla (L_E(x_n, y_n) + \lambda_1 L_{CE}(D(G(x_n)), 1) + \lambda_2 L_{cls}(p, u))$ |
| 15:     /* The backward propagation of D(•): */ |
| 16:     $\theta_{di} = \theta_{di} - \eta_2 \nabla (L_{CE}(D(y_n), 1) + L_{CE}(D(G(x_n)), 0))$; |
| 17:     /* The backward propagation of $D_e$(•): */ |
| 18:     $\theta_{de} = \theta_{de} - \eta_3 \nabla L_{D_e}(p, u, t^{u, v})$; |
| 19: end for |

Results for Experimental Example 2

Accurate CEMRI synthesis. Results of synthetic-CEMRI obtained by Tripartite-GAN are shown in FIG. 23. The synthetic-CEMRI has the equivalent value of real CEMRI in clinical diagnosis, in which the differences of specificity between hemangioma and HCC in synthetic-CEMRI are accurate. The area of hemangioma is gradual central filling and bright at the edge, and the area of HCC is entirely or mostly bright through the whole tumor. The results prove that the synthetic-CEMRI has an equal diagnostic value to the real CEMRI (ground truth) via CA injection visually. To quantitatively evaluate the synthetic performance of our Tripartite-GAN, the Tripartite-GAN is compared with three synthesis methods: atlas-based method (Vercauteren, T., Pennec, X., Perchant, A., Ayache, N., 2009. Diffeomorphic demons: Efficient non-parametric image registration. NeuroImage 45, S61-S72), conditional generative adversarial nets (CGANs) (Mirza, M., Osindero, S., 2014. Conditional generative adversarial nets. arXiv preprint arXiv:1411.1784) and Auto-Context based GAN (AC-GAN) (Nie et al., 2018). The results of the comparison are shown in FIG. 24. The pixel intensity curve and zoomed local patches of tumor area show that our Tripartite-GAN is more accurate than three other methods. Furthermore, ablation studies were also performed to prove every part of the newly designed Tripartite-GAN contributes to CEMRI synthesis. The ablation studies include Tripartite-GAN without discriminator (No D), without DAM (No DAM), without MAM (No MAM), without GAM (No GAM), without detector (No $D_e$), without dilated convolution (No Di-con), and without residual learning (No Res-L). The results of ablation studies are shown in FIG. 25. The pixel intensity curve and zoomed local patches of tumor areas show that every part of the newly designed Tripartite-GAN improves CEMRI synthesis. The standard metric of normalized mean absolute error (MAE) and PSNR as the standard of evaluation are used to evaluate the synthetic-CEMRI, which are shown in Table 7. The mean MAE and the mean PSNR of Tripartite-GAN achieve 125.8 and 28.8, which is the best among three synthesis methods. In addition, the evaluation of ablation studies demonstrates that every part of the newly designed Tripartite-GAN improves CEMRI synthesis. Moreover, as shown in Table 8, the paired t-tests between Tripartite-GAN and the other three networks were performed on both PSNR and MAE values. The p −Values (<0.05) of paired t—tests show that the difference between Tripartite-GAN and the other three networks is significant.

TABLE 7

The comparison of Tripartite-GAN and three other methods of image-to-image translation demonstrates that our Tripartite-GAN outperforms the three others on average MAE and PSNR. The ablation studies of No D, No DAM, No MAM, No GAM, No $D_e$, No Di-con, and no Res-L demonstrate that every part of the Tripartite-GAN improves CEMRI synthesis.

|  | MAE | | PSNR | |
| --- | --- | --- | --- | --- |
|  | Mean(std) | Med | Mean(std) | Med |
| Comparison |  |  |  |  |
| Atlas | 190.6(39.2) | 191.2 | 21.8(1.6) | 21.7 |
| CGANs | 177.4(34.8) | 177.8 | 23.3(2.4) | 23.2 |
| ACGAN | 162.1(28.6) | 162.3 | 25.5(2.2) | 25.2 |
| Ablation study |  |  |  |  |
| No D | 167.9(25.3) | 168.6 | 25.9(2.1) | 25.5 |
| No DAM | 159.3(22.1) | 159.1 | 26.1(1.9) | 26.0 |
| No MAM | 157.4(20.4) | 157.0 | 26.5(1.7) | 26.7 |
| No GAM | 155.2(20.0) | 155.5 | 26.7(1.7) | 26.8 |
| No $D_e$ | 152.3(18.9) | 151.9 | 26.9(1.6) | 26.6 |
| No Di-con | 145.7(18.2) | 148.1 | 27.3(1.5) | 27.4 |
| No Res-L | 139.7(17.3) | 140.0 | 27.8(1.4) | 27.6 |
| Tripartite-GAN | 125.8(16.2) | 125.3 | 28.8(1.4) | 28.8 |

TABLE 8 p-Values by performing paired t-tests between Tripartite-GAN and other related networks for both PSNR and MAE values.

|  | MAE | PSNR |
| --- | --- | --- |
| Atlas | <0.01 | <0.01 |
| CGANs | <0.01 | <0.01 |
| ACGAN | <0.05 | <0.05 |

DAM Enhances feature representation: GAM improves the spatial continuity and MAM enhances the detailed synthesis. In order to verify the contribution of the DAM to CEMRI synthesis, we perform the comparison of Tripartite-GAN without DAM and the Tripartite-GAN with DAM. When DAM is removed, the PSNR value decreases from 28.8 to 26.1. As the first row shows in FIG. 26, subject1 demonstrates that Tripartite-GAN with DAM outperforms Tripartite-GAN without DAM in the detailed synthesis of anatomy specificity and the spatial continuity. To verify the respective contributions of GAM and MAM to CEMRI synthesis, we perform two comparisons of evaluating the contribution of MAM and GAM independently. One of the two comparisons is between Tripartite-GAN without GAM and our Tripartite-GAN. The other is between Tripartite-GAN without MAM and our Tripartite-GAN. When MAM is removed, the PSNR value decreases from 28.8 to 26.5. And when GAM is removed, the PSNR value decreases from 28.8 to 26.7. As the last two rows in FIG. 26 show, subject2 demonstrates that GAM improves the spatial continuity of CEMRI synthesis and subject3 demonstrates that MAM enhances the detailed feature extraction to improve the discrimination of hemangioma and HCC. These results prove that the MAM enhances the detailed synthesis of anatomy specificity, and the GAM improves the spatial continuity effectively. In order to clearly see the specific contributions of MAM and GAM, FIG. 27 shows the feature maps of Tripartite-GAN without GAM, Tripartite-GAN without MAM, and our Tripartite-GAN (with DAM), respectively. We can see the GAM enhances the spatial feature extraction (especially for the feature extraction at edges) by comparing the dark grey window/box in the feature maps. And we can see the MAM enhances the detailed feature extraction by comparing the light grey window/box in the feature maps. It is clear that GAM helps our Tripartite-GAN adaptively aggregate long-range contextual information, which improves the spatial continuity of synthetic CEMRI. And MAM helps our Tripartite-GAN enhance detailed feature extraction, which ensures the accurate synthesis of the specificity of tumor in synthetic CEMRI. The visualization of synthesis results and zoomed local patches of tumor area are shown in the last two columns in FIG. 27. It is clear that MAM helps our Tripartite-GAN enhance detailed synthesis, and GAM helps our Tripartite-GAN improve the spatial continuity of synthetic CEMRI.

Hybrid convolution for increasing the effective receptive field. In order to verify the advantages of our designed hybrid convolution for CEMRI synthesis, we perform the comparison between a traditional FCN (No Di-con) with the same parameter settings of dilated convolution layers and our Tripartite-GAN. The synthesis results are shown in FIG. 25. And the effect of the hybrid convolution operation is quantitatively evaluated. The PSNR value of synthetic CEMRI by using No Di-con Tripartite-GAN is 27.3, and the PSNR value of synthetic CEMRI by using our Tripartite-GAN is 28.8. These results prove that expansion of the receptive field by hybrid convolution makes the generator powerful in feature extraction.

Residual learning benefits the training of generator. In order to verify the effect of the residual learning to CEMRI synthesis, we perform the comparison between Tripartite-GAN without residual learning and our Tripartite-GAN. The synthesis results are shown in FIG. 25. And the PSNR value of synthetic CEMRI from Tripartite-GAN without residual learning is 27.8, while the corresponding PSNR value for Tripartite-GAN with residual learning is 28.8. Moreover, the visualization of the training loss is shown in FIG. 28, in which the Tripartite-GAN without residual learning and Tripartite-GAN with residual learning are demonstrated by the light grey curve and dark grey curve, respectively. It is clear that Tripartite-GAN with residual learning outperforms the Tripartite-GAN without residual learning. And the results prove that residual learning helps the network train faster and achieve lower synthesis error.

Adversarial strategy encourages the high-quality CEMRI synthesis. In order to verify the contribution of the adversarial strategy to CEMRI synthesis, we performed a comparison between Tripartite-GAN without discriminator and our optimized Tripartite-GAN, which are shown in FIG. 25. The synthetic CEMRI of Tripartite-GAN has fewer artifacts than the Tripartite-GAN without the adversarial strategy. The quantitative evaluation shows that the PSNR value decreases from 28.8 to 25.9 when discriminator is removed. And these results prove that the discriminator makes the framework of Tripartite-GAN adversarial-strategy-aware, which eagerly improves the authenticity of synthetic-CEMRI of the generator.

Back-propagation of classification loss urges the more accurate CEMRI synthesis. In order to verify the contribution of the detector to the generator, we perform the comparison between Tripartite-GAN without the detector and our optimized Tripartite-GAN, which are shown in FIG. 25. We can clearly see that the optimized Tripartite-GAN outperforms the Tripartite-GAN without the detector, especially for the specificity learning of the tumor. The PSNR value de-creases from 28.8 to 26.9 when the detector is removed. These results prove that the detector reinforced the performance of the attention-aware generator via the back-propagation of $L_{cls}$. The detector prompts the generator to focus on the specificity of two types of tumors. Meanwhile, the synthetic CEMRI generated by the attention-aware generator has distinct specificity, which facilitates the detector for accurate detection of tumors.

As shown in FIG. 25, we perform a comparison by using the ablation study, which verifies the contribution of the discriminator to the CEMRI synthesis, the contribution of the DAM to the CEMRI synthesis, the contribution of the detector to the CEMRI synthesis, the contribution of dilated convolution to the CEMRI synthesis, and the contribution of residual learning to the CEMRI synthesis. All of the pixel intensity curves and zoomed local patches of tumor area proved that these modules of Tripartite GAN have a positive effect on liver CEMRI synthesis, especially in improving the accuracy of the synthesis of tumor areas.

Accuracy tumor detection. Results of tumor detection via detector from Tripartite-GAN show that our optimized Tripartite-GAN has a high and stable accuracy of 89.4%. To quantitatively evaluate the performance of detection of our Tripartite-GAN, the Tripartite-GAN was compared with three detection methods: U-Net based FCN (Dong, H., Yang, G., Liu, F., Mo, Y., Guo, Y., 2017. Automatic brain tumor detection and segmentation using u-net based fully convolutional networks, in: annual conference on medical image understanding and analysis, pp. 506-517), modified Faster-R-CNN (Akselrod-Ballin, A., Karlinsky, L., Alpert, S., Hasoul, S., Ben-Ari, R., Barkan, E., 2016. A region based convolutional network for tumor detection and classification in breast mammography, in: Deep learning and data labeling for medical applications. Springer, pp. 197-205.) and combination of fuzzy c-means and SVM(FZM-SVM) (Singh, A., et al., 2015. Detection of brain tumor in MRI images, using combination of fuzzy c-means and svm, in: 2015 2nd International Conference on Signal Processing and Integrated Networks (SPIN), IEEE. pp. 98-102). Results of the comparison of Tripartite-GAN and the other three methods of detection are shown in Table 9, which demonstrates that our Tripartite-GAN outperforms the three other methods of detection. Furthermore, we also perform the ablation studies to prove every part of the newly designed Tripartite-GAN contributes to tumor detection. The results of ablation studies are shown in Table 10. The ablation studies include Tripartite-GAN without generator and discriminator (No G+No D), without discriminator (No D), without DAM (No DAM), without MAM (No MAM), without GAM (No GAM), without adding attention maps into detector (No atten), without dilated convolution (No Di-con), and without residual learning (No Res-L). Results of ablation studies demonstrate that every part of the newly designed Tripartite-GAN improves tumor detection. We also evaluated the accuracy, sensitivity, and specificity of tumor detection results in Tables 11, 12 and 13. We defined healthy subjects as positive and hemangioma as negative in Table 11. We defined healthy subjects as positive and HCC as negative in Table 12. And we defined hemangioma as positive and HCC as negative in Table 13. The evaluation results demonstrate that our Tripartite-GAN outperforms three other detection methods. And the ablation study of Tripartite-GAN demonstrates that every part of the newly designed Tripartite-GAN contributes to tumor detection. The "upper bound" of detection results in the last column/row of these five tables (last columns of Tables 9-10 and last rows of Tables 11-13) represent the detection results computed directly from ground truth CEMRI images. It demonstrates that our synthetic CEMRI images performed close to the real CEMRI in tumor detection. The evaluation criterion of accuracy, sensitivity, and specificity are defined as follow:

$$\text{Accuracy} = \frac{TP + TN}{TP + FP + TN + FN} \quad (30)$$

$$\text{Sensitivity. } TPR = \frac{TP}{TP + FN} \quad (31)$$

$$\text{Specificity. } TNR = \frac{TN}{FP + TN} \quad (32)$$

where the sensitivity and specificity are equivalent to the true positive rate (TPR) and the true negative rate (TNR), respectively. The TP, FP, TN, and FN denotes the true positive, false positive, true negative, and false negative measurements, respectively.

Adding attention maps into detector improves the performance of tumor detection. In order to verify the attention maps have the potential to detect tumors and the contribution of adding attention maps into the detector, we perform the comparison among three different detectors as follows: 1) Using the attention maps instead of feature maps from VGG-16 for the box generation and tumor classification by R-CNN. 2) Using the VGG-16-based model to obtain feature maps without the help of attention maps for box generation and tumor classification by R-CNN. 3) Using the VGG-16-based model to obtain feature maps with the help of attention maps for box generation and tumor classification by R-CNN (our detector as shown in FIG. 22). The results of the comparison are shown in FIG. 29, the columns 2, 3, and 4 correspond to the detector (1), (2) and (3) mentioned above, respectively. It is clear that attention maps have the potential to detect tumors but not accurately. Attention maps not only focus on the tumor but pay attention to extract all features of all anatomy structure in liver MRI for entire liver MRI synthesis. Both the feature maps of VGG-16 without attention maps and the feature maps of VGG-16 with attention maps focus on tumor information, but the characterizations of tumors in VGG-16 with attention maps are more accurate and detailed than without attention maps. The detection results of three different detectors demonstrate that the attention map added into VGG-16 in the manner of residual connection improves R-CNN-based detector to detect the tumor.

TABLE 9

The comparison of Tripartite-GAN and three other methods of detection, which demonstrates that our Tripartite-GAN outperforms three other detection methods. The upper bound of Tripartite-GAN demonstrates that our synthetic CEMRI images performed close to the real CEMRI in tumor detection.

| Method | FZM-SVM | Modified Faster-RCNN | U-net based FCN | Tripartite-GAN | Tripartite-GAN (upper bound) |
|---|---|---|---|---|---|
| Accuracy | 78.1% | 79.2% | 79.2% | 89.4% | 90.9% |

TABLE 10

The ablation studies demonstrate that every part of the newly designed Tripartite-GAN contributes to tumor detection. The upper bound of Tripartite-GAN demonstrates that our synthetic CEMRI images performed close to the real CEMRI in tumor detection.

| Method | No G + D | No D | No DAM | No MAM | No GAM | No Atten | No Di-Con | No Res-L | Tripartite GAN | Tripartite-GAN (upper bound) |
|---|---|---|---|---|---|---|---|---|---|---|
| Accuracy | 80.0% | 81.1% | 83.0% | 83.8% | 84.9% | 86.4% | 87.5% | 88.3% | 89.4% | 90.9% |

TABLE 11

When we defined healthy subjects as positive and hemangioma as negative, the comparison of Tripartite-GAN and three other methods of detection demonstrates that our Tripartite-GAN outperforms three other detection methods. The ablation studies demonstrate that every part of the newly designed Tripartite-GAN contributes to tumor detection.

| | health(P)/Hemangioma(N) | | |
|---|---|---|---|
| Method | Accuracy | Sensitivity | Specificity |
| Comparison | | | |
| FZM-SVM | 78.0 ± 1.3% | 87.0 ± 2.6% | 92.2 ± 1.4% |
| Modified Faster-RCNN | 78.7 ± 1.0% | 87.2 ± 2.2% | 92.2 ± 1.4% |
| U-Net based FCN | 79.5 ± 1.1% | 89.1 ± 2.1% | 92.3 ± 1.2% |

TABLE 11-continued

When we defined healthy subjects as positive and hemangioma as negative, the comparison of Tripartite-GAN and three other methods of detection demonstrates that our Tripartite-GAN outperforms three other detection methods. The ablation studies demonstrate that every part of the newly designed Tripartite-GAN contributes to tumor detection.

| | health(P)/Hemangioma(N) | | |
|---|---|---|---|
| Method | Accuracy | Sensitivity | Specificity |
| Ablation study | | | |
| No G + No D | 80.3 ± 1.2% | 89.4 ± 2.0% | 92.3 ± 1.3% |
| No D | 81.1 ± 1.0% | 89.4 ± 2.0% | 92.4 ± 1.2% |
| No DAM | 83.5 ± 0.8% | 91.5 ± 1.8% | 94.0 ± 1.0% |
| No MAM | 84.3 ± 0.8% | 91.5 ± 1.8% | 95.5 ± 1.0% |
| No GAM | 85.8 ± 0.8% | 93.6 ± 1.7% | 95.6 ± 0.9% |
| No Atten | 87.4 ± 0.7% | 95.7 ± 1.5% | 95.7 ± 0.8% |
| No Di-con | 89.0 ± 0.6% | 95.8 ± 1.6% | 97.1 ± 0.8% |
| No Res-L | 90.0 ± 0.7% | 95.8 ± 1.5% | 98.6 ± 0.9% |
| Tripartite-GAN | 91.3 ± 0.6% | 95.9 ± 1.3% | 98.6 ± 0.7% |
| Tripartite-GAN (upper bound) | 92.9 ± 0.6% | 96.0 ± 1.2% | 98.6 ± 0.7% |

TABLE 12

When we defined healthy subjects as positive and HCC as negative, the comparison of Tripartite-GAN and three other methods of detection demonstrates that our Tripartite-GAN outperforms three other detection methods. The ablation studies demonstrate that every part of the newly designed Tripartite-GAN contributes to tumor detection.

| | health(P)/HCC(N) | | |
|---|---|---|---|
| Method | Accuracy | Sensitivity | Specificity |
| Comparison | | | |
| FZM-SVM | 77.9 ± 1.2% | 87.0 ± 2.2% | 93.9 ± 1.2% |
| Modified Faster-RCNN | 79.5 ± 1.1% | 89.1 ± 2.0% | 94.8 ± 1.0% |
| U-Net based FCN | 78.9 ± 1.1% | 87.2 ± 2.1% | 94.0 ± 1.1% |
| Ablation study | | | |
| No G + No D | 80.0 ± 1.0% | 89.4 ± 1.9% | 94.8 ± 1.0% |
| No D | 81.1 ± 0.9% | 89.4 ± 1.8% | 94.9 ± 0.9% |
| No DAM | 82.6 ± 0.8% | 90.0 ± 1.6% | 95.0 ± 0.8% |
| No MAM | 83.2 ± 0.8% | 89.6 ± 1.7% | 95.8 ± 0.7% |
| No GAM | 84.2 ± 0.8% | 89.8 ± 1.7% | 95.9 ± 0.7% |
| No Atten | 85.3 ± 0.7% | 90.0 ± 1.5% | 95.9 ± 0.6% |
| No Di-con | 86.8 ± 0.7% | 92.0 ± 1.5% | 96.7 ± 0.7% |
| No Res-L | 87.4 ± 0.8% | 92.0 ± 1.6% | 96.8 ± 0.7% |
| Tripartite-GAN | 88.4 ± 0.6% | 94.0 ± 1.2% | 96.8 ± 0.6% |
| Tripartite-GAN (upper bound) | 90.0 ± 0.6% | 96.0 ± 1.1% | 97.6 ± 0.5% |

TABLE 13

When we defined hemangioma as positive and HCC as negative, the comparison of Tripartite-GAN and three other methods of detection demonstrates that our Tripartite-GAN outperforms three other detection methods. The ablation studies demonstrate that every part of the newly designed Tripartite-GAN contributes to tumor detection.

| | Hemangioma(P)/HCC(N) | | |
|---|---|---|---|
| Method | Accuracy | Sensitivity | Specificity |
| Comparison | | | |
| FZM-SVM | 78.4 ± 1.2% | 84.3 ± 1.7% | 82.4 ± 1.5% |
| Modified Faster-RCNN | 79.3 ± 1.0% | 84.3 ± 1.5% | 83.3 ± 1.5% |
| U-Net based FCN | 79.3 ± 1.1% | 85.7 ± 1.5% | 83.2 ± 1.5% |
| Ablation study | | | |
| No G + No D | 79.8 ± 0.8% | 85.7 ± 1.3% | 83.3 ± 1.3% |
| No D | 81.2 ± 0.7% | 87.1 ± 1.2% | 84.8 ± 1.3% |
| No DAM | 83.6 ± 0.7% | 88.7 ± 1.2% | 86.4 ± 1.2% |
| No MAM | 84.0 ± 0.7% | 88.9 ± 1.2% | 86.5 ± 1.2% |
| No GAM | 85.0 ± 0.6% | 90.3 ± 1.1% | 87.2 ± 1.1% |
| No Atten | 85.9 ± 0.7% | 91.7 ± 1.1% | 88.0 ± 1.0% |
| No Di-con | 87.3 ± 0.6% | 91.8 ± 1.0% | 88.8 ± 1.1% |
| No Res-L | 88.3 ± 0.6% | 91.9 ± 1.0% | 89.6 ± 1.0% |
| Tripartite-GAN | 89.2 ± 0.5% | 93.2 ± 0.8% | 90.3 ± 0.9% |
| Tripartite-GAN (upper bound) | 90.6 ± 0.5% | 94.6 ± 0.6% | 91.1 ± 0.8% |

REFERENCES FOR EXPERIMENTAL EXAMPLE 2

Akselrod-Ballin, A., Karlinsky, L., Alpert, S., Hasoul, S., Ben-Ari, R., Barkan, E., 2016. A region based convolutional network for tumor detection and classification in breast mammography. In: Deep Learning and Data Labeling for Medical Applications. Springer, pp. 197-205.

Beers, A., Brown, J., Chang, K., Campbell, J. P., Ostmo, S., Chiang, M. F., Kalpathy-Cramer, J., 2018. High-resolution medical image synthesis using progressively grown generative adversarial networks. arXiv:1805.03144.

Ben-Cohen, A., Klang, E., Raskin, S. P., Soffer, S., Ben-Haim, S., Konen, E., Amitai, M. M., Greenspan, H., 2019. Cross-modality synthesis from CT to PET using FCN and GAN networks for improved automated lesion detection. Eng. Appl. Artif. Intell. 78, 186-194.

Chongxuan, L., Xu, T., Zhu, J., Zhang, B., 2017. Triple generative adversarial nets. In: Advances in Neural Information Processing Systems, pp. 4088-4098.

Costa, P., Galdran, A., Meyer, M. I., Niemeijer, M., Abramoff, M., Mendonca, A. M., Campilho, A., 2017. End-to-end adversarial retinal image synthesis. IEEE Trans. Med. Imaging 37 (3), 781-791.

Digumarthy, S. R., Sahani, D. V., Saini, S., 2005. MRI in detection of hepatocellular carcinoma (HCC). Cancer Imaging 5 (1), 20.

Dong, H., Yang, G., Liu, F., Mo, Y., Guo, Y., 2017. Automatic brain tumor detection and segmentation using u-net based fully convolutional networks. In: Annual Conference on Medical Image Understanding and Analysis, pp. 506-517.

Emami, H., Dong, M., Nejad-Davarani, S. P., Glide-Hurst, C. K., 2018. Generating synthetic CTs from magnetic resonance images using generative adversarial networks. Med. Phys. 45 (8), 3627-3636.

Frid-Adar, M., Diamant, I., Klang, E., Amitai, M., Goldberger, J., Greenspan, H., 2018. GAN-based synthetic medical image augmentation for increased CNN performance in liver lesion classification. Neurocomputing 321, 321-331.

Fu, J., Liu, J., Tian, H., Li, Y., Bao, Y., Fang, Z., Lu, H., 2019. Dual attention network for scene segmentation. In: Proceedings of the IEEE Conference on Computer Vision and Pattern Recognition, pp. 3146-3154.

Girshick, R., 2015. Fast R-CNN. In: Proceedings of the IEEE International conference on Computer Vision, pp. 1440-1448.

Goodfellow, I., Pouget-Abadie, J., Mirza, M., Xu, B., Warde-Farley, D., Ozair, S., Courville, A., Bengio, Y., 2014. Generative adversarial nets. In: Advances in Neural Information Processing Systems, pp. 2672-2680.

Halavaara, J., Breuer, J., Ayuso, C., Balzer, T., Bellin, M.-F., Blomqvist, L., Carter, R., Grazioli, L., Hammerstingl, R., Huppertz, A., et al., 2006. Liver tumor characterization: comparison between liver-specific gadoxetic acid disodium-enhanced MRI and biphasic CT-A multicenter trial. J. Comput. Assist. Tomogr. 30 (3), 345-354.

He, K., Zhang, X., Ren, S., Sun, J., 2016. Deep residual learning for image recognition. In: Proceedings of the IEEE Conference on Computer Vision and Pattern Recognition, pp. 770-778.

Hu, H., Gu, J., Zhang, Z., Dai, J., Wei, Y., 2018. Relation networks for object detection. In: Proceedings of the IEEE Conference on Computer Vision and Pattern Recognition, pp. 3588-3597.

Hu, J., Shen, L., Sun, G., 2018. Squeeze-and-excitation networks. In: Proceedings of the IEEE Conference on Computer Vision and Pattern Recognition, pp. 7132-7141.

Idée, J.-M., Port, M., Raynal, I., Schaefer, M., Le Greneur, S., Corot, C., 2006. Clinical and biological consequences of transmetallation induced by contrast agents for magnetic resonance imaging: a review. Fundam. Clin. Pharmacol. 20 (6), 563-576.

Korkinof, D., Rijken, T., O'Neill, M., Yearsley, J., Harvey, H., Glocker, B., 2018. High-resolution mammogram synthesis using progressive generative adversarial networks. arXiv:1807.03401.

Low, R. N., 2007. Abdominal MRI advances in the detection of liver tumours and characterisation. Lancet Oncol. 8 (6), 525-535.

Mahasseni, B., Lam, M., Todorovic, S., 2017. Unsupervised video summarization with adversarial LSTM networks. In: Proceedings of the IEEE Conference on Computer Vision and Pattern Recognition, pp. 202-211.

Marckmann, P., Skov, L., Rossen, K., Dupont, A., Damholt, M. B., Heaf, J. G., Thom-sen, H. S., 2006. Nephrogenic systemic fibrosis: suspected causative role of gado-diamide used for contrast-enhanced magnetic resonance imaging. J. Am. Soc. Nephrol. 17 (9), 2359-2362.

Mirza, M., Osindero, S., 2014. Conditional generative adversarial nets. arXiv:1411.1784.

Nie, D., Trullo, R., Lian, J., Wang, L., Petitjean, C., Ruan, S., Wang, Q., Shen, D., 2018. Medical image synthesis with deep convolutional adversarial networks. IEEE Trans. Biomed. Eng. 65 (12), 2720-2730.

Peng, C., Zhang, X., Yu, G., Luo, G., Sun, J., 2017. Large kernel matters—improve semantic segmentation by global convolutional network. In: Proceedings of the IEEE Conference on Computer Vision and Pattern Recognition, pp. 4353-4361.

Ren, S., He, K., Girshick, R., Sun, J., 2015. Faster R-CNN: towards real-time object detection with region proposal networks. In: Advances in Neural Information Processing Systems, pp. 91-99.

Shen, Y., Luo, P., Yan, J., Wang, X., Tang, X., 2018. FaceID-GAN: Learning a symmetry three-player GAN for identity-preserving face synthesis. In: Proceedings of the IEEE Conference on Computer Vision and Pattern Recognition, pp. 821-830.

Simon, V., Bert, D. B., Davy, N., Luc, V. G., 2019. A three-player GAN: generating hard samples to improve classification networks. arXiv:1903.03496.

Simonyan, K., Zisserman, A., 2014. Very deep convolutional networks for large-scale image recognition. arXiv:1409.1556.

Singh, A., et al., 2015. Detection of brain tumor in MRI images, using combination of fuzzy C-means and SVM. In: 2015 2nd International Conference on Signal Processing and Integrated Networks (SPIN). IEEE, pp. 98-102.

Son, J., Park, S. J., Jung, K.-H., 2017. Retinal vessel segmentation in fundoscopic images with generative adversarial networks. arXiv:1706.09318.

Springenberg, J. T., 2015. Unsupervised and semi-supervised learning with categorical generative adversarial networks. arXiv:1511.06390.

Vaswani, A., Shazeer, N., Parmar, N., Uszkoreit, J., Jones, L., Gomez, A. N., Kaiser, L., Polosukhin, I., 2017. Attention is all you need. In: Advances in Neural Information Processing Systems, pp. 5998-6008.

Vercauteren, T., Pennec, X., Perchant, A., Ayache, N., 2009. Diffeomorphic demons: efficient non-parametric image registration. NeuroImage 45 (1), S61-S72.

Wang, P., Chen, P., Yuan, Y., Liu, D., Huang, Z., Hou, X., Cottrell, G., 2018. Understanding convolution for semantic segmentation. In: 2018 IEEE Winter Conference on Applications of Computer Vision (WACV). IEEE, pp. 1451-1460.

Wolterink, J. M., Dinkla, A. M., Savenije, M. H., Seevinck, P. R., van den Berg, C. A., Išgum, I., 2017. Deep MR to CT synthesis using unpaired data. In: International Workshop on Simulation and Synthesis in Medical Imaging. Springer, pp. 14-23.

Yang, W., Zhong, L., Chen, Y., Lin, L., Lu, Z., Liu, S., Wu, Y., Feng, Q., Chen, W., 2018. Predicting CT image from MRI data through feature matching with learned nonlinear local descriptors. IEEE Trans. Med. Imaging 37 (4), 977-987.

Zhang, H., Goodfellow, I., Metaxas, D., Odena, A., 2018. Self-attention generative adversarial networks. arXiv:1805.08318.

Zhao, H., Shi, J., Qi, X., Wang, X., Jia, J., 2017. Pyramid scene parsing network. In: Proceedings of the IEEE Conference on Computer Vision and Pattern Recognition, pp. 2881-2890.

Zhao, S., Wu, X., Chen, B., Li, S., 2019. Automatic spondylolisthesis grading from MRIs across modalities using faster adversarial recognition network. Med. Image Anal. 101533.

An illustrative version and several variants of synthesis of a medical CA-free-AI-enhanced image and associated diagnostic analysis have been described above without any intended loss of generality. Further examples of modifications and variation are now provided. Still further variants, modifications and combinations thereof are contemplated and will be apparent to the person of skill in the art. It is to be understood that illustrative variants or modifications are provided for the purpose of enhancing the understanding of the person of skill in the art and are not intended as limiting statements.

For example, the simultaneous performance of a medical CA-free-AI-enhanced image synthesis task and medical diagnostic image analysis task described herein are not limited to MR scanning, and can readily be adapted to other imaging modalities that have sufficient spatial resolution for diagnostic imaging, including Ultrasound and computed tomography (CT) and other X-ray imaging techniques (ie., X-ray imaging techniques other than CT imaging), including for example fluoroscopy. Medical sonographic examination is an ultrasound-based diagnostic medical imaging technique used to visualize muscles, tendons, and many internal organs to capture their size, structure and any pathological lesions, often with real time tomographic images. Ultrasonic images, also known as sonograms, are made by sending pulses of ultrasound into tissue using a probe; the ultrasound pulses echo off tissues with different reflection properties and are recorded and displayed as an image. X-ray based scans are a form of medical imaging comprising transmission of a high frequency electromagnetic signal that becomes attenuated as it passes through the body of a subject with the remaining signal captured by a detector for subsequent analysis. To improve image clarity, ultrasound scans and X-ray scans and MRI scans involve the oral or intravenous administration of a contrast agent to a patient. Contrast agents for X-ray imaging techniques include for example iodine-based contrast agents or barium-based contrast agents. Contrast agents for MRI imaging techniques include for example gadolinium-based contrast agents. Contrast agents for ultrasound imaging include for example microbubbles. Scan data acquired from X-ray based scanner devices/systems are often referenced as scan data or projection data interchangeably, while scan data acquired from MRI scanner devices/systems are typically referenced as scan data and ultrasound acquired data is also typically referenced as scan data. Thus, the term scan data is understood to encompass both the terms scan data and projection data.

Contrast agents (also referred to as tracers) for various imaging modalities are established in the current literature and continue to be an active area of development for new alternatives. The simultaneous performance of a medical CA-free-AI-enhanced image synthesis task and medical diagnostic image analysis task described herein may accommodate any suitable combination of contrast agent and imaging modality provided that the imaging modality affords sufficient spatial resolution for medical diagnostic imaging.

As another example, simultaneous performance of a medical CA-free-AI-enhanced image synthesis task and medical diagnostic image analysis task described herein may be implemented with various hardware configurations with a specific hardware configuration suited to characteristics of a desired application.

For example, hardware may be configured for local processing. In a local processing configuration the processing of data is done at the site of image acquisition. This reduces the size of the data exchanged with a remote server.

In another example, hardware may be configured for remote processing of images. This is a cost-effective solution as hardware that process neural network data are relatively expensive and have a relatively large power consumption. Therefore, sending the data to the remote server for processing can reduce cost.

In a further example, hardware may be configured for hybrid processing. In a hybrid configuration, an initial data processing is done locally before sending to a remote server.

Any suitable combination of hardware components may be incorporated to implement the method or system described herein including for example: MRI scanner, power source, processor (CPU alone OR CPU+GPU OR GPU alone OR any kind of device that can process large volumes of images), memory, connectivity (Wifi, bluetooth, SIM Card), and the like.

For image acquisition any suitable MRI scanner is used to capture scan data at settings adapted to a particular diagnostic analysis task.

For image reconstruction, any reconstruction algorithm suited to reconstruct MRI scan data may be used.

For image processing any suitable processing technique may be used. The processing technique will be chosen to process image data to improve training and/or analysis by a machine learning model, for example a neural network.

Machine learning models may include, for example, a neural network (such as an artificial neural network, or in a more specific example, a convolutional neural network, examples of which have been detailed in above described experimental exemplifications), a Bayesian network, a hidden Markov model, a Markov decision process, a logistic regression function, a support vector machine, a suitable statistical machine learning algorithm, and/or a heuristic machine learning system. A machine learning model can be trained by providing training data as a training input using any suitable training technique, including for example, unsupervised learning, supervised learning, semi-supervised learning, weakly-supervised learning, deep learning, reinforcement learning, deep reinforcement learning, transfer learning, incremental learning, and/or curriculum learning techniques.

Unsupervised learning is a type of machine learning that looks for previously undetected patterns in a data set with no pre-existing labels and with a minimum of human supervision. In contrast to supervised learning that usually makes use of human-labeled data, unsupervised learning, also known as self-organization allows for modeling of probability densities over inputs without referencing corresponding labels for the inputs. Unsupervised learning algorithms are suitable for tasks where the data has distinguishable inherent patterns. In supervised learning, machine learning models determine one or more output inferences based on provided training data, and the output inferences are either accepted or corrected based on correct results associated with the training data.

Semi-supervised learning makes use of supervised and unsupervised techniques. Semi-supervised learning can involve having correct results for part, but not all, of training data. Therefore, semi-supervised learning typically involves partial inputs having corresponding labels, and other partial inputs having unknown labels (or no labels), and semi-supervised learning algorithms aim to use both types of inputs to learn a mapping from the input to the correct label. Semi-supervised learning algorithms can be suited for tasks where the label is difficult to annotate.

Weakly-supervised learning uses input having a corresponding weak label. The weak label means it provides less information compared with the label that would be used in supervised learning. Weakly-supervised learning algorithms can involve mapping the input to a more specific label. For example, in a pixel-level object segmentation task, the provided weak label is bounding-boxes of desirable objects, and in this example the weak label is not so accurate as to indicate the class of every pixel, but it indicates the object location and size. Thus, the weakly-supervised learning algorithms try to use weak labels to exploit the input inherent features, thereby accomplishing a desired task.

Deep learning is a subset of machine learning in AI, which imitates the human brain working process to learn to build a non-linear mapping between inputs and the desired output by training multiple node layers of neural networks. The training procedure of deep learning is an iterative process: for example, a convolution neural network (CNN) predicts an output according to an input (forward propagation); then a loss function evaluates the error between the predicted output and the desired output; deep learning adjusts the CNN's parameters through back propagation based on the error to enable its prediction to approach the desired output in the next forward propagation. Repeating the training process, after the error between the predicted output and the desired output is less than a threshold, deep learning is able to predict the output for a new same category input.

Reinforcement learning can involve providing a machine learning model with a reward signal for a correct output inference; for example, the reward signal can be a numerical value. During reinforcement learning, a machine learning model can output an inference and receive a reward signal in response, where the machine learning model is configured to try to maximize the the reward signal, for example a numerical value of the reward signal. In more specific terms, reinforcement learning deploys an agent to interact with an environment in a manner that maximizes long-term rewards—the agent is not taught to complete a task, but instead learns to accomplish a task through the reward signal feedback. Reinforcement learning can be illustrated by considering elements of state, action, and reward: the state is used to describe the whole of the environment/task and the agent; the action indicates the role the agent exerts on the environment/task, where the agent iteratively observes the state of the task and selects a specific action to change the state of the task; and in each learning cycle a reward function gives the agent a reward signal for the current iteration and the environment/task provides a new state for the next iteration. The aim of reinforcement learning is to learn the mapping from state to action, that is, what action should be selected in the current state to maximize the reward, which becomes the learned policy/strategy.

Deep reinforcement learning integrates both deep learning and reinforcement learning, thus combining their advantages. Performance of reinforcement learning can depend on the process of fitting action-value functions or strategy parameterization, where the widespread use of function approximators enables reinforcement learning to be used in complex problems. While deep learning has been deployed as function approximators in supervised learning and they are derivable. Thus, in context of deep reinforcement learning, deep learning can be considered to enlarge the application range of reinforcement learning and improve its performance.

Transfer learning is a subfield of machine learning that focuses on storing knowledge gained while solving one problem and applying it to a different but related problem Transfer learning techniques can involve a trained machine learning model being pre-trained on a first set of data relating to a first task and then additionally trained using a second set of training data relating to a second task.

Incremental learning techniques can involve providing a trained machine learning model with input data that is used to continuously extend knowledge of the trained machine learning model. Curriculum learning techniques can involve a machine learning model trained with training data arranged in a particular order, such as providing relatively-easy training examples first and proceeding with progressively more difficult training examples e.g., analogously to a curriculum or course of study at a school. Other techniques for machine learning model are available.

Detailed examples of a deep reinforcement learning based approach to dual tasks of medical image synthesis and medical image diagnostic analysis are provided to illustrate feasibility of alternatives to the above-described GAN exemplifications.

A first detailed example of a deep reinforcement learning (DRL) approach provides a Weakly-Supervised Teacher-Student network (WSTS) to address tumor segmentation in a non-enhanced image by additionally leveraging box-level-labeled data. To this purpose, WSTS employs a weakly-supervised teacher-student framework (TCH-ST). In the training stage, WSTS explores the tumor location to learn tumor spatial feature in the contrast-enhanced MRI image and predicts an accurate pixel-level tumor mask for the box-level-labeled data as tumor shape feature. With the tumor spatial and shape features as guidance, WSTS learns to detect and segment the tumor in the non-enhanced MRI image. Thus in the testing stage, WSTS is able to detect and segment the tumor from the non-enhanced image without the assistance of the contrast-enhanced image. To determine the tumor location and size correctly WSTS includes a Dual-strategy DRL (DDRL). The DDRL develops two tumor detection strategies to jointly determine the tumor location in the contrast-enhanced image by introducing a relative-entropy bias in the DRL. By following the detection strategies, WSTS is able to determine the tumor location in the non-enhanced image. To predict the tumor mask for the box-level-labeled data, WSTS includes an Uncertainty-Sifting Self-Ensembling (USSE). The USSE utilizes the limited pixel-level-labeled data and additional box-level-labeled data to predict the tumor accurately by evaluating the prediction reliability with a Multi-scale Uncertainty-estimation. By taking the tumor prediction as a pseudo label (additional to the manual pixel-level-label), the tumor segmentation in the non-enhanced image is thus improved.

Comparing the data flow of the Teacher Module to the Student Module, the WSTS leverages the Teacher Module to exploit the tumor knowledge in the contrast-enhanced image as guidance to train a Student Module, so that the Student Module is able to detect and segment the tumor from the non-enhanced image independently in the testing stage. The Teacher Module deploys the Dual-strategy DRL (DDRL) and the Uncertainty-Sifting Self-Ensembling (USSE) to obtain a tumor mask in the contrast-enhanced image. The DDRL coordinates two Relative-entropy-biased Actor-Critics (RACs) to develop tumor detection strategies and determine the tumor location. The DDRL coordinates cooperative interaction between the two RACs to self-learn the tumor detection strategies and fuses their detection results to output a fused tumor detection (for example, a union of two boxes respectively outputted from the two RACs). The DDRL coordinates each RAC to explore various strategies by maximizing the entropy of explored strategy distribution; and to take the other RAC's decision into consideration when learning its own strategy by maximizing the relative entropy between the developed strategies. The USSE integrates a Multi-scale Uncertainty-estimation (MU) with Self-Ensembling (SE) to predict a pixel-level tumor mask for the box-level-label data. The Student Module employs a Student DDRL (SDDRL) and a Student DenseUNet (SDUNet) to learn tumor segmentation under the guidance of the Teacher Module in the non-enhanced image. The SDDRL imitates the DDRL to learn tumor detection strategies by training two RACs incorporated within the SDDRL by imitating the Teacher Module's learned strategies. The SDUNet learns to segment tumor tissue under supervision of the USSE; the SDUNet utilizes the USSE's tumor mask as a pseudo-pixel-level label (additional to the manual pixel-level label) to learn the tumor segmentation.

Benefits of the WSTS include the TCH-ST integrating DRL and Self-Ensembling techniques, which for the first time achieves tumor segmentation from a non-enhanced image by exploiting the additional (bounding-)box-level labeled data. Also, the DDRL develops two detection strategies to locate a tumor jointly, which increases the DRL exploration range in the image and avoids the situation that traditional DRL (single strategy) sticks into sub-optimal that can lead to inaccurate tumor detection. Also, the USSE improves the tumor prediction reliability in the contrast-enhanced image by integrating uncertainty estimation with Self-Ensembling, which prevents error magnifying in the non-enhanced image segmentation. Moreover, the USSE introduces multi-scale attentions into the uncertainty-estimation; multi-scale attentions increase the observational uncertainty and thus improve the estimation effectiveness to the uncertainty.

A second example of a DRL approach provides a pixel-level graph reinforcement learning network (Pix-GRL) that directly inputs non-enhanced MRI tumor images and outputs CA-free-AI-enhanced MRI tumor images, which are comparable to traditional contrast-enhanced MRI tumor images. The Pix-GRL integrates a graph convolution into DRL for medical image synthesis where each pixel has a pixel-level agent, and each agent is based on the graph convolution to explore the pixel features and predict a pixel-level action. After all the pixel-level agents find pixel-level actions that maximize long-term rewards, Pix-GRL takes these actions to iteratively change the value of each pixel to generate high-quality CA-free-AI-enhanced MRI tumor images.

Integrating graph convolution into DRL to represent all pixel-level agents allows each pixel-level agent to benefit from the abilities of the node feature aggregation and the shared node weight parameters of the graph convolution during state exploration and action training, respectively. Thus, each pixel-level agent has the ability to effectively explore its own pixel's intrinsic long-range contextual features in a given state, avoiding the interference caused by ambiguous local features between and within pixels. Additionally, all pixel-level agents can be efficiently trained and output pixel-level actions for each pixel simultaneously using a shared training weight, avoiding the high algorithm complexity and computational cost caused by a large number of agents. Moreover, Pix-GRL uses a novel dual-level complementary reward to improve the accuracy of finding optimal pixel-level actions, boosting the agents' optimization. The reward combines a pixel-level reward function and a region-level reward function in action measuring to consider not only each pixel with its own future state but also those of neighboring pixels. It ensures that each agent pays attention to both the content details of each pixel and the local texture details of pixels during optimization while avoiding agents from falling into local optima.

Pix-GRL combines the graph-driven context-aware agent module and a dual-level complementary reward-based advantage function. The graph-driven context-aware agent module effectively explores the features of each pixel to efficiently obtain the pixel-level actions. It is performed by two networks: a state-behavior network and a state-evaluator network. The dual-level complementary reward-based advantage function measures all the pixel-level actions to reciprocally train these two networks and accurately find the optimal action to update the state. It is divided into two steps: a dual-level complementary reward computation and an advantage function computation.

Considering a non-enhanced MRI image as the initial current state, in the training phase, the state-behavior network estimates pixel-level candidate actions of the current state by observing the current state, while the state-evaluator network predicts a pixel-level average action as an empirical baseline that would have been taken at the current state. With the dual-level complementary reward measuring the improvement in two kinds of image synthesis actions, the advantage function computes the extra rewards by comparing the real rewards of the candidate actions with the expected rewards of the average action. It finds whether the candidate actions have resulted in better or worse results than the baseline action and takes the optimal action that has the most extra rewards to update the current state to the next state. Meanwhile, the advantage function feeds back to optimize both networks, namely, the advantage function enables the state-behavior network to estimate better candidate actions and enables the state-evaluator network to predict more accurate average actions, thereby computing an accurate advantage function to find an optimal action at the next state. The above process is repeated iteratively until a series of optimal actions are found to update the current state to be equivalent to Gd-contrast-enhanced tumor images. In the testing phase, the trained state-behavior network directly outputs a series of pixel-level actions to update the current state to CA-free-AI-enhanced tumor images according to the optimal actions of that state found in the training phase.

The dual-level complementary reward combines a pixel-level reward function based on Euclidean distance and a region-level reward function based on Wasserstein distance to improve the measurement accuracy. The reward ensures that each action considers not only each pixel with its own future state but also those of neighboring pixels and ensures that each pixel-level agent is optimized in both the pixel and local context texture of the state. The pixel reward function leverages the Euclidean distance to measure the improvement in every pixel value compared to each pixel in the current state and its own future state caused by that pixel's action. This function is able to optimize each pixel with its pixel-level agent independently to improve the effect of actions on the synthesis of pixel content details at each time state. The region reward function leverages the Wasserstein distance to measure the improvement in each action for the corresponding pixel and surrounding pixels between the current state and future state. This function is able to optimize neighboring actions jointly to improve the synthesis of the general context at each time state and avoid the local optima from the local optimization of only the pixel-level reward function. The Wasserstein distance is an effective function to measure the distance between two regions by calculating probability distributions. The Wasserstein distance effectively measures the improvement distance between the continuous distribution state and discrete distribution state caused by an independent action taken by different pixels. It also can consider the geometric characteristics between probability distributions of a state to reduce the distortion and artifacts in the future state after optimization.

The Pix-GRL technique may be operable without requiring a 1-to-1 relationship between pixel-level agent and image pixel with a 1-to-many relationship between pixel-level agent and image pixel being accommodated; for example each pixel-level agent may co-ordinate with a super-pixel block that includes a plurality of pixels such as a 1×2 pixel block or a 2×2 pixel block. However, modifying the pixel-level agent numbers to co-ordinate with a super-pixel block decreases the image resolution and risks a synthesized image that may not resolve small tumors.

Embodiments disclosed herein, or portions thereof, can be implemented by programming one or more computer systems or devices with computer-executable instructions embodied in a non-transitory computer-readable medium. When executed by a processor, these instructions operate to cause these computer systems and devices to perform one or more functions particular to embodiments disclosed herein. Programming techniques, computer languages, devices, and computer-readable media necessary to accomplish this are known in the art.

In an example, a non-transitory computer readable medium embodying a computer program for concurrent and simultaneous synthesis of a medical CA-free-AI-enhanced image and medical diagnostic image analysis may comprise: computer program code for receiving a magnetic resonance (MR) image acquired by a medical MR scanner in absence of contrast agent enhancement; computer program code for providing the MR image to a computer-implemented machine learning model; computer program code for concurrently performing a medical CA-free-AI-enhanced image synthesis task and a medical diagnostic image analysis task with the machine learning model; computer program code for reciprocally communicating between the image synthesis task and the image analysis task for mutually dependent training of both tasks. In another related example, the computer readable medium further comprises computer program code for training the machine learning model by deep reinforcement learning. In still another related example, the computer readable medium further comprises computer program code for acquiring scan data of a region of interest from an MRI scan, and reconstructing image data based on the scan data.

The computer readable medium is a data storage device that can store data, which can thereafter, be read by a computer system. Examples of a computer readable medium include read-only memory, random-access memory, CD-ROMs, magnetic tape, optical data storage devices and the like. The computer readable medium may be geographically localized or may be distributed over a network coupled computer system so that the computer readable code is stored and executed in a distributed fashion.

Computer-implementation of the system or method typically comprises a memory, an interface and a processor. The types and arrangements of memory, interface and processor may be varied according to implementations. For example, the interface may include a software interface that communicates with an end-user computing device through an Internet connection. The interface may also include a physical electronic device configured to receive requests or queries from a device sending digital and/or analog information. In other examples, the interface can include a physical electronic device configured to receive signals and/or data relating to contrast-agent-free medical diagnostic imaging, for example from an imaging scanner or image processing device.

Any suitable processor type may be used depending on a specific implementation, including for example, a microprocessor, a programmable logic controller or a field programmable logic array. Moreover, any conventional computer architecture may be used for computer-implementation of the system or method including for example a memory, a mass storage device, a processor (CPU), a graphical processing unit (GPU), a Read-Only Memory (ROM), and a Random-Access Memory (RAM) generally connected to a system bus of data-processing apparatus. Memory can be implemented as a ROM, RAM, a combination thereof, or simply a general memory unit. Software modules in the form of routines and/or subroutines for carrying out features of the system or method can be stored within memory and then retrieved and processed via processor to perform a particular task or function. Similarly, one or more method steps may be encoded as a program component, stored as executable instructions within memory and then retrieved and processed via a processor. A user input device, such as a keyboard, mouse, or another pointing device, can be connected to PCI (Peripheral Component Interconnect) bus. If desired, the software may provide an environment that represents programs, files, options, and so forth by means of graphically displayed icons, menus, and dialog boxes on a computer monitor screen. For example, any number of medical images and diagnostic parameters may be displayed, including for example CA-free-AI-enhanced medical image or an associated tissue segmentation or associated tumor detection.

Computer-implementation of the system or method may accommodate any type of end-user computing device including computing devices communicating over a networked connection. The computing device may display graphical interface elements for performing the various functions of the system or method, including for example display of a CA-free-AI-enhanced medical image or an associated tissue segmentation or associated tumor detection. For example, the computing device may be a server, desktop, laptop, notebook, tablet, personal digital assistant (PDA), PDA phone or smartphone, and the like. The computing device may be implemented using any appropriate combination of hardware and/or software configured for wired and/or wireless communication. Communication can occur over a network, for example, where remote control of the system is desired.

If a networked connection is desired the system or method may accommodate any type of network. The network may be a single network or a combination of multiple networks. For example, the network may include the Internet and/or one or more intranets, landline networks, wireless networks, and/or other appropriate types of communication networks. In another example, the network may comprise a wireless telecommunications network (e.g., cellular phone network) adapted to communicate with other communication networks, such as the Internet. For example, the network may comprise a computer network that makes use of a TCP/IP protocol (including protocols based on TCP/IP protocol, such as HTTP, HTTPS or FTP).

Medical implementation of methods, systems and computer readable media described herein provide concurrent and simultaneous synthesis of a medical CA-free-AI-enhanced image and medical diagnostic image analysis. Examples of medical implementations include: receiving a magnetic resonance (MR) image acquired by a medical MR scanner in absence of contrast agent enhancement; providing the MR image to a computer-implemented machine learning model; concurrently performing a medical CA-free-AI-enhanced image synthesis task and a medical diagnostic image analysis task with the machine learning model; and reciprocally communicating between the image synthesis task and the image analysis task for mutually dependent training of both tasks.

In some examples, the machine learning model may be trained by deep reinforcement learning, while in other examples, the machine learning model may include an artificial neural network. In a further example, the neural network may include at least one generative adversarial network (GAN).

In further examples of medical implementations, the medical diagnostic image analysis is a tissue segmented image and the machine learning model is a plurality of machine learning components, and includes: inputting the MR image into a first machine learning component; obtaining a coarse tissues mask from the first machine learning component; inputting the coarse tissues mask and the MR image into a second machine learning component; obtaining a CA-free-AI-enhanced image from the second machine learning component; inputting the CA-free-AI-enhanced image and the MR image into a third machine learning component; and obtaining a diagnosis-related tissue segmented image from the third machine learning component.

In a further example, the plurality of machine learning components comprises a first generative adversarial network (GAN), a second GAN and a third GAN. Medical implementation may include a sequential causal learning network (SCLN) connected to a generator network of each of the first, second and third GANs, the SCLN configured as an encoder of the MR image. In a further example, the SCLN may include a two-stream structure of a spatial perceptual pathway and a temporal perceptual pathway to independently extract spatial and temporal dependencies from the MR image. In a further example, each of the spatial perceptual pathway and the temporal perceptual pathway includes a dilated convolutional network. In a further example, a multi-attention weighing unit may be embedded within each of the spatial perceptual pathway and the temporal perceptual pathway to compute and select task-specific dependence within the spatial and temporal dependencies. In a further example, the multi-attention weighing unit may include: a first attention layer embedded in the spatial perceptual pathway to compute weights for spatial dependencies; a second attention layer embedded in the temporal perceptual pathway to compute weights for temporal dependencies; an add operator to fuse the weighted spatial and temporal dependencies; and a third attention layer to determine task-specific dependence of the fused spatial-temporal dependencies. In a further example, a generator network of the second GAN may be trained using a synthetic regularization loss term to improve quality of image synthesis, and a discriminator network of the second GAN may be trained using a synthetic content loss term. In a further example, a discriminator network of the third GAN may be trained using a self-supervised segmentation auxiliary loss term causing the discriminator network to extract a tissue-related compensate feature from the CA-free-AI-enhanced image.

In further examples, the MR image may be a time-series of MR images. The time-series of MR images may be cine MR images. In examples of cardiac imaging implementations, the time-series of MR images are cardiac MR images and implementation may include a neural network with a heart localization layer configured to automatically crop cardiac MR images to a region-of-interest.

In further examples of medical implementation, the medical diagnostic image analysis is a tumor detection and the machine learning model is a tripartite generative adversarial network (GAN) comprising a generator network, a discriminator network and a detector network, and includes: inputting the MR image into the generator network; obtaining a CA-free-AI-enhanced image and an attention map of tumor specific features from the generator network; inputting the CA-free-AI-enhanced image and the attention map into the detector network; obtaining a tumor location and a tumor classification extracted from the CA-free-AI-enhanced image by the detector network; and training the generator network by both adversarial learning with the discriminator network and back-propagation with the detector network.

In further examples, the generator network may include a dual attention module that produces the attention map. In further examples, the dual attention module may include first and second attention modules in parallel, the first attention module providing feature representation learning of tumor specificity and the second attention module providing global context learning of a multi-class aspect of the MR image. In further examples, information from the first attention module and the second attention module is fused to generate the attention map. In further examples, the generator network is an attention-aware generator, the discriminator network is a convolutional neural network-based (CNN-based) discriminator, and the detector network is a region-based convolutional neural network-based (R-CNN-based) detector. In further examples, the tripartite-GAN incorporates a tripartite loss function relating to three tasks of synthesis of the CA-free-AI-enhanced image, discrimination of the CA-free-AI-enhanced image and tumor classification of the CA-free-AI-enhanced image.

In a further example of medical implementation, the medical diagnostic image analysis is a tumor detection and the machine learning model is a pixel-level graph reinforcement learning model comprising a plurality of pixel-level agents equaling the number of pixels, each of the plurality of pixel-level agents associated with a single pixel, and a graph convolutional network communicative with all of the plurality of pixel-level agents, and includes: inputting the MR image into the pixel-level graph reinforcement learning model; determining an intensity value for each pixel of the MR image with the plurality of pixel-level agents according to a learned policy; and outputting a plurality of pixel-level actions, a single pixel-level action for each pixel of the MR image, to change the MR image to synthesize a CA-free-AI-enhanced image. In a further defined example, the graph convolutional network comprises a state-behavior network for generating pixel-level candidate actions and a state-evaluator network for generating pixel-level average actions and a reward function communicative with both the state-behavior network and the state-evaluator network, and includes: generating, for each pixel of the MR image, a pixel-level candidate action and a corresponding pixel-level average action; comparing each pixel-level candidate action with each corresponding pixel-level average action using the reward function and selecting an action for each corresponding pixel; and reciprocally training the state-behavior network and the state-evaluator network by communicating a parameter of the selected action to both the state-behavior network and the state-evaluator network.

In further examples, the communication of the parameter of the selected action trains the state-behavior network to improve estimates of the pixel-level candidate action and trains the state-evaluator network to improve prediction of pixel-level average action. In further examples, the reward function is a dual-level reward function combination of a pixel-level reward function and a regional-level reward function. In further examples, the pixel-level reward function is a Euclidean distance-based pixel-level reward function. and the regional-level reward function is a Wasserstein distance-based region-level reward function.

In a further example of medical implementation, the medical diagnostic image analysis is a tumor detection and the machine learning model is a weakly-supervised teacher-student network comprising a teacher module and a student module, and includes: inputting the MR image into a detection component of the student module; obtaining a fused tumor detection box locating a tumor in the MR image based on two tumor detection boxes generated by two detection strategies of the detection component; inputting the MR image and the fused tumor detection box into a segmentation component of the student module; and obtaining a tumor segmented MR image.

In further examples, the student detection component is a student dual-strategy deep reinforcement learning model comprising a first pair of cooperating relative-entropy biased actor-critic components; and the student segmentation component is a dense U-net. In further examples, the student detection component is guided by a tumor detection strategy provided by a detection component of the teacher module, and the student segmentation component is guided by a tumor mask provided by a segmentation component of the teacher module. In further examples, the detection component of the teacher module is a teacher dual-strategy deep reinforcement learning model comprising a second pair of cooperating relative-entropy biased actor-critic components trained by learning the tumor detection strategy from contrast-agent (CA)-enhanced MR image, and the segmentation component of the teacher module is a self-ensembling component including an uncertainty-estimation trained to learn tumor segmentation and generate a tumor mask. In further examples, the detection component of the teacher module inputs the CA-enhanced MR image and outputs a teacher-fused tumor detection box, and the segmentation component of the teacher module inputs the CA-enhanced MR image and the teacher-fused tumor detection box and outputs the tumor mask.

Medical implementation of methods, systems and computer readable media described herein can be used as an alternative to any CA-enhanced imaging and need not be limited to the exemplifications of ischemic heart disease and liver tumor detection described herein, as these exemplifications are illustrative only to demonstrate operability. For example, CA-free-AI-enhanced image synthesis task and diagnostic image analysis task can be used to substitute for CA-enhanced imaging and diagnosis in medical implementations of prostate imaging, kidney imaging, brain imaging, breast imaging, cardiovascular imaging, and the like.

Typically, the computer-implemented diagnostic task described herein extracts information from CA-free-AI-enhanced image to generate diagnostic information that is within 20% of (ie., less than 20% difference from) human expert analysis of comparable CA-enhanced images. In other examples, the computer-implemented diagnostic task described herein extracts information from CA-free-AI-enhanced image to generate diagnostic information that is within 15% of (ie., less than 15% difference from) human expert analysis of comparable CA-enhanced images. In other examples, the computer-implemented diagnostic task described herein extracts information from CA-free-AI-enhanced image to generate diagnostic information that is within 10% of (ie., less than 10% difference from) human expert analysis of comparable CA-enhanced images. Surveys of medical diagnosis variations show that range of inter-observer variation in samples of medical experts can often be 20%. Accordingly, the diagnostic task generating diagnostic information that is within 20% or within 15% or within 10% of human medical expert analysis achieves a satisfactory outcome as it falls within known human expert inter-observer variability.

The CA-free-AI-enhanced image synthesis task is evaluated primarily based on clinical outcomes of the associated diagnostic task; for example achieving a diagnostic accuracy that is within 20% of (ie., less than 20% difference from) expert analysis of comparable CA-enhanced images, or in other examples achieving a diagnostic accuracy that is within 15% of (ie., less than 15% difference from) expert analysis of comparable CA-enhanced images, or in still further examples achieving a diagnostic accuracy that is within 10% of (ie., less than 10% difference from) expert analysis of comparable CA-enhanced images. Secondary evaluations of the image synthesis task can be based on image-to-image comparisons between a CA-free-AI-enhanced image and a corresponding CA-enhanced image. For example, structural similarity index measure (SSIM) [ranging from 0-1], measures the structural similarity between synthesized CA-free-AI-enhanced images and comparable images with actual injected contrast agent. An SSIM=1 means two images are identical and usually SSIM>0.5 between a CA-free-AI-enhanced image and a corresponding ground truth CA-enhanced image indicates a similarity that can be useful for machine learned diagnostic task described herein.

Embodiments described herein are intended for illustrative purposes without any intended loss of generality. Still further variants, modifications and combinations thereof are contemplated and will be recognized by the person of skill in the art. Accordingly, the foregoing detailed description is not intended to limit scope, applicability, or configuration of claimed subject matter.

What is claimed is:

1. A medical imaging method for concurrent and simultaneous synthesis of a medical CA-free-AI-enhanced image and medical diagnostic image analysis comprising:
   receiving a magnetic resonance (MR) image acquired by a medical MR scanner in absence of contrast agent enhancement;
   providing the MR image to a computer-implemented machine learning model;
   concurrently performing a medical CA-free-AI-enhanced image synthesis task and a medical diagnostic image analysis task with the machine learning model;
   reciprocally communicating between the image synthesis task and the image analysis task for mutually dependent training of both tasks.

2. The method of claim 1, wherein the medical diagnostic image analysis is a tissue segmented image and the machine learning model is a plurality of machine learning components, the method further comprising:
   inputting the MR image into a first machine learning component;
   obtaining a coarse tissues mask from the first machine learning component;
   inputting the coarse tissues mask and the MR image into a second machine learning component;
   obtaining a CA-free-AI-enhanced image from the second machine learning component;
   inputting the CA-free-AI-enhanced image and the MR image into a third machine learning component;
   obtaining a diagnosis-related tissue segmented image from the third machine learning component.

3. The method of claim 2, wherein the plurality of machine learning components comprises a first generative adversarial network (GAN), a second GAN and a third GAN.

4. The method of claim 3, further comprising a sequential causal learning network (SCLN) connected to a generator network of each of the first, second and third GANs, the SCLN configured as an encoder of the MR image; and the SCLN comprises a two-stream structure of a spatial perceptual pathway and a temporal perceptual pathway to independently extract spatial and temporal dependencies from the MR image.

5. The method of claim 3, wherein a generator network of the second GAN is trained using a synthetic regularization loss term to improve quality of image synthesis, and a discriminator network of the second GAN is trained using a synthetic content loss term; and a discriminator network of the third GAN is trained using a self-supervised segmentation auxiliary loss term causing the discriminator network to extract a tissue-related compensate feature from the CA-free-AI-enhanced image.

6. The method of claim 1, wherein the medical diagnostic image analysis is a tumor detection and the machine learning model is a tripartite generative adversarial network (GAN) comprising a generator network, a discriminator network and a detector network, the method further comprising:
inputting the MR image into the generator network;
obtaining a CA-free-AI-enhanced image and an attention map of tumor specific features from the generator network;
inputting the CA-free-AI-enhanced image and the attention map into the detector network;
obtaining a tumor location and a tumor classification extracted from the CA-free-AI-enhanced image by the detector network;
training the generator network by both adversarial learning with the discriminator network and back-propagation with the detector network.

7. The method of claim 6, wherein the generator network includes a dual attention module that produces the attention map; and the dual attention module includes first and second attention modules in parallel, the first attention module providing feature representation learning of tumor specificity and the second attention module providing global context learning of a multi-class aspect of the MR image.

8. The method of claim 7, wherein information from the first attention module and the second attention module is fused to generate the attention map.

9. The method of claim 6, wherein the generator network is an attention-aware generator, the discriminator network is a convolutional neural network-based (CNN-based) discriminator, and the detector network is a region-based convolutional neural network-based (R-CNN-based) detector.

10. The method of claim 6, wherein the tripartite-GAN incorporates a tripartite loss function relating to three tasks of synthesis of the CA-free-AI-enhanced image, discrimination of the CA-free-AI-enhanced image and tumor classification of the CA-free-AI-enhanced image.

11. A medical imaging system for concurrent and simultaneous synthesis of a medical CA-free-AI-enhanced image and medical diagnostic image analysis comprising:
an interface device configured for receiving a magnetic resonance (MR) image acquired by a medical MR scanner in absence of contrast agent enhancement;
a memory configured for storing the MR image and a computer-implemented machine learning model;
a processor configured for:
inputting the MR image to the computer-implemented machine learning model;
concurrently performing a medical CA-free-AI-enhanced image synthesis task and a medical diagnostic image analysis task with the machine learning model;
reciprocally communicating between the image synthesis task and the image analysis task for mutually dependent training of both tasks.

12. The system of claim 11, wherein the medical diagnostic image analysis is a tissue segmented image and the machine learning model is a plurality of machine learning components, wherein the processor is configured for:
inputting the MR image into a first machine learning component;
obtaining a coarse tissues mask from the first machine learning component;
inputting the coarse tissues mask and the MR image into a second machine learning component;
obtaining a CA-free-AI-enhanced image from the second machine learning component;
inputting the CA-free-AI-enhanced image and the MR image into a third machine learning component;
obtaining a diagnosis-related tissue segmented image from the third machine learning component.

13. The system of claim 12, wherein the plurality of machine learning components comprises a first generative adversarial network (GAN), a second GAN and a third GAN.

14. The system of claim 13, further comprising a sequential causal learning network (SCLN) connected to a generator network of each of the first, second and third GANs, the SCLN configured as an encoder of the MR image; and the SCLN comprises a two-stream structure of a spatial perceptual pathway and a temporal perceptual pathway to independently extract spatial and temporal dependencies from the MR image.

15. The system of claim 13, wherein a generator network of the second GAN is trained using a synthetic regularization loss term to improve quality of image synthesis, and a discriminator network of the second GAN is trained using a synthetic content loss term; and a discriminator network of the third GAN is trained using a self-supervised segmentation auxiliary loss term causing the discriminator network to extract a tissue-related compensate feature from the CA-free-AI-enhanced image.

16. The system of claim 11, wherein the medical diagnostic image analysis is a tumor detection and the machine learning model is a tripartite generative adversarial network (GAN) comprising a generator network, a discriminator network and a detector network, wherein the processor is configured for:
inputting the MR image into the generator network;
obtaining a CA-free-AI-enhanced image and an attention map of tumor specific features from the generator network;
inputting the CA-free-AI-enhanced image and the attention map into the detector network;
obtaining a tumor location and a tumor classification extracted from the CA-free-AI-enhanced image by the detector network;
training the generator network by both adversarial learning with the discriminator network and back-propagation with the detector network.

17. The system of claim 16, wherein the generator network includes a dual attention module that produces the attention map; and the dual attention module includes first and second attention modules in parallel, the first attention module providing feature representation learning of tumor specificity and the second attention module providing global context learning of a multi-class aspect of the MR image.

18. The system of claim 17, wherein information from the first attention module and the second attention module is fused to generate the attention map.

19. The system of claim 16, wherein the generator network is an attention-aware generator, the discriminator network is a convolutional neural network-based (CNN-based) discriminator, and the detector network is a region-based convolutional neural network-based (R-CNN-based) detector.

20. The system of claim 16, wherein the tripartite-GAN incorporates a tripartite loss function relating to three tasks of synthesis of the CA-free-AI-enhanced image, discrimination of the CA-free-AI-enhanced image and tumor classification of the CA-free-AI-enhanced image.

21. A non-transitory computer readable medium embodying a computer program for concurrent and simultaneous synthesis of a medical CA-free-AI-enhanced image and medical diagnostic image analysis comprising:

computer program code for receiving a magnetic resonance (MR) image acquired by a medical MR scanner in absence of contrast agent enhancement;

computer program code for providing the MR image to a computer-implemented machine learning model;

computer program code for concurrently performing a medical CA-free-AI-enhanced image synthesis task and a medical diagnostic image analysis task with the machine learning model;

computer program code for reciprocally communicating between the image synthesis task and the image analysis task for mutually dependent training of both tasks.

* * * * *